US009284277B2

(12) United States Patent
Robarge et al.

(10) Patent No.: US 9,284,277 B2
(45) Date of Patent: Mar. 15, 2016

(54) BENZAZEPINES AS SEROTONIN 5-HT$_{2C}$ RECEPTOR LIGANDS AND USES THEREOF

(71) Applicant: ABT Holding Company, Cleveland, OH (US)

(72) Inventors: Mike Robarge, Burton, OH (US); John Harrington, Cleveland, OH (US); David Gerrish, Cleveland, OH (US); John Mecom, Cleveland, OH (US)

(73) Assignee: ABT Holding Company, Cleveland, OH (US)

( * ) Notice: Subject to any disclaimer, the term of this patent is extended or adjusted under 35 U.S.C. 154(b) by 108 days.

(21) Appl. No.: 14/138,866

(22) Filed: Dec. 23, 2013

(65) Prior Publication Data

US 2014/0194411 A1   Jul. 10, 2014

Related U.S. Application Data

(60) Provisional application No. 61/745,241, filed on Dec. 21, 2012.

(51) Int. Cl.
*A61K 31/55* (2006.01)
*C07D 223/14* (2006.01)
*C07D 223/32* (2006.01)
*C07D 401/04* (2006.01)
*C07D 417/04* (2006.01)
*C07D 491/048* (2006.01)
*C07D 491/052* (2006.01)

(52) U.S. Cl.
CPC ............ *C07D 223/32* (2013.01); *C07D 401/04* (2013.01); *C07D 417/04* (2013.01); *C07D 491/048* (2013.01); *C07D 491/052* (2013.01)

(58) Field of Classification Search
CPC .... A61K 31/55; C07D 223/14; C07D 223/32; C07D 401/04; C07D 417/04; C07D 491/048; C07D 491/052
USPC .............. 514/212.02, 215, 217; 540/543, 586
See application file for complete search history.

(56) References Cited

U.S. PATENT DOCUMENTS

| | | | |
|---|---|---|---|
| 4,255,445 A * | 3/1981 | Brush et al. ............... | 514/215 |
| 4,414,225 A | 11/1983 | Sauter et al. | |
| 4,575,504 A | 3/1986 | Sauter et al. | |
| 4,904,653 A | 2/1990 | Clark et al. | |
| 5,258,378 A | 11/1993 | Clark et al. | |
| 5,512,562 A | 4/1996 | Hohlweg | |
| 5,532,240 A | 7/1996 | Nakao et al. | |
| 5,691,330 A | 11/1997 | Nakao et al. | |
| 5,998,433 A | 12/1999 | Takatani et al. | |
| 2006/0003990 A1 | 1/2006 | Bennani et al. | |

FOREIGN PATENT DOCUMENTS

| | | |
|---|---|---|
| CA | 2104371 | 6/1993 |
| EP | 2522671 | 11/2012 |
| WO | WO 93/13105 | 7/1993 |
| WO | WO 96/11201 | 4/1996 |
| WO | WO 02/34760 | 5/2002 |
| WO | WO 2004/024065 | 3/2004 |
| WO | WO 2005/003096 | 1/2005 |
| WO | WO 2005/019179 | 3/2005 |
| WO | WO 2005/040169 | 5/2005 |
| WO | WO 2005/042490 | 5/2005 |
| WO | WO 2005/042491 | 5/2005 |

OTHER PUBLICATIONS

International Search Report and Written Opinion issued Jun. 24, 2014 in corresponding International Application No. PCT/US2013/077501.
Glennon, "Serotonin Receptors: Clinical Implications", Neuroscience & Biobehavioral Reviews. vol. 14, 1990, pp. 35-47.
Baxter et al., "5-HT2 receptor subtypes: a family re-united?", TIPS, vol. 16, Mar. 1995, pp. 105-110.
Bos et al., "Novel agonists of 5HT2c receptors. Syntheses and biological evaluation of substituted 2-(indol-1-yl)-1-methylethylamines and 2-(indeno[1,2-b]pyrrol-1-yl)-1-methylethylamines. Improved therapeutics for obsessive compulsive disorder", J. Med. Chem. 40, 1997, pp. 2762-2769.
Martin et al., "5-HT2c receptor agonists: pharmacological characteristics and therapeutic potential", The Journal of Pharmacology and Experimental Therapeutics, vol. 286, No. 2, 1998, pp. 913-924.
Berge et al., "Pharmaceutical salts", Pharmaceutical Sciences, vol. 66, No. 1, Jan. 1977, pp. 1-19.
Higuchi et al., "Pro-drugs as novel drug delivery systems", American Chemical Society, 1975, pp. 1-3.
Roche et al., "Bioreversible carriers in drug design theory and application", American Pharmaceutical Association and Pergamon Press (1987), pp. 1-4.
Grottick et al., "Studies to investigate the role of 5-HT2c receptors on cocaine- and food-maintained behavior", The Journal of Pharmacology and Experimental Therapeutics, vol. 295 No. 3, 2000, pp. 1183-1191.
Higgins et al., "Serotonin and drug reward: focus on 5-HT2c receptors", European Journal of Pharmacology, 480, 2003, pp. 151-162.
Grauer et al., "WAY-163909, a 5-HT2c agonist, enhances the preclinical potency of current antipsychotics", Psychopharmacology, 2009, 204, pp. 37-48.
Siuciak et al., "CP-809,101, a selective 5-HT2c agonist, shows activity in animal models of antipsychotic activity", Neuropharmacology, 52, 2007, pp. 279-290.
Jenck et al., "The role of 5-HT2c receptors in affective disorders", Expert Opinion on Investigational Drugs, 1998, 7(10), pp. 1587-1600.
Halford, "Obesity drugs in clinical development", Current Opinion in Investigational Drugs, 2006, vol. 7 No. 4, pp. 321-318.

(Continued)

*Primary Examiner* — Brenda Coleman
(74) *Attorney, Agent, or Firm* — Wood, Phillips, Katz, Clark & Mortimer

(57) ABSTRACT

The present invention generally relates to a series of compounds, to pharmaceutical compositions containing the compounds, and to use of the compounds and compositions as therapeutic agents. More specifically, compounds of the present invention are benzazepine compounds. These compounds are serotonin receptor (5-HT$_{2C}$) ligands and are useful for treating diseases, disorders, and conditions wherein modulation of the activity of serotonin receptors (5-HT$_{2C}$) is desired (e.g. addiction, anxiety, depression, obesity, and others).

21 Claims, No Drawings

(56) References Cited

OTHER PUBLICATIONS

Miller "Serotonin 5-HT2c receptor agonists: potential for the treatment of obesity", Molecular Interventions, Oct. 2005, vol. 5 issue 5, pp. 282-291.

Methvin, "Serotonergic 5-HT2C receptors as a potential therapeutic target for the design antiepileptic drugs", Current Topics in Medicinal Chemistry, 2005, 5, pp. 59-67.

Zhou et al., "Serotonin 2C receptor agonists improve type 2 diabetes via melanocortin-4 receptor signaling pathways", Cell Metab. Nov. 2007, 071 6(5), pp. 398-405.

Poste et al., "Lipid vesicles as carriers for introducing biologically active materials into cells", Methods in Cell Biology, vol. XIV, 1976, pp. 33-71.

* cited by examiner

BENZAZEPINES AS SEROTONIN 5-HT$_{2C}$ RECEPTOR LIGANDS AND USES THEREOF

FIELD OF THE INVENTION

The present invention generally relates to a series of compounds, to pharmaceutical compositions containing the compounds, and to use of the compounds and compositions as therapeutic agents. More specifically, compounds of the present invention are benzazepines. These compounds are serotonin receptor (5-HT$_{2C}$) ligands and are useful for treating diseases, disorders, and conditions wherein modulation of the activity of serotonin receptors (5-HT$_{2C}$) is desired (e.g. addiction, anxiety, depression, obesity and others).

BACKGROUND OF THE INVENTION

Serotonin has been implicated in a number of diseases, disorders, and conditions that originate in the central nervous system, including diseases, disorders, and conditions related to, for example, sleeping, eating, perceiving pain, controlling body temperature, controlling blood pressure, depression, anxiety, addiction and schizophrenia. Serotonin also plays an important role in peripheral systems, such as the gastrointestinal system, where it has been found to mediate a variety of contractile, secretory and electrophysiologic effects.

Because of the broad distribution of serotonin within the body, there is a need for drugs that affect serotonergic systems. In particular, agonists, partial agonists, and antagonists of serotonergic systems are of interest for the treatment of a wide range of disorders, including anxiety, depression, hypertension, migraine, obesity, compulsive disorders, schizophrenia, autism, neurodegenerative disorders (e.g., Alzheimer's disease, Parkinsonism and Huntington's chorea), and chemotherapy-induced vomiting.

The major classes of serotonin receptors (5-HT$_{1-7}$) contain one to seven separate receptors that have been formally classified. See Glennon, et al., *Neuroscience and Behavioral Reviews*, 1990, 14, 35; and D. Hoyer, et al. *Pharmacol. Rev.* 1994, 46, 157-203.

For example, the 5-HT$_2$ family of receptors contains 5-HT$_{2a}$, 5-HT$_{2b}$, and 5-HT$_{2c}$ subtypes, which have been grouped together on the basis of primary structure, secondary messenger system, and operational profile. All three 5-HT$_2$ subtypes are G-protein coupled, activate phospholipase C as a principal transduction mechanism, and contain a seven-transmembrane domain structure. There are distinct differences in the distribution of the three 5-HT$_2$ subtypes in a mammal. The 5-HT$_{2b}$ and 5-HT$_{2a}$ receptors are widely distributed in the peripheral nervous system, with 5-HT$_{2a}$ also found in the brain. The 5-HT$_{2c}$ receptor has been found only in the central nervous system, being highly expressed in many regions of the human brain. See G. Baxter, et al. *Trends in Pharmacol. Sci.* 1995, 16, 105-110.

Subtype 5-HT$_{2a}$ has been associated with effects including vasoconstriction, platelet aggregation, and bronchoconstriction, as well as certain CNS effects, while subtype 5-HT$_{2c}$ has been associated with diseases that include depression, anxiety, obsessive compulsive disorder, addiction, panic disorders, phobias, psychiatric syndromes, and obesity. Very little is known about the pharmocologic role of the 5-HT$_{2b}$ receptor. See F. Jenck, et al., *Exp. Opin. Invest. Drugs*, 1998, 7, 1587-1599; M. Bos, et al., *J. Med. Chem.*, 1997, 40, 2762-2769; J. R. Martin, et al., *The Journal of Pharmacology and Experimental Therapeutics*, 1998, 286, 913-924; S. M. Bromidge, et al., 1. *Med. Chem.*, 1998, 41, 1598-1612; G. A. Kennett, *Drugs*, 1998, 1, 4, 456-470; and A. Dekeyne, et al., *Neuropharmacology*, 1999, 38, 415-423.

WO 93/13105, U.S. Pat. Nos. 5,691,330 and 5,532,240 disclose thiophene derivatives; U.S. Pat. No. 4,414,225 discloses thiophene, furan and pyrrole derivatives; U.S. Pat. No. 4,575,504 discloses thienothiazole derivatives; U.S. Pat. No. 5,258,378 discloses certain pyrroloazepine compounds; U.S. Pat. Nos. 4,414,225 and 4,904,653 disclose certain azepine derivatives; WO 2005/019179 discloses certain benzazepines, WO 2005/003096, WO 2005/042490, and WO 2005/042491 disclose benzazepine derivatives; WO 96/11201 discloses furan derivatives; WO 2005/040169 discloses certain fused pyrrole- and pyrazole-containing heterocyclic compounds which are serotonin modulators; WO 2004/024065 discloses substituted bicyclic thiophene derivatives. None of these patents or patent applications disclose compounds of the instant invention.

SUMMARY OF THE INVENTION

The present invention is directed to compounds of the formula:

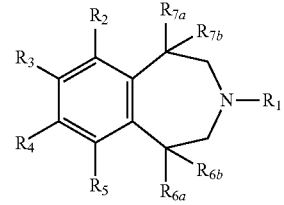

where
R$_1$ is selected from the group consisting of H, alkyl, perhaloalkyl, alkanoyl, C$_{1-8}$ alkylaryl, and C$_{1-8}$ alkylheteroaryl;
R$_2$ and R$_3$ are independently selected from the group consisting of H, halogen, C$_{1-8}$ alkyl, C$_{2-8}$ alkenyl, C$_{2-8}$ alkynyl, perhaloalkyl, CN, OR$_8$, NR$_8$R$_9$, SR$_8$, OCOR$_{10}$, CONR$_8$R$_9$, NR$_8$COR$_{10}$, NR$_8$CO$_2$R$_{10}$, SO$_2$NR$_8$R$_9$, SO$_2$R$_{10}$, NR$_8$SO$_2$R$_{10}$, aryl, heteroaryl, C$_{1-8}$ alkylaryl, and C$_{1-8}$ alkylheteroaryl;
R$_4$ and R$_5$ together with the atoms which they are attached form a 5- or 6-membered carbocycle, benzofuran, dihydrobenzofuran or benzopyrane ring, substituted with one or more of each of R$_{11a}$, R$_{11b}$, R$_{12a}$, R$_{12b}$, R$_{13a}$, R$_{13b}$, R$_{14a}$, and R$_{14b}$;
R$_{6a}$ and R$_{6b}$ are independently selected from the group consisting of H, C$_{1-8}$alkyl, OR$_8$, aryl, and heteroaryl; or R$_{6a}$ and R$_{6b}$ taken together are —CH$_2$CH$_2$—;
R$_{7a}$ and R$_{7b}$ are independently selected from the group consisting of H, OR$_8$, alkyl, OR$_8$, aryl, and heteroaryl; or R$_{7a}$ and R$_{7b}$ taken together are —CH$_2$CH$_2$—;
R$_8$ is selected from the group consisting of H, C$_{1-8}$alkyl, C$_{2-8}$ alkenyl, C$_{2-8}$ alkynyl, perhaloalkyl (preferably CF$_3$), C$_{1-8}$ alkyl-O—C$_{1-8}$ alkyl, aryl, heteroaryl, C$_{1-8}$ alkyl-O-aryl, C$_{1-8}$ alkyl-O-heteroaryl, C$_{1-8}$ alkylaryl, and C$_{1-8}$ alkylheteroaryl;
R$_9$ is selected from the group consisting of H, C$_{1-8}$alkyl, C$_{2-8}$ alkenyl, C$_{2-8}$ alkynyl, perhaloalkyl (preferably CF$_3$), C$_{1-8}$ alkyl-O—C$_{1-8}$ alkyl, aryl, heteroaryl, C$_{1-8}$ alkyl-O-aryl, C$_{1-8}$ alkyl-O-heteroaryl, C$_{1-8}$ alkylaryl, and C$_{1-8}$ alkylheteroaryl;
R$_{10}$ is selected from the group consisting of C$_{1-8}$ alkyl, C$_{2-8}$ alkenyl, C$_{2-8}$ alkynyl, perhaloalkyl (preferably CF$_3$), C$_{1-8}$ alkyl-O—C$_{1-8}$ alkyl, aryl, heteroaryl, C$_{1-8}$ alkyl-O-aryl, C$_{1-8}$ alkyl-O-heteroaryl, C$_{1-8}$ alkylaryl, and C$_{1-8}$ alkylheteroaryl;
R$_{11a}$ and R$_{11b}$ are independently selected from the group consisting of H, halogen, C$_{1-8}$ alkyl, perhaloalkyl (preferably CF$_3$), aryl, and heteroaryl;

$R_{12a}$ and $R_{12b}$ are independently selected from the group consisting of H, halogen, $C_{1-8}$ alkyl, perhalo alkyl (preferably $CF_3$), aryl, and heteroaryl, with the proviso that when the formula is

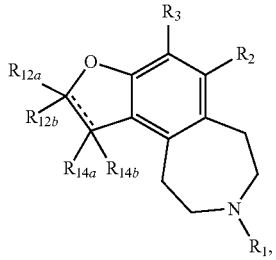

then $R_{12b}$ is not present;

$R_{13a}$ and $R_{13b}$ are independently selected from the group consisting of H, halogen, $C_{1-8}$ alkyl, perhaloalkyl (preferably $CF_3$), aryl, and heteroaryl;

$R_{14a}$ and $R_{14b}$ are independently selected from the group consisting of H, halogen, $C_{1-8}$ alkyl, $C_{2-8}$ alkenyl, $C_{2-8}$ alkynyl, perhaloalkyl (preferably $CF_3$), CN, $OR_8$, $NR_8R_9$, $SR_8$, $OCOR_{10}$, $OCONR_8R_9$, $CONR_8R_9$, $NR_8COR_{10}$, $NR_8CO_2R_{10}$, $NR_8SO_2R_{10}$, aryl, heteroaryl, $C_{1-8}$ alkylaryl, and $C_{1-8}$ alkylheteroaryl, with the proviso that when the formula is

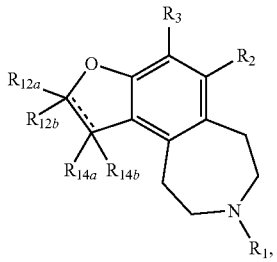

then $R_{14b}$ is not present;

In another embodiment, the compounds of the invention have the formula:

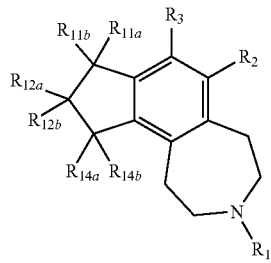

In one embodiment, the invention provides a compound wherein $R_1$, $R_2$, $R_3$, $R_{6a}$, $R_{6b}$, $R_{7a}$, $R_{7b}$ are H; and $R_4$ and $R_5$ together with the atoms which they are attached form a 5-membered carbocycle ring, substituted with one or more of each of $R_{11a}$, $R_{11b}$, $R_{12a}$, $R_{12b}$, $R_{14a}$, and $R_{14b}$.

In one embodiment, $R_{11a}$ and $R_{11b}$ are both H.

In another embodiment, $R_{12a}$ and $R_{12b}$ are both F.

In another embodiment, $R_{14a}$ aryl and $R_{14b}$ is H.

In another embodiment, the compounds of the invention have the formula:

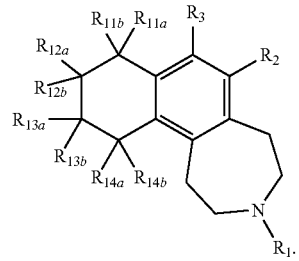

In another embodiment, the compounds of the invention have the formula:

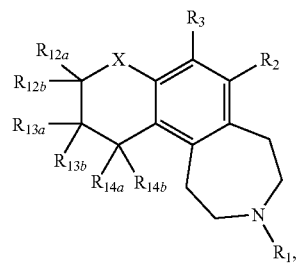

wherein X is C, S, $SO_2$ or O.

In another embodiment, the compounds of the invention have the formula:

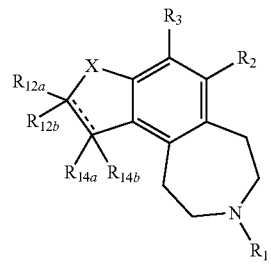

wherein X is C, S, $SO_2$ or O.

In a preferred embodiment, $R_1$ is H.

In one preferred embodiment, the invention provides a compound of one of the formulas:

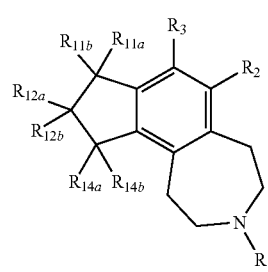 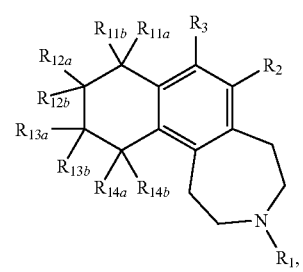

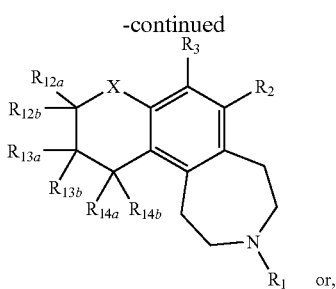

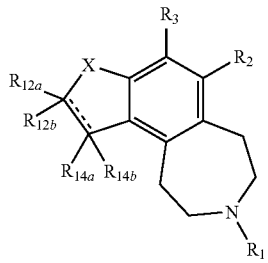

wherein
X is C, S, SO$_2$ or O;
R$_1$ is H;
R$_2$ and R$_3$ are independently selected from the group consisting of H and halogen;
R$_{11a}$, R$_{11b}$, R$_{12a}$, R$_{12b}$, R$_{13a}$ and R$_{13b}$ are independently selected from the group consisting of H and halogen; and
R$_{14a}$ and R$_{14b}$ are independently selected from the group consisting of H, halogen, C$_{1-8}$ alkyl, aryl, heteroaryl, C$_{1-8}$alkylaryl, and C$_{1-8}$ alkylheteroaryl;
with the proviso that when the formula is

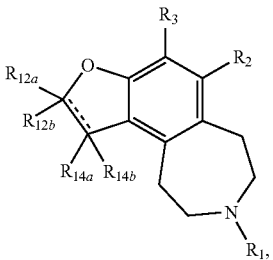

then R$_{12b}$ and R$_{14b}$ are not present.

In some embodiments, the invention provides the following compounds:
1,2,3,6,7,8,9,10-octahydro-8-aza-cyclohepta[e]indene;
1-Methyl-1,2,3,6,7,8,9,10-octahydro-8-aza-cyclohepta[e]indene;
1-Ethyl-1,2,3,6,7,8,9,10-octahydro-8-aza-cyclohepta[e]indene;
1-Cyclopropyl-1,2,3,6,7,8,9,10-octahydro-8-aza-cyclohepta[e]indene;
1-Propyl-1,2,3,6,7,8,9,10-octahydro-8-aza-cyclohepta[e]indene;
4-Chloro-1-ethyl-1,2,3,6,7,8,9,10-octahydro-8-aza-cyclohepta[e]indene;
1-Ethyl-4-iodo-1,2,3,6,7,8,9,10-octahydro-8-aza-cyclohepta[e]indene;
1-Ethyl-4-fluoro-1,2,3,6,7,8,9,10-octahydro-8-aza-cyclohepta[e]indene;
1-Phenyl-1,2,3,6,7,8,9,10-octahydro-8-aza-cyclohepta[e]indene;
4-Chloro-1-phenyl-1,2,3,6,7,8,9,10-octahydro-8-aza-cyclohepta[e]indene;
1-Pyridin-3-yl-1,2,3,6,7,8,9,10-octahydro-8-aza-cyclohepta[e]indene;
4-Fluoro-1-pyridin-3-yl-1,2,3,6,7,8,9,10-octahydro-8-aza-cyclohepta[e]indene;
1,1-Dimethyl-1,2,3,6,7,8,9,10-octahydro-8-aza-cyclohepta[e]indene;
2,2-Difluoro-1-phenyl-1,2,3,6,7,8,9,10-octahydro-8-aza-cyclohepta[e]indene;
2,2-Difluoro-1-o-tolyl-1,2,3,6,7,8,9,10-octahydro-8-aza-cyclohepta[e]indene;
2,2-Difluoro-1-m-tolyl-1,2,3,6,7,8,9,10-octahydro-8-aza-cyclohepta[e]indene;
2,2-Difluoro-1-p-tolyl-1,2,3,6,7,8,9,10-octahydro-8-aza-cyclohepta[e]indene;
2,2-Difluoro-1-(3-trifluoromethyl-phenyl)-1,2,3,6,7,8,9,10-octahydro-8-aza-cyclohepta[e]indene;
2,2-Difluoro-1-(3-trifluoromethoxy-phenyl)-1,2,3,6,7,8,9,10-octahydro-8-aza-cyclohepta[e]indene;
2,2-Difluoro-1-(4-fluoro-phenyl)-1,2,3,6,7,8,9,10-octahydro-8-aza-cyclohepta[e]indene;
2,2-Difluoro-1-(3-fluoro-phenyl)-1,2,3,6,7,8,9,10-octahydro-8-aza-cyclohepta[e]indene;
1-Cyclopropyl-2,2-difluoro-1,2,3,6,7,8,9,10-octahydro-8-aza-cyclohepta[e]indene;
1-(3-Chloro-phenyl)-2,2-difluoro-1,2,3,6,7,8,9,10-octahydro-8-aza-cyclohepta[e]indene;
1-(4-Chloro-phenyl)-2,2-difluoro-1,2,3,6,7,8,9,10-octahydro-8-aza-cyclohepta[e]indene;
2,2-Difluoro-1-(2-methoxy-phenyl)-1,2,3,6,7,8,9,10-octahydro-8-aza-cyclohepta[e]indene;
2,2-Difluoro-1-(3-methoxy-phenyl)-1,2,3,6,7,8,9,10-octahydro-8-aza-cyclohepta[e]indene;
2,2-Difluoro-1-(4-methoxy-phenyl)-1,2,3,6,7,8,9,10-octahydro-8-aza-cyclohepta[e]indene;
2,2-Difluoro-1-pyridin-3-yl-1,2,3,6,7,8,9,10-octahydro-8-aza-cyclohepta[e]indene;
2,2-Difluoro-1-pyridin-4-yl-1,2,3,6,7,8,9,10-octahydro-8-aza-cyclohepta[e]indene;
4-Chloro-2,2-difluoro-1-pyridin-3-yl-1,2,3,6,7,8,9,10-octahydro-8-aza-cyclohepta[e]indene;
1-Ethyl-2,2-difluoro-1,2,3,6,7,8,9,10-octahydro-8-aza-cyclohepta[e]indene;
2,2-Difluoro-1-methyl-1,2,3,6,7,8,9,10-octahydro-8-aza-cyclohepta[e]indene;
1-Benzyl-2,2-difluoro-1,2,3,6,7,8,9,10-octahydro-8-aza-cyclohepta[e]indene;
2,2-Difluoro-1,1-dimethyl-1,2,3,6,7,8,9,10-octahydro-8-aza-cyclohepta[e]indene;
1,1-Dimethyl-4-phenyl-1,2,3,6,7,8,9,10-octahydro-8-aza-cyclohepta[e]indene;
1-Ethyl-1,2,7,8,9,10-hexahydro-6H-3-oxa-8-aza-cyclohepta[e]indene;
1-Ethyl-2,3,8,9,10,11-hexahydro-1H,7H-4-oxa-9-aza-cyclohepta[a]naphthalene;
2,2-Difluoro-1-methoxy-1,2,3,6,7,8,9,10-octahydro-8-aza-cyclohepta[e]indene;
1-Phenyl-7,8,9,10-tetrahydro-6H-3-oxa-8-aza-cyclohepta[e]indene;
1-Thiazol-2-yl-1,2,3,6,7,8,9,10-octahydro-8-aza-cyclohepta[e]indene;
1-Ethoxy-2,2-difluoro-1,2,3,6,7,8,9,10-octahydro-8-aza-cyclohepta[e]indene;

2,2-Difluoro-1,2,3,6,7,8,9,10-octahydro-8-aza-cyclohepta[e]indene; and

1-Methoxy-1,2,3,6,7,8,9,10-octahydro-8-aza-cyclohepta[e]indene.

The invention also encompasses pharmaceutically acceptable salts of the provided compounds, as well as isomers and racemic mixtures.

Another embodiment of the present invention provides a pharmaceutical composition comprising a compound of the present invention or a pharmaceutically acceptable salt thereof, and a pharmaceutically acceptable carrier.

Still another embodiment of the present invention provides a method of treating a disease, disorder and/or condition in a mammal (e.g., animal or human), wherein a 5-$HT_{2c}$ receptor is implicated and modulation of a 5-$HT_{2c}$ function is desired. The method comprises administering a therapeutically effective amount of a compound of the present invention, or a pharmaceutically acceptable salt thereof, to the mammal.

Yet another embodiment of the present invention comprises a method of modulating 5-HT receptor function with an effective amount of compound of the present invention, or a pharmaceutically acceptable salt thereof.

A further embodiment of the present invention provides a method of treating or preventing diseases, disorders, and/or conditions of the central nervous system. The method comprises administering a therapeutically effective amount of a compound of the present invention, or a pharmaceutically acceptable salt thereof, to the mammal.

Specific diseases, disorders and/or conditions for which compounds of the invention may have activity include obesity, depression, schizophrenia, anxiety, obsessive compulsive disorder, addiction, panic disorders, sleep disorders, migraine, Type II diabetes, epilepsy, phobias and psychiatric syndromes.

DETAILED DESCRIPTION OF THE INVENTION

The following definitions are used, unless otherwise described:

The term "alkanoyl" has the general formula RCO—, where R represents an alkyl group. The term acyl can also be used to describe this group. The acyl group is usually derived from a carboxylic acid. Therefore, an alkanoyl group will also include acyl moieties derived from amino acids and dipeptides.

The term "alkyl" as used herein, alone or in combination, includes straight chained and branched hydrocarbon groups containing the indicated number of carbon atoms, typically methyl, ethyl, and straight chain and branched propyl and butyl groups. The term "alkyl" also encompasses cycloalkyl, i.e., a cyclic $C_3$-$C_8$ hydrocarbon group, such as cyclopropyl, cyclobutyl, cyclopentyl, and cyclohexyl.

The term "alkenyl" as used herein, alone or in combination, refers to a substituted or unsubstituted straight chain or substituted or unsubstituted branched-chain alkenyl radical containing from 2 to 10 carbon atoms. Examples of such include, but are not limited to, ethenyl, E- and Z-pentenyl, decenyl and the like.

The term "alkynyl" as used herein, alone or in combination, refers to a substituted or unsubstituted straight or substituted or unsubstituted branched chain alkynyl moiety containing from 2 to 10 carbon atoms. Examples of such include, but are not limited to, ethynyl, propynyl, propargyl, butynyl, hexynyl, decynyl and the like.

The term "alkoxy" as used herein, alone or in combination, refers to an alkyl ether moiety, wherein the term "alkyl" is as defined above. Examples of suitable alkyl ether moieties include, but are not limited to, methoxy, ethoxy, n-propoxy, iso-propoxy, n-butoxy, iso-butoxy, secbutoxy, tert-butoxy and the like.

The term "halo" as used herein, alone or in combination, includes fluoro, chloro, bromo, or iodo. Similarly, the term "halogen" is defined herein to include fluorine, chlorine, bromine, and iodine.

The term "amino" as used herein, alone or in combination, alone or in combination, includes the group —$NH_2$ or —$NR_6R_7$.

The term "aryl," as used herein, alone or in combination, is defined herein as a monocyclic or bicyclic aromatic group (e.g., phenyl or naphthyl) that can be unsubstituted or substituted, for example, with one or more, and in particular one to three of the following substituents selected from the group consisting of H, halo, CN, $NO_2$, $CF_3$, $N_3$, $C_{1-6}$ alkyl, OH, $NR_6R_7$, $OC_{1-6}$ alkyl, $OR_6$, C(=O)$NR_aR_b$, C(=OS)$N_6R_7$, tetrazoyl, triazoyl, amidinyl, guanidinyl, thioguanidinyl, cyanoguanadinyl, and aryl. Generally, "aryl" denotes a phenyl group, or an ortho-fused bicyclic carbocyclic group having nine to ten ring atoms in which at least one ring is aromatic (e.g. naphthyl or tetrahydronaphthyl). The term "aryl" also is abbreviated in the various chemical structures as "Ar."

The term "carbocyclic" as used herein, alone or in combination, includes any closed ring of carbon atoms, including alicyclic and aromatic structures.

The term "heteroaryl" as used herein, alone or in combination, includes a monocyclic, bicyclic, or tricyclic ring system containing one, two, or three aromatic rings and containing at least one nitrogen, oxygen, or sulfur atom in an aromatic ring, and which can be unsubstituted or substituted, for example, with one or more, and in particular one to three, substituents, such as halo, alkyl, hydroxy, hydroxyalkyl, alkoxy, alkoxyalkyl, haloalkyl, nitro, amino, alkylamino, acylamino, alkylthio, alkylsulfonyl, and alkylsulfonyl. Examples of heteroaryl groups include, but are not limited to, 2H-pyrrolyl, 3H-indolyl, 4H-quinolizinyl, 4H-carbazolyl, acridinyl, benzo[b]thienyl, benzothiazolyl, 1,3-carbolinyl, carbazolyl, chromenyl, cinnaolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, naptho[2,3-b], oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, and xanthenyl. In one embodiment the term "heteroaryl" denotes a monocyclic aromatic ring containing five or six ring atoms containing carbon and 1, 2, 3, or 4 heteroatoms independently selected from the group consisting of non-peroxide oxygen, sulfur, and N(Z) wherein Z is absent or is H, 0, $C_{1-4}$alkyl, phenyl or benzyl. In another embodiment heteroaryl denotes an ortho-fused bicyclic heterocycle of about eight to ten ring atoms.

The term "Het" generally represents a heterocyclic group, saturated or partially unsaturated, containing at least one heteroatom selected from the group consisting of oxygen, nitrogen, and sulfur, and optionally substituted with $C_{1-6}$ alkyl or C(=O)$OR_6$. Typically "Het" is a monocyclic, bicyclic, or tricyclic group containing one or more heteroatoms selected from the group consisting of oxygen, nitrogen, and sulfur. A "Het" group also can contain an oxo group (=0) attached to the ring. Nonlimiting examples of Het groups include 1,3-dihydrobenzofuran, 1,3-dioxolane, 1,4 dioxane, 1,4-dithiane, furanyl, imidazolyl, 2H-pyran, 2-pyrazoline, 4H-pyran, chromanyl, imidazolidinyl, imidazolinyl, indolinyl, isochromanyl, isoindolinyl, morpholine, oxazolyl, piperazinyl, piperidine, piperidynyl, pyrazolidine, pyrimidinyl, pyrazolidinyl, pyrazolinyl, pyrrolidine, pyrroline, quinuclidine, and thiomorpholine.

The present invention is directed to compounds of the formula:

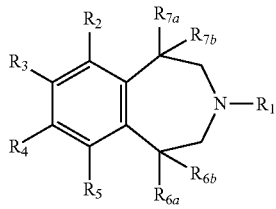

where
$R_1$ is selected from the group consisting of H, alkyl, perhaloalkyl, alkanoyl, $C_{1-8}$ alkylaryl, and $C_{1-8}$ alkylheteroaryl;
$R_2$ and $R_3$ are independently selected from the group consisting of H, halogen, $C_{1-8}$ alkyl, $C_{2-8}$ alkenyl, $C_{2-8}$ alkynyl, perhaloalkyl, CN, $OR_8$, $NR_8R_9$, $SR_8$, $OCOR_{10}$, $CONR_8R_9$, $NR_8COR_{10}$, $NR_8CO_2R_{10}$, $SO_2NR_8R_9$, $SO_2R_{10}$, $NR_8SO_2R_{10}$, aryl, heteroaryl, $C_{1-8}$ alkylaryl, and $C_{1-8}$ alkylheteroaryl;
$R_4$ and $R_5$ together with the atoms which they are attached form a 5- or 6-membered carbocycle, benzofuran, dihydrobenzofuran or benzopyrane ring, substituted with one or more of each of $R_{11a}$, $R_{11b}$, $R_{12a}$, $R_{12b}$, $R_{13a}$, $R_{13b}$, $R_{14a}$, and $R_{14b}$;
$R_{6a}$ and $R_{6b}$ are independently selected from the group consisting of H, $OR_8$, aryl, and heteroaryl; or $R_{6a}$ and $R_{6b}$ taken together are —$CH_2CH_2$—;
$R_{7a}$ and $R_{7b}$ are independently selected from the group consisting of H, $C_{1-8}$, aryl, and heteroaryl; or $R_{7a}$ and $R_{7b}$ taken together are —$CH_2CH_2$—;
$R_8$ is selected from the group consisting of H, $C_{1-8}$alkyl, $C_{2-8}$ alkenyl, $C_{2-8}$ alkynyl, perhaloalkyl (preferably $CF_3$), $C_{1-8}$ alkyl-O—$C_{1-8}$ alkyl, aryl, heteroaryl, $C_{1-8}$ alkyl-O-aryl, $C_{1-8}$ alkyl-O-heteroaryl, $C_{1-8}$ alkylaryl, and $C_{1-8}$ alkylheteroaryl;
$R_9$ is selected from the group consisting of H, $C_{1-8}$alkyl, $C_{2-8}$ alkenyl, $C_{2-8}$ alkynyl, perhaloalkyl (preferably $CF_3$), $C_{1-8}$ alkyl-O—$C_{1-8}$ alkyl, aryl, heteroaryl, $C_{1-8}$ alkyl-O-aryl, $C_{1-8}$ alkyl-O-heteroaryl, $C_{1-8}$ alkylaryl, and $C_{1-8}$ alkylheteroaryl;
$R_{10}$ is selected from the group consisting of $C_{1-8}$ alkyl, $C_{2-8}$ alkenyl, $C_{2-8}$ alkynyl, perhaloalkyl (preferably $CF_3$), $C_{1-8}$ alkyl-O—$C_{1-8}$ alkyl, aryl, heteroaryl, $C_{1-8}$ alkyl-O-aryl, $C_{1-8}$ alkyl-O-heteroaryl, $C_{1-8}$ alkylaryl, and $C_{1-8}$ alkylheteroaryl;
$R_{11a}$ and $R_{11b}$ are independently selected from the group consisting of H, halogen, $C_{1-8}$ alkyl, perhaloalkyl (preferably $CF_3$), aryl, and heteroaryl;
$R_{12a}$ and $R_{12b}$ are independently selected from the group consisting of H, halogen, $C_{1-8}$ alkyl, perhalo alkyl (preferably $CF_3$), aryl, and heteroaryl, with the proviso that when the formula is

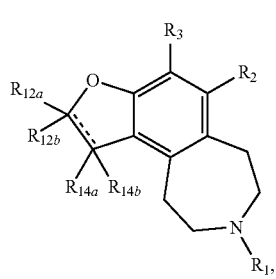

then $R_{12b}$ is not present;
$R_{13a}$ and $R_{13b}$ are independently selected from the group consisting of H, halogen, $C_{1-8}$ alkyl, perhaloalkyl (preferably $CF_3$), aryl, and heteroaryl;
$R_{14a}$ and $R_{14b}$ are independently selected from the group consisting of H, halogen, $C_{1-8}$ alkyl, $C_{2-8}$ alkenyl, $C_{2-8}$ alkynyl, perhaloalkyl (preferably $CF_3$), CN, $OR_8$, $NR_8R_9$, $SR_8$, $OCOR_{10}$, $OCONR_8R_9$, $CONR_8R_9$, $NR_8COR_{10}$, $NR_8CO_2R_{10}$, $NR_8SO_2R_{10}$, aryl, heteroaryl, $C_{1-8}$ alkylaryl, and $C_{1-8}$ alkylheteroaryl, with the proviso that when the formula is

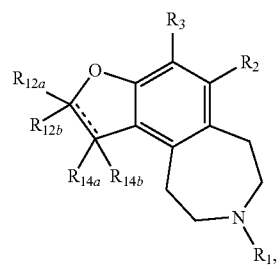

then $R_{14b}$ is not present;

In another embodiment, the compounds of the invention have the formula:

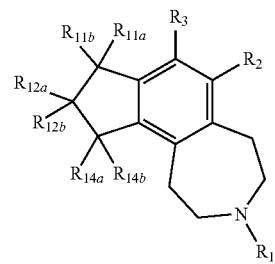

In one embodiment, the invention provides a compound wherein $R_1$, $R_2$, $R_3$, $R_{6a}$, $R_{6b}$, $R_{7a}$, $R_{7b}$ are H; and $R_4$ and $R_5$ together with the atoms which they are attached form a 5-membered carbocycle ring, substituted with one or more of each of $R_{11a}$, $R_{11b}$, $R_{12a}$, $R_{12b}$, $R_{14a}$, and $R_{14b}$.

In one embodiment, $R_{11a}$ and $R_{11b}$ are both H.

In another embodiment, $R_{12a}$ and $R_{12b}$ are both F.

In another embodiment, $R_{14a}$ is aryl and $R_{14b}$ is H.

In another embodiment, the compounds of the invention have the formula:

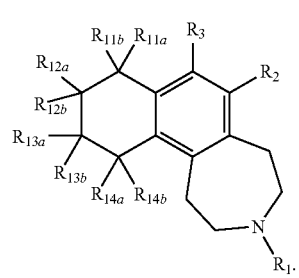

In another embodiment, the compounds of the invention have the formula:

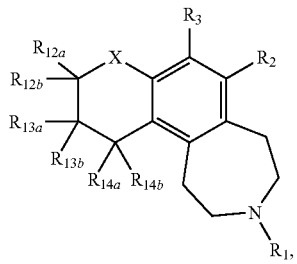

wherein X is C, S, SO₂ or O.

In another embodiment, the compounds of the invention have the formula:

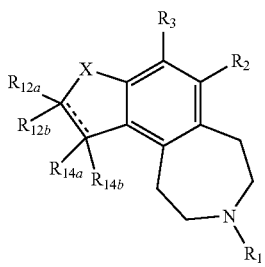

wherein X is C, S, SO₂ or O.

In a preferred embodiment, $R_1$ is H.

In one preferred embodiment, the invention provides a compound of one of the formulas:

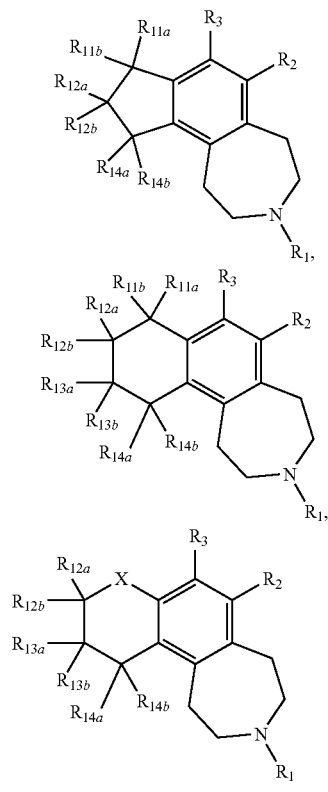

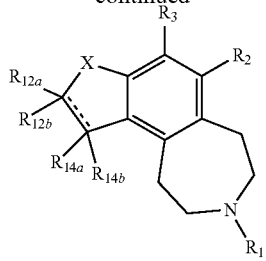

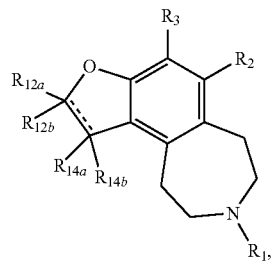

wherein
X is C, S, SO₂ or O;
$R_1$ is H;
$R_2$ and $R_3$ are independently selected from the group consisting of H and halogen;
$R_{11a}$, $R_{11b}$, $R_{12a}$, $R_{12b}$, $R_{13a}$ and $R_{13b}$ are independently selected from the group consisting of H and halogen; and
$R_{14a}$ and $R_{14b}$ are independently selected from the group consisting of H, halogen, $C_{1-8}$ alkyl, aryl, heteroaryl, $C_{1-8}$ alkylaryl, and $C_{1-8}$ alkylheteroaryl;
with the proviso that when the formula is then $R_{12b}$ and $R_{14b}$ are not present.

In some embodiments, the invention provides the following compounds:
1,2,3,6,7,8,9,10-octahydro-8-aza-cyclohepta[e]indene;
1-Methyl-1,2,3,6,7,8,9,10-octahydro-8-aza-cyclohepta[e]indene;
1-Ethyl-1,2,3,6,7,8,9,10-octahydro-8-aza-cyclohepta[e]indene;
1-Cyclopropyl-1,2,3,6,7,8,9,10-octahydro-8-aza-cyclohepta[e]indene;
1-Propyl-1,2,3,6,7,8,9,10-octahydro-8-aza-cyclohepta[e]indene;
4-Chloro-1-ethyl-1,2,3,6,7,8,9,10-octahydro-8-aza-cyclohepta[e]indene;
1-Ethyl-4-iodo-1,2,3,6,7,8,9,10-octahydro-8-aza-cyclohepta[e]indene;
1-Ethyl-4-fluoro-1,2,3,6,7,8,9,10-octahydro-8-aza-cyclohepta[e]indene;
1-Phenyl-1,2,3,6,7,8,9,10-octahydro-8-aza-cyclohepta[e]indene;
4-Chloro-1-phenyl-1,2,3,6,7,8,9,10-octahydro-8-aza-cyclohepta[e]indene;
1-Pyridin-3-yl-1,2,3,6,7,8,9,10-octahydro-8-aza-cyclohepta[e]indene;
4-Fluoro-1-pyridin-3-yl-1,2,3,6,7,8,9,10-octahydro-8-aza-cyclohepta[e]indene;
1,1-Dimethyl-1,2,3,6,7,8,9,10-octahydro-8-aza-cyclohepta[e]indene;
2,2-Difluoro-1-phenyl-1,2,3,6,7,8,9,10-octahydro-8-aza-cyclohepta[e]indene;

2,2-Difluoro-1-o-tolyl-1,2,3,6,7,8,9,10-octahydro-8-aza-cyclohepta[e]indene;
2,2-Difluoro-1-m-tolyl-1,2,3,6,7,8,9,10-octahydro-8-aza-cyclohepta[e]indene;
2,2-Difluoro-1-p-tolyl-1,2,3,6,7,8,9,10-octahydro-8-aza-cyclohepta[e]indene;
2,2-Difluoro-1-(3-trifluoromethyl-phenyl)-1,2,3,6,7,8,9,10-octahydro-8-aza-cyclohepta[e]indene;
2,2-Difluoro-1-(3-trifluoromethoxy-phenyl)-1,2,3,6,7,8,9,10-octahydro-8-aza-cyclohepta[e]indene;
2,2-Difluoro-1-(4-fluoro-phenyl)-1,2,3,6,7,8,9,10-octahydro-8-aza-cyclohepta[e]indene;
2,2-Difluoro-1-(3-fluoro-phenyl)-1,2,3,6,7,8,9,10-octahydro-8-aza-cyclohepta[e]indene;
1-Cyclopropyl-2,2-difluoro-1,2,3,6,7,8,9,10-octahydro-8-aza-cyclohepta[e]indene;
1-(3-Chloro-phenyl)-2,2-difluoro-1,2,3,6,7,8,9,10-octahydro-8-aza-cyclohepta[e]indene;
1-(4-Chloro-phenyl)-2,2-difluoro-1,2,3,6,7,8,9,10-octahydro-8-aza-cyclohepta[e]indene;
2,2-Difluoro-1-(2-methoxy-phenyl)-1,2,3,6,7,8,9,10-octahydro-8-aza-cyclohepta[e]indene;
2,2-Difluoro-1-(3-methoxy-phenyl)-1,2,3,6,7,8,9,10-octahydro-8-aza-cyclohepta[e]indene;
2,2-Difluoro-1-(4-methoxy-phenyl)-1,2,3,6,7,8,9,10-octahydro-8-aza-cyclohepta[e]indene;
2,2-Difluoro-1-pyridin-3-yl-1,2,3,6,7,8,9,10-octahydro-8-aza-cyclohepta[e]indene;
2,2-Difluoro-1-pyridin-4-yl-1,2,3,6,7,8,9,10-octahydro-8-aza-cyclohepta[e]indene;
4-Chloro-2,2-difluoro-1-pyridin-3-yl-1,2,3,6,7,8,9,10-octahydro-8-aza-cyclohepta[e]indene;
1-Ethyl-2,2-difluoro-1,2,3,6,7,8,9,10-octahydro-8-aza-cyclohepta[e]indene;
2,2-Difluoro-1-methyl-1,2,3,6,7,8,9,10-octahydro-8-aza-cyclohepta[e]indene;
1-Benzyl-2,2-difluoro-1,2,3,6,7,8,9,10-octahydro-8-aza-cyclohepta[e]indene;
2,2-Difluoro-1,1-dimethyl-1,2,3,6,7,8,9,10-octahydro-8-aza-cyclohepta[e]indene;
1,1-Dimethyl-4-phenyl-1,2,3,6,7,8,9,10-octahydro-8-aza-cyclohepta[e]indene;
1-Ethyl-1,2,7,8,9,10-hexahydro-6H-3-oxa-8-aza-cyclohepta[e]indene;
1-Ethyl-2,3,8,9,10,11-hexahydro-1H,7H-4-oxa-9-aza-cyclohepta[a]naphthalene;
2,2-Difluoro-1-methoxy-1,2,3,6,7,8,9,10-octahydro-8-aza-cyclohepta[e]indene;
1-Phenyl-7,8,9,10-tetrahydro-6H-3-oxa-8-aza-cyclohepta[e]indene;
1-Thiazol-2-yl-1,2,3,6,7,8,9,10-octahydro-8-aza-cyclohepta[e]indene;
1-Ethoxy-2,2-difluoro-1,2,3,6,7,8,9,10-octahydro-8-aza-cyclohepta[e]indene;
2,2-Difluoro-1,2,3,6,7,8,9,10-octahydro-8-aza-cyclohepta[e]indene; and
1-Methoxy-1,2,3,6,7,8,9,10-octahydro-8-aza-cyclohepta[e]indene.

Certain compounds of the invention may exist in different isomeric (e.g. enantiomers and distereoisomers) forms. The invention contemplates all such isomers both in pure form and in admixture, including racemic mixtures. Enol forms are also included.

The compounds of the invention can exist in unsolvated as well as solvated forms, including hydrated forms, e.g., hemi-hydrate. In general, the solvated forms, with pharmaceutically acceptable solvents such as water, ethanol, and the like are equivalent to the unsolvated forms for the purposes of the invention.

Certain compounds of the invention also form pharmaceutically acceptable salts, e.g., acid addition salts. For example, the nitrogen atoms may form salts with acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous hydroxide potassium carbonate, ammonia, and sodium bicarbonate. The free base forms differ from their respective salt forms somewhat in certain physical properties, such as solubility in polar solvents, but the acid salts are equivalent to their respective free base forms for purposes of the invention. (See, for example S. M. Berge, et al., "Pharmaceutical Salts," *J. Pharm. Sci.* 66: 1-19 (1977) which is incorporated herein by reference.

As used herein, the term "composition" is intended to encompass a product comprising the specified ingredients in the specified amounts, as well as any product which results, directly or indirectly, from a combination of the specified ingredients in the specified amounts.

The compounds of the present invention can be used in the form of pharmaceutically acceptable salts derived from inorganic or organic acids. The phrase "pharmaceutically acceptable salt" means those salts which are within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in J. *Pharmaceutical Sciences,* 1977, 66: 1 et seq. The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methyl ammonium, dimethylammonium, trimethylammonium, triethylammonium, diethylammonium, and ethylammonium among others. Other representative organic amines useful for the formation of base addition salts include ethylenediamine, ethanolamine, diethanolamine, piperidine, piperazine and the like.

Dosage forms for topical administration of a compound of this invention include powders, sprays, ointments and inhalants. The active compound is mixed under sterile conditions with a pharmaceutically acceptable carrier and any needed preservatives, buffers or propellants which can be required. Opthalmic formulations, eye ointments, powders and solutions are also contemplated as being within the scope of this invention.

Actual dosage levels of active ingredients in the pharmaceutical compositions of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the present invention can be employed in pure form or, where such forms exist, in pharmaceutically acceptable salt, ester or prodrug form. Alternatively, the compound can be administered as a pharmaceutical composition containing the compound of interest in combination with one or more pharmaceutically acceptable excipients. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal may range from about 0.0001 to about 1000 mg/kg/day. For purposes of oral administration, more preferable doses can be in the range of from about 0.001 to about 5 mg/kg/day. If desired, the effective daily dose can be divided into multiple doses for purposes of administration; consequently, single dose compositions may contain such amounts or submultiples thereof to make up the daily dose.

The present invention also provides pharmaceutical compositions that comprise compounds of the present invention formulated together with one or more non-toxic pharmaceutically acceptable carriers. The pharmaceutical compositions can be specially formulated for oral administration in solid or liquid form, for parenteral injection or for rectal administration.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous and intraarticular injection and infusion.

In another aspect, the present invention provides a pharmaceutical composition comprising a component of the present invention and a physiologically tolerable diluent. The present invention includes one or more compounds as described above formulated into compositions together with one or more non-toxic physiologically tolerable or acceptable diluents, carriers, adjuvants or vehicles that are collectively referred to herein as diluents, for parenteral injection, for intranasal delivery, for oral administration in solid or liquid form, for rectal or topical administration, among others.

The compositions can also be delivered through a catheter for local delivery at a target site, via an intracoronary stent (a tubular device composed of a fine wire mesh), or via a biodegradable polymer. The compounds may also be complexed to ligands, such as antibodies, for targeted delivery.

Compositions suitable for parenteral injection may comprise physiologically acceptable, sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water ethanol, polyols (propyleneglycol, polyethyleneglycol glycerol, and the like), vegetable oils (such as olive oil), injectable organic esters such as ethyl oleate, and suitable mixtures thereof.

These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., *Methods in Cell Biology*, Volume XIV, Academic Press, New York, N.Y. (1976), p. 33 et seq.

The term "pharmaceutically acceptable prodrugs" as used herein represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. Prodrugs of the present invention may be rapidly transformed in vivo to the parent compound of the above formula, for example, by hydrolysis in blood. A thorough discussion is provided in T. Higuchi and V. Stella, *Pro-drugs as Novel Delivery Systems*, V. 14 of the A.C.S. Symposium Series, and in Edward B. Roche, ed., *Bioreversible Carriers in Drug Design*, American Pharmaceutical Association and Pergamon Press (1987), hereby incorporated by reference.

Methods of Treatment

In another embodiment, the present invention provides a method of treating a disease, disorder and/or condition in a mammal (e.g., animal or human), wherein a $5\text{-HT}_{2c}$ receptor is implicated and modulation of a $5\text{-HT}_{2c}$ function is desired. The method comprises administering a therapeutically effective amount of a compound of the present invention, or a pharmaceutically acceptable salt thereof, to the mammal for the purposes of treating and/or preventing the disease, disorder and/or condition.

Yet another embodiment of the present invention comprises a method of modulating 5-HT receptor function with an effective amount of compound of the present invention, or a pharmaceutically acceptable salt thereof.

A further embodiment of the present invention provides a method of treating or preventing diseases, disorders, and/or conditions of the central nervous system (CNS). The method comprises administering a therapeutically effective amount of a compound of the present invention, or a pharmaceutically acceptable salt thereof, to the mammal.

In a preferred embodiment, the invention provides methods of treating and/or prevention of the following diseases, disorders and/or conditions in a mammal: obesity, psychiatric disorders (including but not limited to depression, schizophrenia, phobias, anxiety, panic disorders, obsessive compulsive disorder, and impulse control disorder); attention deficit disorder, addiction, sleep disorders (including but not limited to narcolepsy, sleep apnea, insomnia, disturbed biological and circadian rhythms, and hyper- and hyposomnolence), migraine, Type II diabetes, and epilepsy. It has been previously demonstrated that 5-$HT_{2C}$ receptors are implicated in these diseases.

Specifically, Grottick et al, *Studies to Investigate the Role of 5-$HT_{2C}$ Receptors on Cocaine-and Food-Maintained Behavior*, The Journal of Pharmacology and Experimental Therapeutics, Vol. 295, No. 3, pp. 1183-1191, 2000, demonstrate that activation of 5-$HT_{2C}$ receptor reduces both food- and cocaine-maintained behavior. Grottick et al, p. 1190, first column, last paragraph.

Higgins et al, *Serotonin and drug reward: focus on 5-$HT_{2C}$ receptors*, European Journal of Pharmacology 480 (2003): 151-162 (from hereon, Higgins et al) disclose that 5-$HT_{2C}$ receptors influence reward-related behavior. The authors discuss animal data which showed that 5-$HT_{2C}$ receptor knockout mice had an increased propensity to self-administer intravenous cocaine. Higgins et al, p. 157, second column, second paragraph. They also state that the "5-$HT_{2C}$ receptor may represent a possible therapeutic target for the development of selective agonists as treatments for aspects of drug abuse." Id., p. 158, second column, last paragraph.

Grauer et al, *WAY-163909, a 5-$HT_{2C}$ agonist, enhances the preclinical potency of current antipsychotics*, Psychopharmacology (2009) 204: 37-48 (from hereon, Grauer et al) teach that 5-$HT_{2C}$ agonists may enhance the potency of antipsychotic medications. Grauer et al, p. 37, Conclusion and p. 45, first column, second full paragraph.

Siuciak et al, *CP-809,101, a selective 5-$HT_{2C}$ agonist, shows activity in animal models of antipsychotic activity*, Neuropharmacology 52 (2007) 279-290 (from hereon, Siuciak et al) teach that 5-$HT_{2C}$ receptor agonists may be used in the treatment of, schizophrenia. Siuciak et al, Abstract.

Jason C G Halford, *Obesity drugs in clinical development*, Current Opinion in Investigational Drugs, 2006 7(4): 312-318 (from hereon, Harford) states that serotonin 5-$HT_{2C}$ receptor agonists have been shown to reduce food intake and body weight gain in rodents, and to reduce calorie intake, appetite, and body weight in humans. Halford, p. 313, second column, first full paragraph.

Likewise, Keith Miller, *Serotonin-5$HT_{2C}$ Receptor Agonists: Potential for the Treatment of Obesity*, Molecular Interventions, October 2005, Volume 5, Issue 5, pp. 283-291 (from hereon, Miller) shows that 5-$HT_{2C}$ receptor is a compelling target for the treatment of obesity. Miller, p. 288, Conclusion.

Methvin Isaac, *Serotonergic 5-$HT_{2C}$ Receptors as a Potential Therapeutic Target for the Design Antiepileptic Drugs*, Current Topics in Medicinal Chemistry 2005, 5, 59-67 (from hereon, Isaac) teaches that "[t]he 5-$HT_{2C}$ receptor subtype appears to be a rational target for the development of novel antiepileptic drugs." Isaac, p. 65, second column, second-to-last paragraph.

Martin et al, *5-$HT_{2C}$ Receptor Agonists: Pharmacological Characteristics and Therapeutic Potential*, The Journal of Pharmacology and Experimental Therapeutics, Vol. 286, No. 2, pp. 913-924 (from hereon, Martin et al) conducted several experiments and concluded that certain 5-$HT_{2C}$ receptor agonists demonstrated both their excellent tolerability and their therapeutic potential for obsessive compulsive disorder and depression. Martin et al, p. 923, last paragraph.

Zhou et al, *Serotonin 2C receptor agonists improve type 2 diabetes via melanocortin-4 receptor signaling pathways*, Cell Metab. 2007 November; 6(5) 398-405 (from hereon, Zhou et al) teach that 5-$HT_{2C}$ receptor agonists may improve glucose tolerance and reduce plasma insulin in murine models of obesity and type 2 diabetes. Zhou et al, Abstract.

All of the scientific publications, patent applications and patents cited in this specification are herein incorporated in their entirety by reference.

SCHEMES AND EXAMPLES

The compounds of the present invention may be prepared by the procedures set forth in Schemes 1 through 7.

List of Abbreviations:

The following abbreviations are used in the Schemes and Examples below.

| Abbreviation | Definition |
|---|---|
| AcOH | acetic acid |
| AIBN | azobisisobutryonitrile |
| $AlCl_3$ | aluminum trichloride |
| $AlMe_3$ | trimethylaluminum |
| Ar | argon |
| $BF_3OEt$ | boron trifluoride etherate |
| $Br_2$ | bromine |
| $Bu_3SnH$ | tributyltin hydride |
| n-BuLi | n-butyl lithium |
| CDI | carbonyldiimidazole |
| $CHCl_3$ | chloroform |
| DCE | dichloroethane |
| DCM | dichloromethane |
| DIEA | diisopropylethylamine |
| DMF | dimethylformamide |
| DMSO | dimethylsulfoxide |
| ECF | ethyl chloroformate |
| $Et_3SiH$ | triethylsilane |
| EtOAc | ethyl acetate |
| EtOH | ethanol |
| $H_2$ | hydrogen |
| $H_2SO_4$ | sulfuric acid |
| $H_3PO_2$ | hypophosphorous acid |
| HBr | hydrobromic acid |
| HCl | hydrochloric acid |
| $HNO_3$ | nitric acid |
| $K_2CO_3$ | potassium carbonate |
| KOAc | potassium acetate |
| KOH | potassium hydroxide |
| LHMDS | lithium bis(trimethylsilyl)amide |
| MeOH | methanol |
| $MgCl_2$ | magnesium chloride |
| $MgSO_4$ | magnesium sulfate |
| $Na_2CO_3$ | sodium carbonate |
| NaH | sodium hydride |
| $NaHCO_3$ | sodium bicarbonate |
| $NaNO_2$ | sodium nitrite |
| NaOH | sodium hydroxide |
| NBS | N-bromosuccinimide |
| $NH_4Cl$ | ammonium chloride |
| $NH_4OAc$ | ammonium acetate |
| $NH_4OH$ | ammonium hydroxide |
| $NiCl_2$ | nickel chloride |
| NIS | N-iodosuccinimide |
| Pd—C | palladium on carbon |
| $Pd(OH)_2$ | palladium hydroxide |
| rt | room temperature |
| $SOCl_2$ | thionyl chloride |
| TBDMS-triflate | tert-Butyldimethylsilyl trifluoromethanesulfonate |
| TEA | triethylamine |
| TFA | trifluoroacetic acid |
| TFAA | trifluoroacetic anhydride |
| THF | tetrahydrofuran |
| $TiCl_4$ | titanium tetrachloride |
| TMSI | iodotrimethylsilane |
| $Zn(Me)_2$ | dimethylzinc |

The general analytical conditions set forth below were utilized in all examples.

General Analytical/Instrumentation Information:
1. Reverse-phase HPLC analysis and purification was performed using a Waters 2525 binary gradient pump, Waters 2767 sample manager, waters 2487 UV detector (220 and 254 nM), Waters reagent manager (for prep runs), and Waters Micromass ZQ electrospray mass spec detector. The Micromass ZQ was set for both positive and negative ionization (cone voltage=25 and 50, respectively). Analytical HPLC analysis was performed as follows:
Waters XTerra MS C18 50×4.6 mm 3.5 μm column
Mobile Phase: 10 mM ammonium acetate buffer in water and methanol
Methanol: 10 to 75% at 3.5 minutes, 75 to 99% at 3.9 minutes, 99% hold to 4.2 minutes, 99 to 10% at 4.5 minutes, re-equilibrate.
Flow rate—2.25 ml/min
Preparative HPLC was performed as follows:
Waters XTerra Prep MS C18 100×19 mm 5 μm column
Mobile Phase: 10 mM ammonium acetate buffer in water and methanol Methanol: 10 to 99% at 16 minutes, 99% hold to 18 minutes, 99 to 10% at 19 minutes, re-equilibrate
Flow rate—24 ml/min
Preparative Chiral HPLC was performed as follows:
Chiral Technologies, ChiralPak AD-RH 20×250 mm 5 μm column
Mobile phase: 0 to 20% water in methanol (no buffer), Isocratic
Flow rate—varied depending on percentage of water (7-10 ml/min)
2. Normal-phase preparative chiral HPLC purification was performed using a Waters Delta 600 extended flow quaternary gradient pump with a Water 600 Controller, Waters 2487 UV detector (215 and 280 nM), Waters 2707 Autosampler, and a Waters Fraction Collector II. Preparative normal phase HPLC was performed as follows:
Chiral Technologies, ChiralPak AD-H 30×250 mm, 5 μm column
Mobile Phase: 1%-30% ethanol in hexane, Isocratic
Flow Rate: 30 ml/min
3. NMR analysis was performed using a Bruker BioSpin UltraSheild NMR (300 MHz).
4. Microwave Synthesis: Biotage Initiator
5. Flash silica-gel chromatography: Teledyne Isco Combi-Flash $R_f$
6. Parr Hydrogenation Apparatus w/Parr 4833 temperature controller Schemes Scheme 1. Synthesis of 4-Iodo-1-oxo-1,3,6,7,9,10-hexahydro-2H-8-aza-cyclohepta[e]indene-8-carboxylic acid ethyl ester (Intermediate 1)

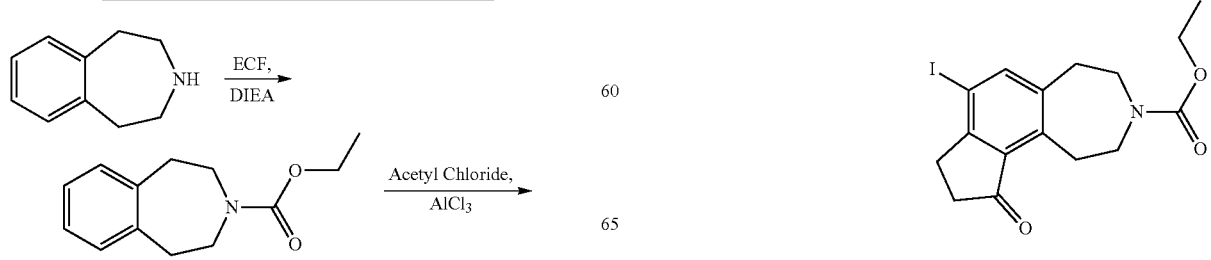

Intermediate 1. 4-Iodo-1-oxo-1,3,6,7,9,10-hexahydro-2H-8-aza-cyclohepta[e]indene-8-carboxylic acid ethyl ester

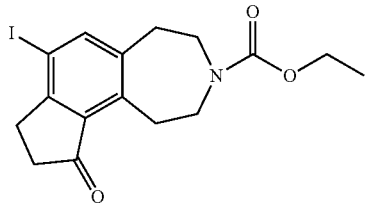 [SMILES: CCOC(=O)N1CCc2cc(I)c3c(c2CC1)C(=O)CC3]

a) 1,2,4,5-Tetrahydro-benzo[d]azepine-3-carboxylic acid ethyl ester

To a stirred solution of benzazepine hydrochloride (5.0 g, 27.2 mmol) in DCM (~50 ml) diisopropyl ethylamine (10.4 ml, 59.8 mmol) was added at 0° C., followed by dropwise addition of ethyl chloroformate (2.86 ml, 29.9 mmol). The reaction was stirred at 0° C. for 1 hour and then allowed to warm to room temperature over 2 hours. LCMS indicated reaction was complete, and 1N HCl (~100 ml) was added to the reaction. The layers were separated and the aqueous layer was extracted with additional DCM (2×). The combined DCM extracts were washed with brine and dried over Na$_2$SO$_4$. The solvent was evaporated in vacuo and the residue purified by silica-gel chromatography (gradient elution: 0 to 40% EtOAc in hexanes) to provide the sub-title product as an oil (5.5 g). $^1$HNMR (CDCl$_3$) δ 7.14 (s, 4H), 4.18 (q, J=7.2 Hz, 2H), 3.61 (bs, 4H), 2.92 (bs, 4H), 1.29 (t, J=7.2 Hz, 3H); MS: ESI (positive): 220 (M+H).

b) 7-Acetyl-1,2,4,5-tetrahydro-benzo[d]azepine-3-carboxylic acid ethyl ester To a stirred solution of the product from step (a) (5 g, 22.8 mmol) in DCM (~100 ml), acetyl chloride (8.2 ml, 114 mmol) was added at room temperature, followed by aluminum chloride (9.1 g, 68.4 mmol). The reaction was stirred for 2 hours (LCMS indicated reaction was complete) and then quenched by pouring the reaction contents into an iced stirred saturated NaHCO$_3$ solution. When the gas evolution ceased and the mixture came to room temperature, the aqueous mixture was placed in a separatory funnel, and the layers separated. The aqueous layer was extracted two additional times with fresh DCM. The DCM extracts were combined and washed with water and brine solution. The DCM extracts were dried over MgSO$_4$ and filtered. The solvent was evaporated in vacuo to give the sub-title product as a colorless oil (5.8 g). $^1$HNMR (CDCl$_3$) δ 7.74-7.71 (m, 2H), 7.23-7.20 (m, 1H), 4.19 (q, J=7.2 Hz, 2H), 3.62 (bs, 4H), 2.98 (bs, 4H), 2.59 (s, 3H); 1.29 (t, J=7.2 Hz, 3H); MS: ESI (positive): 262 (M+H).

c) 1,2,4,5-Tetrahydro-benzo[d]azepine-3,7-dicarboxylic acid 3-ethyl ester

To a stirred solution of the product from step (b) (5.8 g, 22.2 mmol) in dioxane (~45 ml), 4M NaOH (44.4 ml, 177.6 mmol) was added at room temperature. The reaction mixture was cooled to 0° C., followed by dropwise addition of bromine (3.42 ml, 66.6 mmol). The reaction was stirred at 0° C. for 2 hours (LCMS indicated reaction was complete) and then quenched by addition of acetone (~50 ml). The reaction mixture was allowed to warm to room temperature and the volatile organics were then evaporated in vacuo. The remaining aqueous mixture was diluted with water (~50 ml) and washed with diethyl ether (2×) to remove impurities. The pH of the aqueous mixture was adjusted to 2-3 by addition of 6N HCl. The acidic aqueous mixture was then extracted with fresh ethyl acetate (3×). The combined ethyl acetate extracts were washed with brine, dried (MgSO$_4$), and filtered. The solvent was evaporated in vacuo to give the sub-title product as a white solid (5.4 g). $^1$HNMR (CDCl$_3$) δ 7.90-7.87 (m, 2H), 7.23 (d, J=8.1 Hz, 1H), 4.20 (q, J=7.2 Hz, 2H), 3.63 (bs, 4H), 2.99 (bs, 4H), 2.59 (s, 3H), 1.30 (t, J=7.2 Hz, 3H); MS: ESI (positive): 264 (M+H), ESI (negative): 262 (M−1).

d) 7-(2-Ethoxycarbonyl-acetyl)-1,2,4,5-tetrahydro-benzo[d]azepine-3-carboxylic acid ethyl ester Solution A:

To a stirred solution of the product from step (c) (5.4 g, 20.5 mmol) in anhydrous THF (~40 ml), carbonyldiimidazole (3.33 g, 20.5 mmol) was added at room temperature under Ar. The reaction mixture was stirred at room temperature under Ar overnight.

Solution B:

To a suspension of ethyl potassium malonate (6.98 g, 41.0 mmol) in anhydrous acetonitrile (~100 ml) and diisopropylethylamine (10.7 ml, 61.5 mmol), portion-wise MgCl$_2$ (4.69 g, 49.2 mmol) was added, while maintaining the temperature below 20° C. (in an ice bath). When the addition of MgCl$_2$ was complete, the reaction mixture was allowed to warm to room temperature. The mixture was stirred at room temperature for 4 hours.

Solution B was cooled to 0° C. Solution A was added to Solution B dropwise while stirring at 0° C. After the addition of Solution A was complete, the reaction mixture was allowed to warm to room temperature and stirred overnight (LCMS indicates a complete reaction). The solvent was evaporated in vacuo and the residue taken up in toluene (~100 ml). The mixture was cooled in an ice bath and 2N HCl (~50 ml) was slowly added. The reaction was then allowed to warm to room temperature and extracted with ethyl acetate (3×). The combined ethyl acetate extracts were washed with brine, dried (MgSO$_4$), filtered, and solvent evaporated in vacuo to give a colorless oil. The crude oil was purified by flash silica-gel chromatography (gradient elution: 0% to 50% EtOAc in hexanes) to give the sub-title product as a colorless oil (6.2 g). $^1$HNMR (CDCl$_3$) δ 7.84-7.23 (m, 3H), 4.27-4.16 (m, 4H), 3.98 (s, 1H), 3.62 (bs, 3H), 3.42 (s, 1H), 2.99 (bs, 3H), 1.35-1.23 (m, 6H); MS: ESI (positive): 334 (M+H).

e.) 7-(2-Ethoxycarbonyl-ethyl)-1,2,4,5-tetrahydro-benzo[d]azepine-3-carboxylic acid ethyl ester To a solution of the product from step (d) in ethanol (~100 ml), Pd—C (~1 g) 10% was added over an Ar atmosphere. The mixture was shaken in a Parr hydrogenation apparatus under 50 psi hydrogen at 50° C. When the reaction was deemed complete by LCMS (usually within 18 h), the reaction mixture was filtered through celite and the solvent evaporated in vacuo to give a yellow oil that solidified on standing. The crude product was purified by silica-gel chromatography (gradient elution: 0% to 40% EtOAc in hexanes) to give the sub-title product as a white solid (5.8 g). $^1$HNMR (CDCl$_3$) δ 7.05-6.95 (m, 3H), 4.21-4.09 (m, 4H), 3.57 (bs, 4H) 2.92-2.87 (m, 6H), 2.59 (t, J=8.1 Hz, 2H), 1.31-1.21 (m 6H); MS: ESI (positive): 320 (M+H).

f) 7-(2-Ethoxycarbonyl-ethyl)-8-iodo-1,2,4,5-tetrahydro-benzo[d]azepine-3-carboxylic acid ethyl ester To a stirred solution of the product from step (e) (1.4 g, 4.3 mmol) in trifluoroacetic acid (2 ml) and chloroform (8 ml), N-Iodosuccinimide (0.97 g, 4.3 mmol) was added at room temperature. The reaction mixture was stirred at room temperature for 16 hours and poured over ice. The aqueous mixture was extracted with dichloromethane (3×). The combined DCM extracts were washed with brine, dried under $Na_2SO_4$, and solvent evaporated in vacuo to give the crude product. Purification by silica-gel chromatography (gradient elution: 0 to 100% EtOAc in hexanes) gave the sub-title product (1.80 g). $^1$HNMR (CDCl$_3$) δ 7.56 (s, 1H), 6.99 (s, 1H), 4.21-4.10 (m, 4H), 3.57 (bs, 4H), 2.98 (t, J=7.5 Hz, 2H), 2.81 (bs, 4H), 2.59 (t, J=7.5 Hz, 2H), 1.31-1.21 (m, 6H); MS: ESI (positive): 446 (M+H).

g) 7-(2-Carboxy-ethyl)-8-iodo-1,2,4,5-tetrahydro-benzo[d]azepine-3-carboxylic acid ethyl ester To a stirred solution of the product from step (f) (1.8 g, 4.0 mmol) in methanol (50 ml), sodium hydroxide solution (4N, 15 ml) was added. The reaction mixture was stirred at room temperature for 16 hours. The methanol was removed under vacuum and the aqueous layer was washed with diethyl ether. The aqueous layer was acidified to pH=2 with 6N HCl and extracted with DCM (3×). The combined DCM extracts were dried under $Na_2SO_4$ and the solvent evaporated in vacuo to provide the sub-title product which was used without further purification. $^1$HNMR (DMSO-d6) δ 7.59 (s, 1H), 7.08 (s, 1H), 4.06 (q, J=6.9 Hz, 2H), 3.45 (bs, 4H), 2.77 (bs, 6H), 2.39 (t, J=7.5 Hz, 2H), 1.19 (t, J=6.9 Hz, 3H); MS: ESI (positive): 418 (M+H), ESI (negative): 416 (M−1).

h) 4-Iodo-1-oxo-1,3,6,7,9,10-hexahydro-2H-8-aza-cyclohepta[e]indene-8-carboxylic acid ethyl ester To a stirred solution of the product from step (g) (0.4980 g, 1.2 mmol) in dichloromethane (10 ml), 1 drop of DMF was added at 0° C., followed by oxalyl chloride (1 ml, 12 mmol). The reaction mixture was stirred at 0° C. for ten minutes, then at room temperature for 1 hour. The reaction mixture was concentrated in vacuo and dissolved in fresh DCM (20 ml). The solution was cooled to 0° C., followed by the addition of aluminum chloride (0.48 g, 3.6 mmol). The reaction mixture was stirred at 0° C. for 30 minutes and then quenched by the addition of ice water (50 ml). The reaction mixture was extracted with DCM (3×). The combined DCM extracts were washed with brine, dried over $Na_2SO_4$, and the solvent evaporated in vacuo to give the crude product. Purification silica-gel chromatography (gradient elution: 0 to 100% EtOAc in hexanes) gave title product as a white solid (0.37 g). $^1$HNMR (DMSO-d6) δ 7.89 (s, 1H), 4.02 (q, J=6.9 Hz, 2H), 3.48 (s, 6H), 2.93 (bs, 2H), 2.78-2.76 (m, 2H), 2.68-2.64 (m, 2H), 1.15 (t, J=6.9 Hz, 3H); MS: ESI (positive): 400 (M+H).

Intermediate 2. 4-Bromo-1-oxo-1,3,6,7,9,10-hexahydro-2H-8-aza-cyclohepta Eel indene-8-carboxylic acid ethyl ester

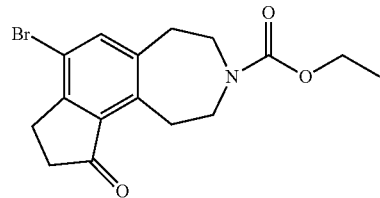 [SMILES: CCOC(=O)N1CCc2cc(Br)c3c(c2CC1)C(=O)CC3]

Intermediate 2 was prepared in a similar fashion to Intermediate 1 except NBS was used in the halogenation (Example 1, step (f)). $^1$HNMR (Acetone-d6) δ 7.61 (s, 1H), 4.08 (q, J=6.9 Hz, 2H), 3.58-3.51 (m, 6H), 3.01-2.97 (m, 2H), 2.94-2.90 (m, 2H), 2.68-2.64 (m, 2H), 1.21 (t, J=6.9 Hz, 3H); MS: ESI (positive): 352, 354 (M+H).

Scheme 2. Synthesis of other 1-oxo-1,3,6,7,9,10-hexahydro-2H-8-aza-cyclohepta[e]indene-8-carboxylic acid ethyl ester intermediates

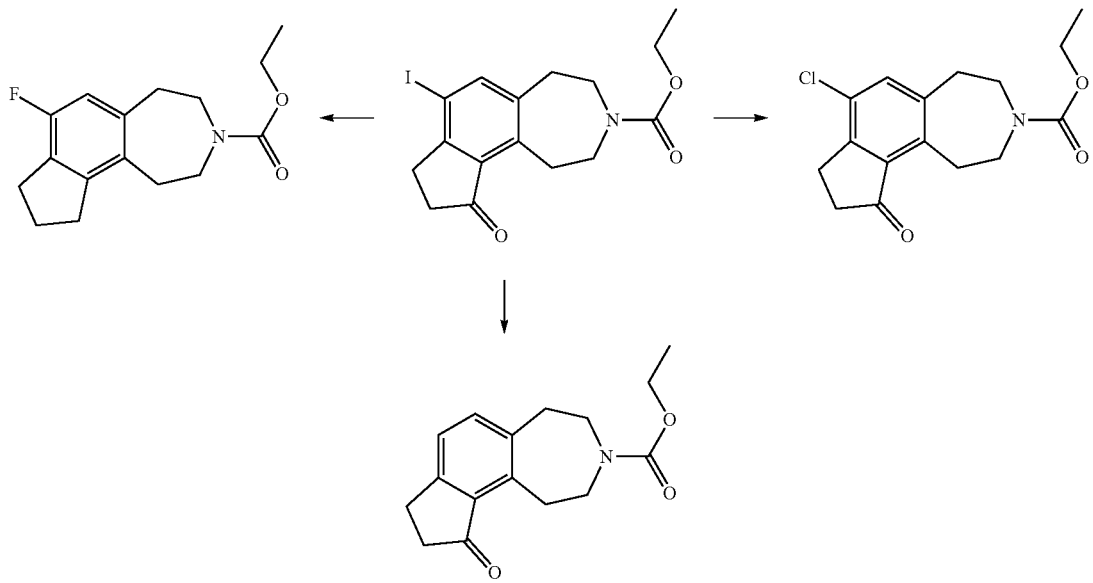

Intermediate 3. 1-Oxo-1,3,6,7,9,10-hexahydro-2H-8-aza-cyclohepta[e]indene-8-carboxylic acid ethyl ester

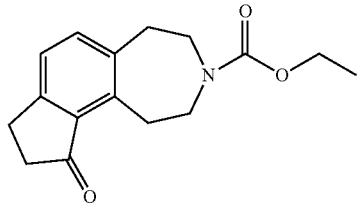 [SMILES: CCOC(=O)N1CCc2ccc3c(c2CC1)C(=O)CC3]

Into a 500 ml Parr bottle, Intermediate 1 (11 g, 27.56 mmol) was added, followed by 5% Pd—C (700 mg) in EtOH (200 ml). The mixture was shaken over 50 psi hydrogen for 16 hours. The contents were filtered through celite and solvent evaporated in vacuo. The remaining residue was purified by silica-gel chromatography (gradient elution: 0 to 40% EtOAc in hexane) to give the title product as a white solid (6.1 g). $^1$H NMR (300 MHz, CDCl$_3$) δ 7.31 (d, J=7.8 Hz, 1H); 7.22 (d, J=7.8 Hz, 1H); 4.16 (q, J=6.9 Hz, 2H); 3.62-3.60 (m, 6 μl); 3.05-2.96 (m, 4 μl); 2.70-2.66 (m, 2H); 1.27 (t, J=6.9 Hz, 3H); MS: ESI (positive): 274 (M+H).

Intermediate 4. 4-Chloro-1-oxo-1,3,6,7,9,10-hexahydro-2H-8-aza-cyclohepta[e]indene-8-carboxylic acid ethyl ester

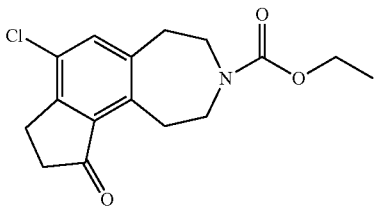 [SMILES: CCOC(=O)N1CCc2cc(Cl)c3c(c2CC1)C(=O)CC3]

Into a microwave vial, Intermediate 1 (250 mg, 0.626 mmol) was added in DMF (3 ml). To this solution was added NiCl$_2$ (406 mg, 3.13 mmol). The reaction mixture was heated in the microwave to 180° C. for 30 minutes. After the reaction mixture cooled, the reaction was diluted with water (75 ml). The aqueous mixture was extracted with DCM (3×). The combined DCM extracts were washed with brine, dried over Na$_2$SO$_4$, and solvent evaporated in vacuo to give the crude product. Purification by silica-gel chromatography (gradient elution: 0 to 30% EtOAc in hexanes) gave the title product as a colorless oil (159 mg). $^1$H NMR (300 MHz, CDCl3) δ 7.33 (s, 1H); 4.15 (q, J=6.9 Hz, 2H); 3.61-3.59 (m, 6H); 3.03-2.93 (m, 4H); 2.74-2.70 (m, 2H); 1.26 (t, J=6.9 Hz, 3H); MS: ESI (positive): 308, (M+H).

Intermediate 5. 4-Fluoro-1-oxo-1,3,6,7,9,10-hexahydro-2H-8-aza-cyclohepta[e]indene-8-carboxylic acid ethyl ester

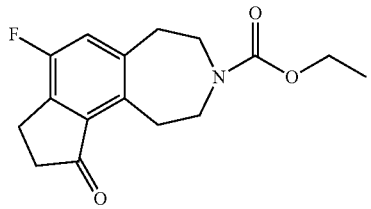

a) 1-Oxo-4-(4,4,5,5-tetramethyl-[1,3,2]dioxaborolan-2-yl)-1,3,6,7,9,10-hexahydro-2H-8-aza-cyclohepta[e]indene-8-carboxylic acid ethyl ester Into a microwave vial, Intermediate 1 (2 g, 5.01 mmol) in DMSO (15 ml) was added. To this solution, bis(pinacolato)diboron (1.91 g, 7.51 mmol), KOAc (1.23 g, 12.52 mmol), and Pd(dppf)C$_{12}$-DCM complex (409 mg, 0.501 mmol) were added. The vial was heated in the microwave to 120° C. for 30 minutes and then allowed to cool to room temperature. The reaction mixture was filtered through celite and diluted with saturated aqueous NaHCO$_3$ (200 ml). The aqueous mixture was extracted with DCM (3×). The combined DCM extracts were washed with brine, dried over Na$_2$SO$_4$, and solvent evaporated in vacuo to give the crude product. Purification by silica-gel chromatography (gradient elution: 0 to 20% EtOAc in hexanes) gave the sub-titled product as a white semisolid (1.58 g). $^1$H NMR (300 MHz, CDCl$_3$) δ 7.35 (s, 1H); 4.16 (q, J=7.2 Hz, 2H); 3.67-3.65 (m, 2H); 3.60-3.58 (m, 2H); 3.25-3.20 (m, 2H); 2.98 (br s, 2H); 2.67-2.63 (m, 2H); 1.35 (s, 12H); 1.29-1.23 (m, 3H); MS: ESI (positive): 400, (M+H).

b) 4-Boronic acid-1-oxo-1,3,6,7,9,10-hexahydro-2H-8-aza-cyclohepta[e]indene-8-carboxylic acid ethyl ester Into a 250 ml flask, the product from step (a) (1.58 g, 3.95 mmol) in acetone (20 ml) and water (20 ml) was added. NH$_4$OAc (1.52 g, 77.08 mmol) was then added, followed by sodium periodate (3.37 g, 15.8 mmol). After stirring at room temperature for 48 hours, the mixture was partitioned between equal parts water and DCM, producing a cloudy mixture. The cloudy mixture was filtered through celite and the product, which remained on the celite pad, was washed through with MeOH. Evaporation of MeOH in vacuo gave the sub-title product as a white solid (604 mg) that was used without purification. MS: ESI (positive): 318, (M+H).

c) 4-Fluoro-1-oxo-1,3,6,7,9,10-hexahydro-2H-8-aza-cyclohepta[e]indene-8-carboxylic acid ethyl ester Into a 100 ml flask, the product from step (b) (404 mg, 1.27 mmol) and NaOH (61 mg, 1.52 mmol) in dry MeOH (10 ml) were added. After stirring for 15 minutes at room temperature, the reaction mixture was cooled to 0° C. and silver triflate (978 mg, 3.81 mmol) was added. After stirring for 30 minutes at 0° C., the volatiles were evaporated in vacuo at room temperature, and the residue re-dissolved in dry acetone (10 ml). To this solution, Selectfluor (472 mg, 1.33 mmol) was added and the mixture was stirred at room temperature for 30 minutes. The reaction mixture was filtered through celite and the solvent was evaporated in vacuo. The resulting residue was partitioned between water and DCM. The aqueous layer was extracted with DCM (3×). The combined DCM extracts were washed with brine, dried over Na$_2$SO$_4$, and solvent evaporated in vacuo to give the crude product. Purification by silica-gel chromatography (gradient elution: 0 to 20% EtOAc in hexanes) gave the title compound as a colorless oil (138 mg). $^1$H NMR (300 MHz, CDCl$_3$) δ 7.02 (d, J=9 Hz, 1H); 4.15 (q, 7.2 Hz, 2H); 3.62-3.57 (m, 6H); 3.04-3.00 (m, 2H); 2.96-2.93 (m, 2H); 2.73-2.69 (m, 2H); 1.26 (t, 6.9 Hz, 3H); MS: ESI (positive): 292, (M+H).

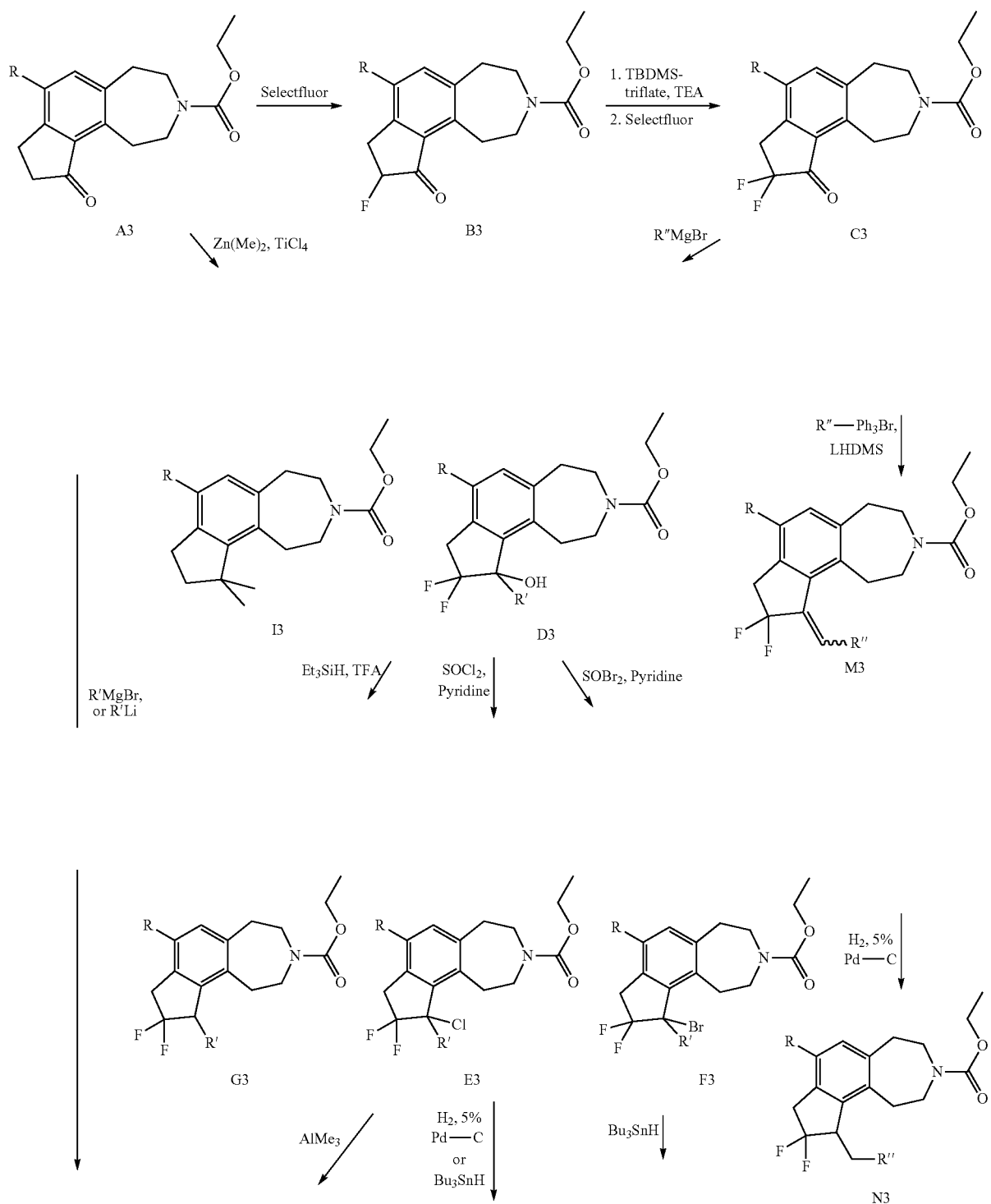

Scheme 3: Synthesis of various substituted 1,3,6,7,9,10-hexahydro-2H-8-aza-cyclohepta[e]indene-8-carboxylic acid ethyl esters

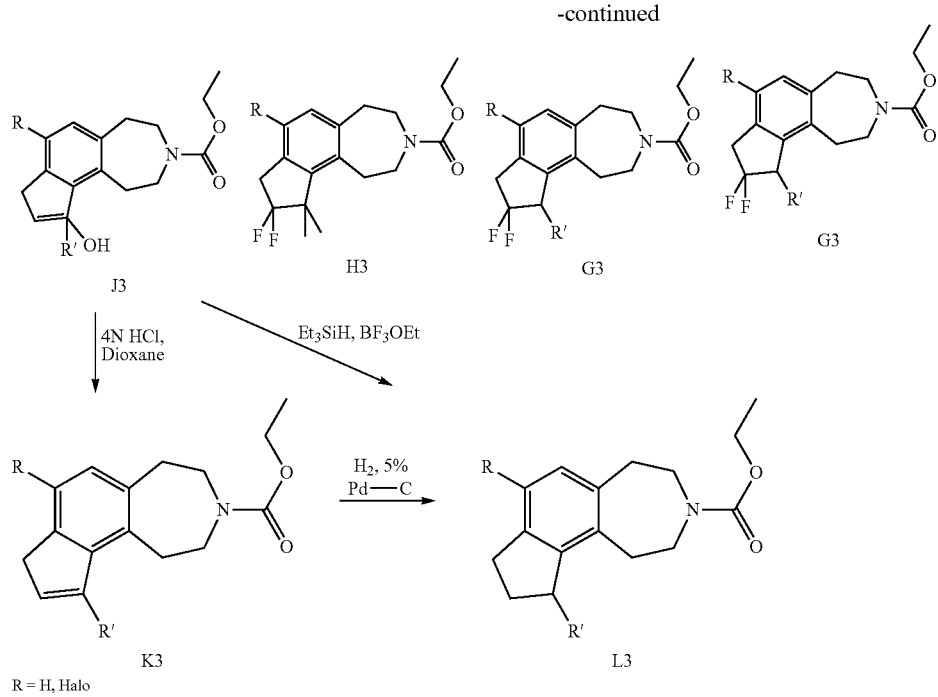

R = H, Halo

A compound of the general structure A3 (the synthesis of A3 is described above) can be difluorinated alpha to the carbocyclic ketone through a two step process. Treatment with selectfluor or other similar fluorinating reagents (e.g. accufluor) gives the mono-fluoro compound B3. The difluorinated compound can be prepared from the mono-fluoro compound by formation of a silyl enol-ether intermediate such as that derived from tert-butyldimethyl triflate and triethyl amine. Treatment of the transient enol ether with selectfluor gives compounds of the general structure C3. The compound of structure C3 can be treated with nucleophiles such as Grignard reagents or organolithium reagents to give tertiary alcohols of the general structure D3. Alcohols of structure D3 can be reduced directly with triethylsilane and an acid such as TFA or a Lewis acid such as boron trifluoride. Alternatively, some reductions require that the alcohol be converted to the chloride with thionyl chloride and pyridine or to the bromide with thionyl bromide and pyridine to give general structures E3 and F3, respectively. Compounds of general structure E3 can be reduced by hydrogenation with 5% Pd—C in an appropriate solvent or with tributyltin hydride in a suitable solvent to give compounds of the general structure G3. Bromide compounds of general structure F3 can be reduced with tributyltin hydride to give compounds G3. Gem-dimethyl structures of general structure H3 can be prepared from chloro-compound E3 by treatment with trimethyl aluminum in a suitable solvent such as cyclohexane.

Compounds of general structure C3 can also undergo Wittig-type olefination reactions with alkyl-triphenylphosphonium bromides and a base such as LHMDS or KtOBu in a suitable solvent such as THF to give alkenes of the general structure M3. The alkene compounds can be reduced by hydrogenation over Pd—C catalyst in an appropriate solvent to give compounds of the general structure N3.

Non-gem-difluoro compounds of general structure L3 can be prepared from the carbocyclic ketone A3 by nucleophilic addition of Grignard reagents or organolithium reagents to give tertiary alcohols of general structure J3. Alcohols of structure J3 can be reduced directly with triethylsilane and an acid such as TFA or a Lewis acid such as boron trifluoride to give compounds of general structure L3. Alternatively, the alcohol can be dehydrated in a solvent containing a mineral acid such as HCl in dioxane to give the alkene of general structure K3. The alkene K3 can then be reduced by hydrogenation with catalytic Pd—C in an appropriate solvent to give the compounds of general structure L3. Gem-dimethyl compounds of general structure I3 can also be prepared from A3 by treatment with dimethyl zinc and a Lewis acid such as titanium chloride.

Scheme 4: Synthesis of 1-(1-Substituted-1,2,6,7,9,10-hexahydro-3-oxa-8-aza-cyclohepta[e]inden-8-yl)-2,2,2-trifluoro-ethanone

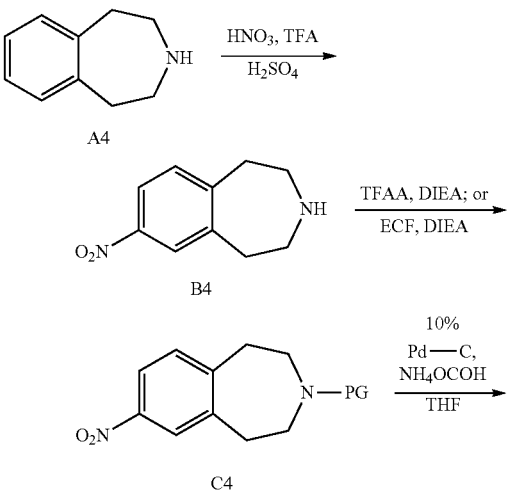

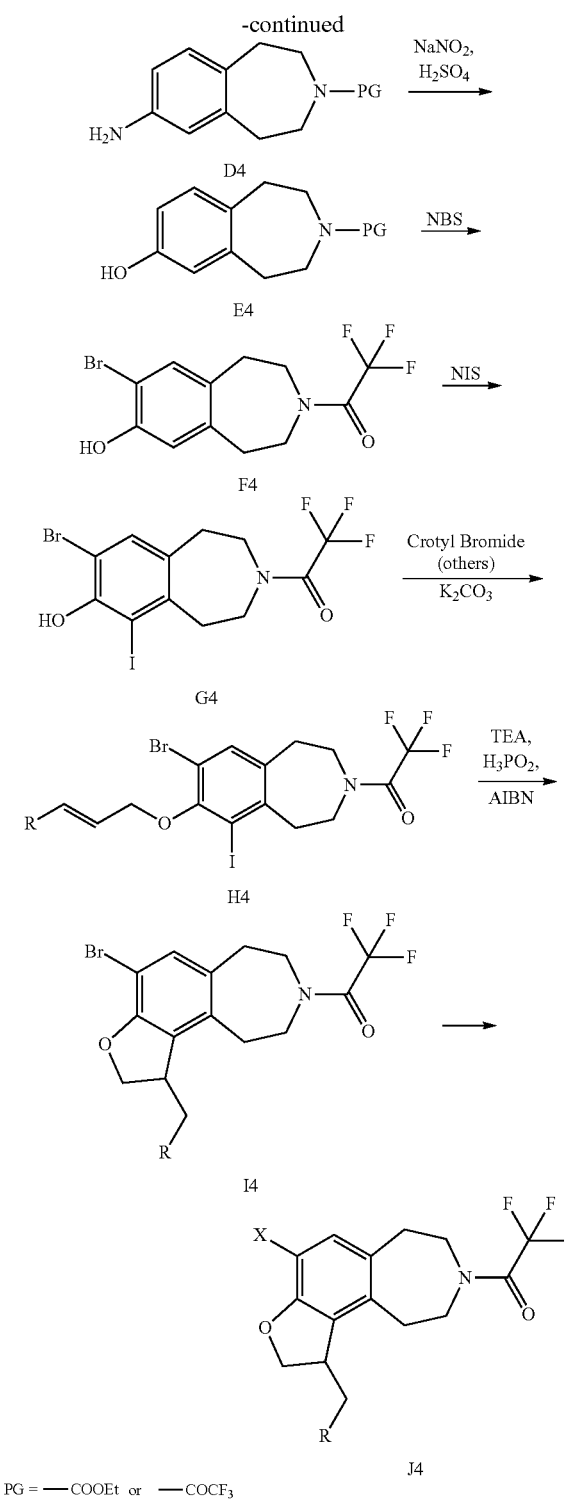

PG = —COOEt or —COCF₃ structure C4. The aryl nitro-group can be reduced using a variety of conditions including catalytic transfer hydrogenation to give aniline D4. The aniline can be converted to the general phenolic compound E4 by diazotization and hydrolysis with sodium nitrite in aqueous sulfuric acid. While the ethyl carbamate protected benzazepine will undergo this transformation, yields are generally lower than with the trifluoroacetamide protected amine presumably because of the greater stability of the trifluoroacetamide under the highly acidic reaction conditions. In an effort to selectively prepare the desired regioisomer of the final product, two halogenations steps can be used to impart regioselectivity during the cyclization step. The first halogenation involves bromination with N-bromosuccinimide to give predominately the desired isomer F4 which can then be subsequently iodinated with N-iodosuccinimide to give the compound G4. The phenol compound G4 can be alkylated with crotyl bromide or various analogs thereof and a base such as potassium carbonate in a suitable solvent such as acetone to give compounds of general structure H4. Selective radical cyclization onto the more reactive aryl iodide position can be achieved using AIBN as a radical initiator, hypophosphorous acid, and a tertiary amine base such as TEA in a suitable solvent such as methanol to give general structure I4. The aryl bromide I4 can be chemically manipulated further by methods (Suzuki reaction, Buchwald-Hartwig reaction, trans-halogenation, reduction, etc.) know to those skilled in the art to give various analogs of the general structure J4.

Scheme 5: Synthesis of various 2,2,2-Trifluoro-1-(1-substituted-6,7,9,10-tetrahydro-3-oxa-8-aza-cyclohepta[e]inden-8-yl)-ethanone or 1-(1-substituted-1,2,6,7,9,10-hexahydro-3-oxa-8-aza-cyclohepta[e]inden-8-yl)-2,2,2-trifluoro-ethanone

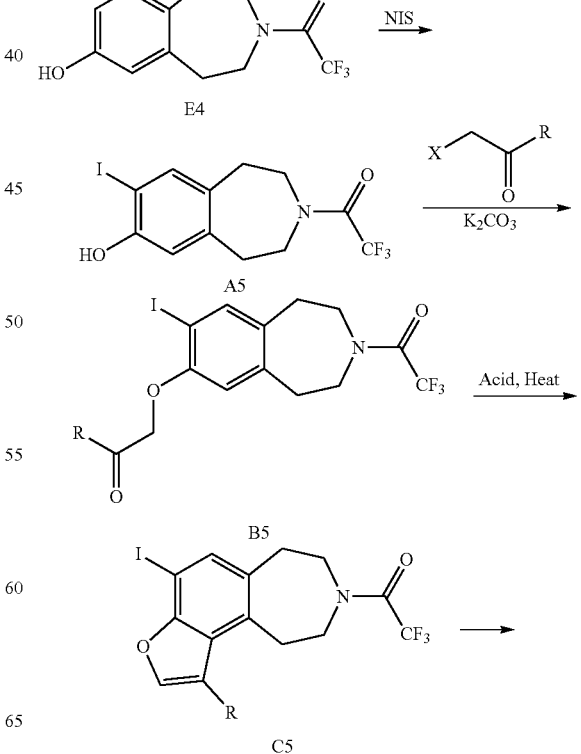

A compound with structure A4 can be nitrated under standard conditions using fuming nitric acid in sulfuric acid and trifluoroacetic acid to give compound B4. The basic amine of the nitrated benzazepine compound (B4) can be protected by a variety of groups that include ethylcarbamate and trifluoroacetamide. The latter two can be prepared by treatment of the basic amine with trifluoroacetic anhydride or ethyl chloroformate and a tertiary amine base such as Hünig's base in a suitable solvent such as dichloromethane to give the general

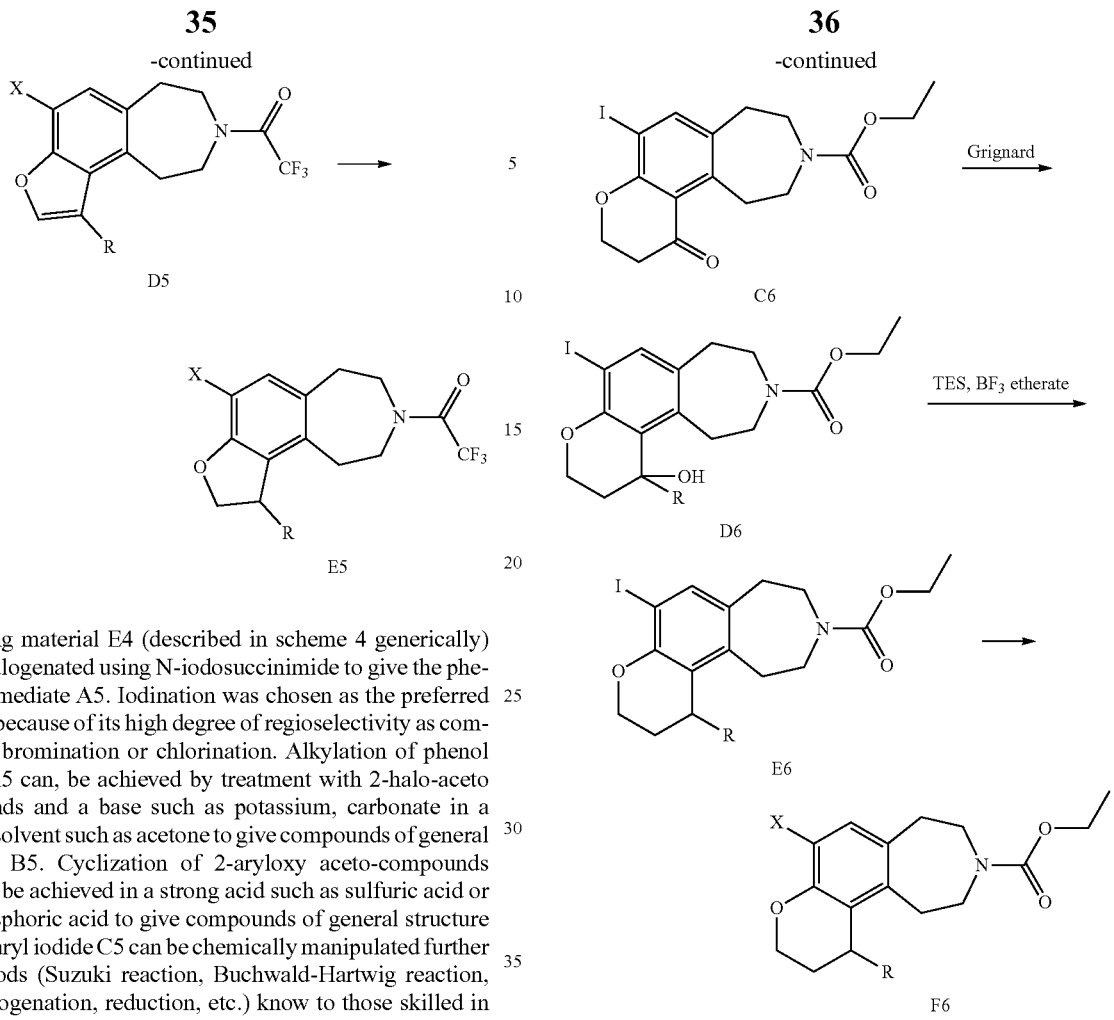

Starting material E4 (described in scheme 4 generically) can be halogenated using N-iodosuccinimide to give the phenol intermediate A5. Iodination was chosen as the preferred halogen because of its high degree of regioselectivity as compared to bromination or chlorination. Alkylation of phenol analog A5 can, be achieved by treatment with 2-halo-aceto compounds and a base such as potassium, carbonate in a suitable solvent such as acetone to give compounds of general structure B5. Cyclization of 2-aryloxy aceto-compounds (B5) can be achieved in a strong acid such as sulfuric acid or polyphosphoric acid to give compounds of general structure C5. The aryl iodide C5 can be chemically manipulated further by methods (Suzuki reaction, Buchwald-Hartwig reaction, trans-halogenation, reduction, etc.) know to those skilled in the art to give various analogs. Alternatively, compounds of C5 or D5 can be reduced down to the cyclic ether by various methods including catalytic hydrogenation with 10% Pd—C in a suitable solvent such as ethanol to give general structures E5.

Scheme 6: Synthesis of 1-Substituted-2,3,7,8,10,11-hexahydro-1H-4-oxa-9-aza-cyclohepta[a]naphthalene-9-carboxylic acid ethyl ester

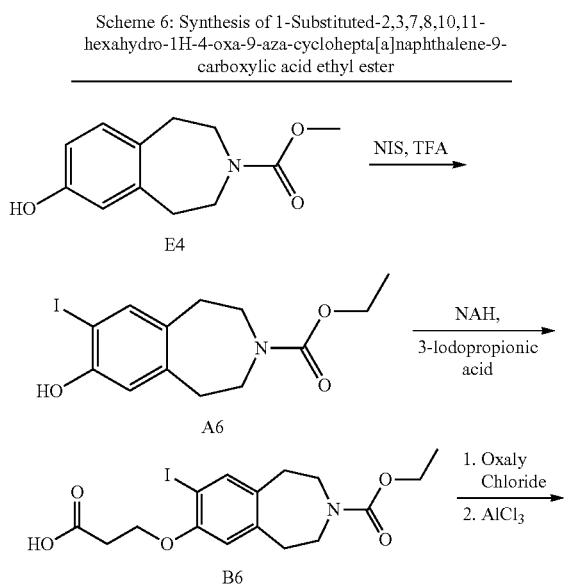

Starting material E4 (described in scheme 4 generically) can be halogenated using N-iodosuccinimide and TFA in a suitable solvent to give the phenol intermediate A6. Iodination was chosen as the preferred halogen because of its high degree of regioselectivity as compared to bromination or chlorination. Alkylation of the phenol analog A6 can be achieved by treatment with 3-iodopropionic acid and a base such as NaH in a suitable solvent such as DMF to give compound B6. Compound B6 can be cyclized by utilizing standard Friedel-Crafts acylation chemistry by first converting the carboxylic acid to the acid chloride with thionyl chloride and then by treatment of the acid chloride with aluminum chloride in a suitable solvent such as DCM to give compound C6. The compound of structure C6 can be treated with nucleophiles such as Grignard reagents or organolithium reagents to give tertiary alcohols of the general structure D6. Alcohols of structure D6 can be reduced directly with triethylsilane and a Lewis acid such as boron trifluoride to give compounds of general structure E6. The aryl iodide E6 can be chemically manipulated further by methods (Suzuki reaction, Buchwald-Hartwig reaction, trans-halogenation, reduction, etc.) know to those skilled in the art to give cyclic ether analogs of the general structure F6.

Scheme 7: Deprotection of various benzazepine analogs

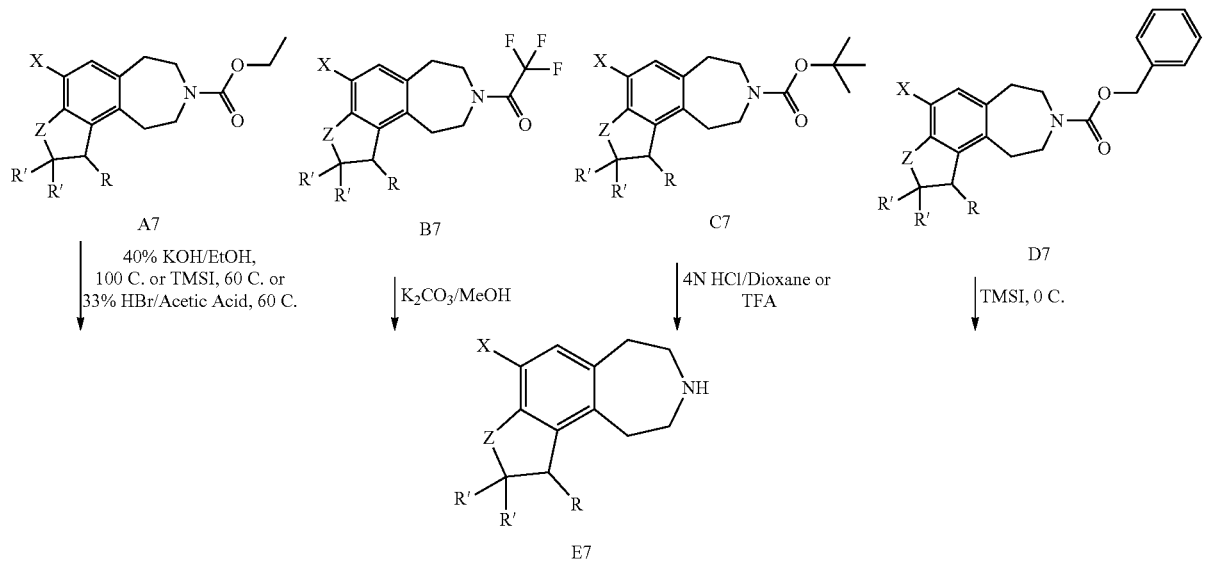

The type of the protecting group and removal thereof is highly dependent upon the nature of the compound. Removal of the protecting group results in a compound of general structure E7. Compound of the general structure A7 which incorporate the ethyl carbamate protecting group can be deprotected in various ways including use of 40% KOH/Ethanol, TMSI, or 33% HBr/acetic acid. Compounds of general structure B7 which incorporate the trifluoroacetimide protecting group can be deprotected in various ways but the use aqueous potassium carbonate in methanol was chosen because of its mild nature. Compounds of general structure C7 which incorporate the tert-butyloxycarbonyl protecting group can be deprotected in various ways including use of 4N HCl/dioxane or TFA. Compounds of general structure D7 which incorporate the benzyloxycarbonyl protecting group can be deprotected in various ways including use of catalytic hydrogenation or TMSI. The latter of which was chosen as preferred for these particular compounds because of its cleaner by-product profile.

The following examples are illustrative of the preparation of representative compounds of the present invention. They are not meant to limit the invention in any way.

Example 1

1,2,3,6,7,8,9,10-Octahydro-8-aza-cyclohepta[e]indene

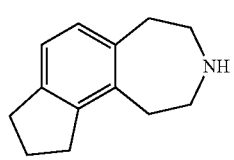 [SMILES: c1cc2c(c3c1CCC3)CCNCC2]

a) 1,3,6,7,9,10-Hexahydro-2H-8-aza-cyclohepta[e]indene-8-carboxylic acid ethyl ester Into a 500 ml Parr hydrogenation bottle, Intermediate 2 (44.5 mg, 0.126 mmol) in EtOH (50 ml) was placed. The bottle was purged with nitrogen, followed by the addition of 10% Pd—C (wet, 40 mg) and 1-drop of sulfuric acid. The reaction mixture was shaken over hydrogen gas (50 psi) for 24 h. The reaction mixture was filtered through celite and solvent evaporated in vacuo. The residue was dissolved in ethyl acetate (50 ml) and washed with aqueous saturated NaHCO$_3$, brine, and dried (Na$_2$SO$_4$). The solvent was evaporated in vacuo to give sub-title product as tan oil that was used directly in the next step. MS: ESI (positive): 260 (M+H).

b) 1,2,3,6,7,8,9,10-Octahydro-8-aza-cyclohepta[e]indene

Into a glass vial, the product from step (a) (0.126 mmol) in CHCl$_3$ (3 ml) was placed. To this stirred solution, TMSI (172 μL, 1.26 mmol) was added. The reaction mixture was heated to 60° C. for 3 h. The reaction mixture was allowed to cool to room temperature and methanol (1 ml) was added to quench. The solvent was evaporated in vacuo to give the crude product as a yellow residue. The crude product was purified by semi-prep RP-HPLC to give the title compound as light yellow oil (15 mg). Recovered as acetate salt: $^1$H NMR (CDCl$_3$) δ 7.18 (bs, 2H), 7.02 (d, J=7.2 Hz, 1H), 6.92 (d, J=7.2 Hz, 1H), 3.15-3.05 (m, 8H), 2.94-2.84 (m, 4H), 2.12-2.02 (m, 2H) 1.98 (s, 3H); MS: ESI (positive): 188 (M+H).

Example 2

1-Methyl-1,2,3,6,7,8,9,10-octahydro-8-aza-cyclohepta[e]indene

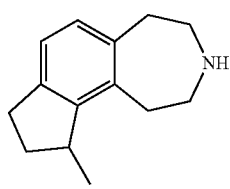

a) 4-Bromo-1-hydroxy-1-methyl-1,3,6,7,9,10-hexahydro-2H-8-aza-cyclohepta[e]indene-8-carboxylic acid ethyl ester Into a glass vial, intermediate 2 (0.16 g, 0.45 mmol) in THF (5 ml) was placed over an Ar atmosphere. The stirred solution was cooled to 0° C., followed by addition of methylmagnesium bromide (3M in diethyl ether, 0.9 ml, 2.7 mmol). The reaction mixture was stirred at 0° C. for 1 h and then quenched by slow addition of aqueous saturated NH$_4$Cl (30 ml). The mixture was extracted with EtOAc (3×). The combined EtOAc extracts were washed with brine, dried (Na$_2$SO$_4$), and solvent evaporated in vacuo to give the sub-titled compound as tan oil that was used without further purification. MS: ESI (positive): 350, 352 (M-OH).

b) 4-Bromo-1-methyl-6,7,9,10-tetrahydro-3H-8-aza-cyclohepta indene-8-carboxylic acid ethyl ester Into a glass vial, the product from step (a) (0.45 mmol) dissolved in 4N HO/dioxane (2 ml) was placed. The reaction mixture was stirred at 60° C. for 1 h. The mixture was cooled to room temperature and the solvent was evaporated in vacuo to give the crude product as a brown solid. The residue was purified by silica-gel chromatography (gradient elution: 0 to 40% EtOAc in hexane) to give the sub-titled compound as a white solid (80 mg). MS: ESI (positive): 350, 352 (M+1).

c) 1-Methyl-1,3,6,7,9,10-hexahydro-2H-8-aza-cyclohepta[e]indene-8-carboxylic acid ethyl ester Into a 500 ml Parr hydrogenation bottle, the product from step (b) (80 mg, 0.23 mmol) dissolved in EtOH (50 ml) was placed. To the argon purged bottle, 10% Pd—C (wet, 100 mg) was added. The bottle was shaken over hydrogen (50 psi) for 3 h. The reaction mixture was filtered through celite and solvent evaporated in vacuo to give the sub-titled compound as colorless oil. MS: ESI (positive): 274 (M+1).

d) 1-Methyl-1,2,3,6,7,8,9,10-octahydro-8-aza-cyclohepta[e]indene

Into a glass vial, the product from step (c) dissolved in CHCl$_3$ (3 ml) was placed. To this solution, TMSI (0.31 ml, 2.3 mmol) was added. The reaction mixture was heated to 60° C. for 4 h and then allowed to cool to room temperature. The reaction mixture was quenched by addition of 2N HCl (5 ml) and further diluted with water (25 ml). The aqueous mixture was washed with diethyl ether (2×). The aqueous layer was basified by addition of 5N KOH to pH 10. The basic solution was extracted with DCM (3×). The combined DCM extracts were washed with brine, dried over Na$_2$SO$_4$, and solvent evaporated in vacuo to give the title product. $^1$H NMR (CDCl$_3$) δ 6.95 (d, J=7.5 Hz, 1H), 6.90 (d, J=7.5 Hz, 1H), 3.36-3.27 (m, 1H), 3.08-2.90 (m, 7H), 2.82-2.74 (m, 1H), 2.27-2.16 (m, 1H), 1.89 (bs, 1H), 1.80-1.73 (m, 1H), 1.33-1.22 (m, 2H), 1.12 (d, J=6.9 Hz, 3H); MS: ESI (positive): 202 (M+H).

Example 3

1-Ethyl-1,2,3,6,7,8,9,10-octahydro-8-aza-cyclohepta[e]indene

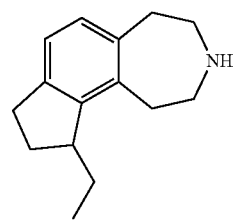 [SMILES: CCC1CCc2ccc3c(c21)CCNCC3]

Example 3 was prepared in a similar fashion to Example 2, except ethylmagnesium bromide (3M in diethyl ether) was used instead of methylmagnesium bromide (Example 2, step (a)). $^1$H NMR (acetone-d6) δ 6.86 (t, J=8.1 Hz, 2H), 3.12-3.05 (m, 1H), 3.00-2.67 (m, 9H), 2.02-1.91 (m, 1H), 1.53-1.41 (m, 1H), 1.39-1.26 (m, 2H), 0.95 (t, J=7.5 Hz, 3H); MS: ESI (positive): 216 (M+H).

Example 4

1-Cyclopropyl-1,2,3,6,7,8,9,10-octahydro-8-aza-cyclohepta[e]indene

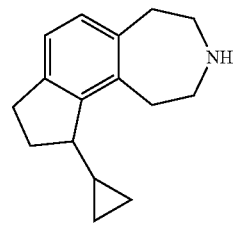 [SMILES: c1cc2c(c3c1CCNCC3)C(C1CC1)CC2]

a) 1-Cyclopropyl-1-hydroxy-1,3,6,7,9,10-hexahydro-2H-8-aza-cyclohepta[e]indene-8-carboxylic acid ethyl ester Into a stirred 100 ml flask containing Intermediate 3 (200 mg, 0.732 mmol) dissolved in diethyl ether (20 ml), cyclopropylmagnesium bromide (0.5M in THF, 7.32 ml, 3.66 mmol) was added at reflux. The reaction mixture was stirred at reflux for 1 hour. The reaction mixture was allowed to cool to room temperature and was quenched by addition of 10% aq. NH$_4$Cl (50 ml). The aqueous mixture was extracted with EtOAc (3×). The combined EtOAc extracts were washed with brine, dried over Na$_2$SO$_4$, and solvent evaporated in vacuo to give the sub-titled compound which was used without further purification. MS: ESI (positive): 298, (M-OH).

b) 1-Cyclopropyl-1,3,6,7,9,10-hexahydro-2H-8-aza-cyclohepta[e]indene-8-carboxylic acid ethyl ester The product from step (a) was dissolved in DCM (20 ml) and cooled to 0° C. To the stirred solution triethylsilane (943 μL, 5.85 mmol) was added, followed by borontrifluoride etherate (456 μL, 3.66 mmol). After 1 hour, additional borontrifluoride etherate (456 µL, 3.66 mmol) was added and the reaction mixture was stirred for an additional hour at 0° C. The reaction was quenched with saturated aqueous NaHCO₃ (50 ml) and the aqueous layer was extracted with DCM (3×). The combined DCM extracts were washed with brine, dried over Na₂SO₄, and solvent evaporated in vacuo. The residue was purified by silica gel chromatography (gradient elution: 0 to 20% EtOAc in hexane) to give the sub-title compound as a colorless oil (103 mg). $^1$H NMR (CDCl₃) δ 7.01-6.93 (m, 2H); 4.16 (q, J=7.2 Hz, 2H); 3.75-3.68 (m, 2H); 3.52-3.43 (m, 2H); 3.11-2.99 (m, 4H); 2.80-2.72 (m, 2H); 2.25-2.14 (m, 1H); 2.06-1.99 (m, 1H); 1.29 (t, J=6.9 Hz, 3H); 0.88-0.77 (m, 1H); 0.55-0.41 (m, 2H); 0.34-0.26 (m, 1H); 0.20-0.13 (m, 1H); MS: ESI (positive): 300, (M+1).

c) 1-Cyclopropyl-1,2,3,6,7,8,9,10-octahydro-8-aza-cyclohepta[e]indene

Into a 20 ml vial, the product from step (b) (103 mg, 0.394 mmol) in CHCl₃ (2 ml) was placed. To this solution, TMSI (468 µL, 3.44 mmol) was added. The reaction mixture was heated at 60° C. for 2 hours and then at room temperature for 16 hours. The volatiles were evaporated in vacuo and 2M HCl (5 ml) and water (25 ml) were added. The aqueous mixture was washed with diethyl ether (2×). The aqueous layer was then basified with 2M NaOH to pH 10 and extracted with DCM (3×). The combined DCM extracts were washed with brine, dried over Na₂SO₄, and solvent evaporated in vacuo to give the title product as a yellow oil (53 mg). 1H NMR (300 MHz, CDCl3) δ 6.99-6.91 (m, 2H); 3.09-2.92 (m, 8H); 2.79-2.71 (m, 2H); 2.24-2.14 (m, 1H); 2.05-1.98 (m, 1H); 1.30-1.21 (m, 2H); 0.88-0.78 (m, 1H); 0.51-0.44 (m, 2H); 0.31-0.026 (m, 1H); 0.23-0.17 (m, 1H); MS: ESI (positive): 228, (M+1).

Example 5

1-Propyl-1,2,3,6,7,8,9,10-octahydro-8-aza-cyclohepta[e]indene

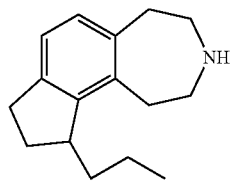 [SMILES: CCCC1CCc2ccc3c(c21)CCNCC3]

Example 5 was prepared in a similar fashion to Example 4, except propylmagnesium chloride (2M in diethyl ether) was used instead of cyclopropylmagnesium bromide (Example 4, step (a)). $^1$H NMR (300 MHz, CDCl3) δ 6.93 (t, J=7.5 Hz, 2H); 3.20-3.13 (m, 1H); 2.96-2.93 (m, 8H); 2.81-2.73 (m, 1H); 2.13-1.90 (m, 2H); 1.47-1.25 (m, 5H); 0.95-0.85 (m, 3H); MS: ESI (positive): 230, (M+1).

Example 6

4-Chloro-1-ethyl-1,2,3,6,7,8,9,10-octahydro-8-aza-cyclohepta[e]indene

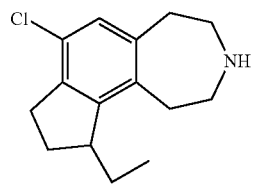 [SMILES: CCC1CCc2c(Cl)cc3c(c21)CCNCC3]

Example 6 was prepared in a similar fashion to Example 4, except Intermediate 4 was used as the starting material and ethylmagnesium bromide (3M in diethyl ether) was used instead of cyclopropylmagnesium bromide (Example 4, step (a)). $^1$H NMR (300 MHz, CDCl3) δ 6.92 (s, 1H); 3.16-3.09 (m, 1H); 2.98-2.84 (m, 10H); 2.37-2.32 (br s, 1H); 2.17-1.94 (m, 2H); 1.47-1.25 (m, 2H); 0.95 (t, J=7.5 Hz, 3H); MS: ESI (positive): 250, (M+1).

Example 7

1-Ethyl-4-iodo-1,2,3,6,7,8,9,10-octahydro-8-aza-cyclohepta[e]indene

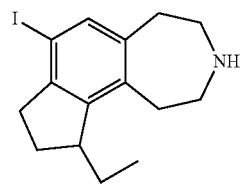 [SMILES: CCC1CCc2c(I)cc3c(c21)CCNCC3]

Example 7 was prepared in a similar fashion to Example 4, except Intermediate 1 was used as the starting material and ethylmagnesium bromide (3M in diethyl ether) was used for instead of cyclopropylmagnesium bromide (Example 4, step (a)). $^1$H NMR (300 MHz, CDCl3) δ 7.32 (s, 1H); 3.28-3.21 (m, 1H); 2.97-2.73 (8H); 2.62-2.60 (br s, 1H); 2.22-1.90 (m, 3H); 1.45-1.30 (m, 2H); 0.95 (t, J=7.2 Hz, 3H); MS: ESI (positive): 342, (M+1).

Example 8

1-Ethyl-4-fluoro-1,2,3,6,7,8,9,10-octahydro-8-aza-cyclohepta[e]indene

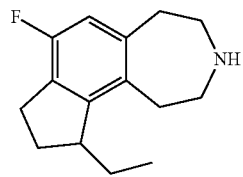 [SMILES: CCC1CCc2c(F)cc3c(c21)CCNCC3]

Example 8 was prepared in a similar fashion to Example 4, except Intermediate 5 was used as the starting material and ethylmagnesium bromide (3M in diethyl ether) was used instead of cyclopropylmagnesium bromide (Example 4, step (a)). $^1$H NMR (300 MHz, CDCl$_3$) δ 6.62 (d, 9.3 Hz, 1H); 3.11-3.06 (m, 1H); 2.96-2.87 (m, 10H); 2.22-1.97 (m, 2H); 1.51-1.31 (m, 2H); 0.95 (t, J=7.2 Hz, 3H); MS: ESI (positive): 234, (M+1).

Example 9

1-Phenyl-1,2,3,6,7,8,9,10-octahydro-8-aza-cyclohepta[e]indene

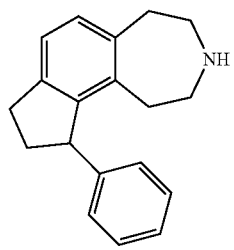 [SMILES: c1ccc(C2CCc3ccc4c(c32)CCNCC4)cc1]

Example 9 was prepared in a similar fashion to Example 4, except phenylmagnesium bromide (3M in diethyl ether) was used instead of cyclopropylmagnesium bromide (Example 4, step (a)). $^1$H NMR (300 MHz, CDCl$_3$) δ 7.23-7.21 (m, 2H); 7.17-7.12 (m, 1H): 7.07-7.05 (m, 1H); 7.01-6.97 (m, 3H); 4.48-4.44 (m, 1H); 3.07-2.81 (m, 6H); 2.73-2.45 (m, 6H); 2.06-2.00 (m, 1H); MS: ESI (positive): 264, (M+1).

Example 10

4-Chloro-1-phenyl-1,2,3,6,7,8,9,10-octahydro-8-aza-cyclohepta[e]indene

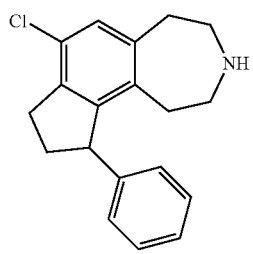 [SMILES: Clc1cc2c(c3c1CCC3c1ccccc1)CCNCC2]

Example 10 was prepared in a similar fashion to Example 4, except Intermediate 4 was used as the starting material and phenylmagnesium bromide (3M in diethyl ether) was used instead of cyclopropylmagnesium bromide (Example 4, step (a)). NMR (300 MHz, CDCl$_3$) δ 7.26-7.21 (m, 2H); 7.19-7.13 (m, 1H); 7.01 (s, 1H); 6.99-6.96 (m, 2H); 4.51-4.47 (m, 1H); 3.07-2.82 (m, 6H); 2.69-2.53 (m, 4H); 2.47-2.42 (m, 1H); 2.24-2.17 (m, 1H); 2.08-2.05 (m, 1H); MS: ESI (positive): 298, (M+1).

Example 11

1-Pyridin-3-yl-1,2,3,6,7,8,9,10-octahydro-8-aza-cyclohepta[e]indene

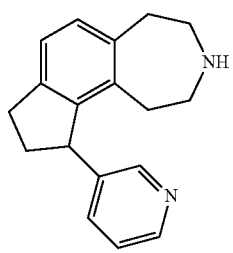 [SMILES: c1cncc(C2CCc3ccc4c(c32)CCNCC4)c1]

a) 1-Hydroxy-4-iodo-1-pyridin-3-yl-1,3,6,7,9,10-hexahydro-2H-8-aza-cyclohepta[e]indene-8-carboxylic acid ethyl ester To a stirred solution of 3-bromopyridine (0.11 ml, 1.13 mmol) in THF (5 ml) under Ar at −78° C., n-BuLi (2.5 M in hexane, 0.45 ml, 1.13 mmol) was added. The mixture was stirred at −78° C. for 20 minutes, followed by dropwise addition of Intermediate 1 (0.15 g, 0.38 mmol) in THF (5 ml). The mixture was stirred for 2 h at −78° C., allowed to warm to room temperature, and quenched by slow addition of aqueous saturated NH$_4$Cl (50 ml). The mixture was extracted with EtOAc (3×). The combined EtOAc extracts were washed with brine, dried (Na$_2$SO$_4$), and solvent evaporated in vacuo to give the sub-title compound as tan oil that was used without further purification. MS: ESI (positive): 479 (M+1).

b) 4-Iodo-1-pyridin-3-yl-6,7,9,10-tetrahydro-3H-8-aza-cyclohepta[e]indene-8-carboxylic acid ethyl ester hydrochloride Into a glass vial, the product from step (a) (0.38 mmol) dissolved in 4N HCl/dioxane (2 ml) was added. The reaction mixture was stirred at 60° C. for 1 h. The mixture was cooled to room temperature and the solvent was evaporated in vacuo to give sub-titled compound as a brown solid that was used without further purification. MS: ESI (positive): 461 (M+1).

c) 1-Pyridin-3-yl-1,3,6,7,9,10-hexahydro-2H-8-aza-cyclohepta[e]indene-8-carboxylic acid ethyl ester Into a 500 ml Parr hydrogenation bottle, the product from step (b) (0.38 mmol) dissolved in EtOH (50 ml) was added. To the argon purged bottle, 100 mg of 20% Pd(OH)$_2$ was placed. The bottle was shaken over hydrogen (50 psi) for 6 h. The reaction mixture was filtered through celite and solvent evaporated in vacuo. The residue was dissolved in DCM and washed with saturated aqueous Na$_2$CO$_3$. The DCM layer was dried over Na$_2$SO$_4$ and solvent was evaporated in vacuo to give the crude product that was purified by silica-gel chromatography (gradient elution: 0 to 80% EtOAc in hexane) to give the sub-title compound as a yellow oil (70 mg). MS: ESI (positive): 337 (M+1).

d) 1-Pyridin-3-yl-1,2,3,6,7,8,9,10-octahydro-8-aza-cyclohepta[e]indene

Into a glass vial, the product from step (c) in 2.5 ml acetic acid and 2.5 ml HBr (33% in acetic acid) was added. The stirred reaction mixture was heated at 60° C. for 6 hours. The reaction mixture was cooled and the volatiles were evaporated in vacuo. The residue was dissolved in water (25 ml) and washed with diethyl ether (3×). The aqueous layer was basified with 2M NaOH to pH 10 and extracted with DCM (3×). The combined DCM extracts were washed with brine, dried over $Na_2SO_4$, and solvent evaporated in vacuo to give the title compound as a colorless oil (35 mg). $^1$H NMR (300 MHz, $CDCl_3$) δ 8.43-8.38 (m, 2H); 7.22-7.12 (m, 2H); 7.08-7.00 (m, 2H); 4.49 (dd, J=8.7 Hz, 2.7 Hz, 1H); 3.10-2.82 (m, 6H); 2.73-2.45 (m, 5H); 2.04-1.93 (m, 2H); MS: ESI (positive): 265 (M+1).

Example 12

4-Fluoro-1-pyridin-3-yl-1,2,3,6,7,8,9,10-octahydro-8-aza-cyclohepta[e]indene

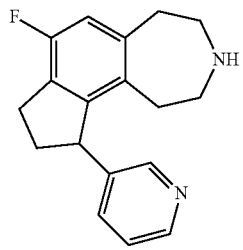 [SMILES: Fc1cc2c(c3c1CCC3c1cccnc1)CCNCC2]

Example 12 was prepared in a similar fashion to Example 11, except Intermediate 5 was used as the starting material and the hydrogenation (step c) was conducted at atmospheric pressure. $^1$H NMR (300 MHz, $CDCl_3$) δ 8.44-8.42 (m, 1H); 8.37 (s, 1H); 7.22-7.14 (m, 2H); 6.74 (d, J=9.3 Hz, 1H); 4.49 (d, J=9 Hz, 1H); 3.02-2.77 (m, 6H); 2.71-2.42 (m, 5H); 2.08-2.02 (m, 1H); 1.98 (br s, 1H); MS: ESI (positive): 283 (M+1).

Example 13

1,1-Dimethyl-1,2,3,6,7,8,9,10-octahydro-8-aza-cyclohepta[e]indene

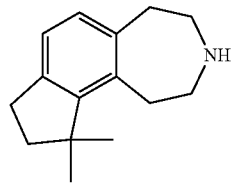 [SMILES: CC1(C)CCc2ccc3c(c21)CCNCC3]

a) 1,1-Dimethyl-1,3,6,7,9,10-hexahydro-2H-8-aza-cyclohepta[e]indene-8-carboxylic acid ethyl ester Into a 100 ml flask, $TiCl_4$ (480 μL, 4.35 mmol) in DCE (10 ml) was placed. The solution was cooled to −78° C., followed by addition of dimethylzinc (1M heptanes, 3.7 ml, 4.35 mmol). The mixture was stirred for 15 minutes, followed by dropwise addition of Intermediate 3 (200 mg, 0.732 mmol) in DCE (5 ml). The reaction mixture was allowed to warm to room temperature and then refluxed for 5 hours. The reaction mixture was cooled to room temperature and quenched with ice water. The aqueous/organic mixture was filtered through celite. The aqueous layer was extracted with DCM (3×). The combined DCM extracts were washed with brine, dried over $Na_2SO_4$, and solvent evaporated in vacuo to give the crude product. Purification by silica-gel chromatography (gradient elution: 0 to 20% EtOAc in hexanes) gave the sub-title compound as a colorless oil (102 mg). $^1$H NMR (300 MHz, $CDCl_3$) δ 6.97-6.95 (m, 2H); 4.16 (q, J=7.2 Hz, 2H); 3.70-3.59 (m, 4H); 3.03-3.02 (m, 2H); 2.92-2.91 (m, 2H); 2.80 (t, J=7.2 Hz, 2H); 1.91 (t, J=7.2 Hz, 2H); 1.35 (s, 6H); 1.27 (t, J=7.2 Hz, 3H); MS: ESI (positive): 288 (M+1).

b) 1,1-Dimethyl-1,2,3,6,7,8,9,10-octahydro-8-aza-cyclohepta[e]indene

Into a glass vial containing the product from step (a) (102 mg, 0.355 mmol) in $CHCl_3$ (2 ml), TMSI (483 μL, 3.55 mmol) was added. The reaction mixture was heated to 60° C. for 2 hours. The volatiles were evaporated in vacuo and 2M HCl (5 ml) and water (25 ml) were added. The aqueous mixture was washed with diethyl ether (2×). The aqueous layer was then basified with 2M NaOH to pH 10 and extracted with DCM (3×). The combined DCM extracts were washed with brine, dried over $Na_2SO_4$, and solvent evaporated in vacuo to give the title product as a white semi-solid (38 mg). $^1$H NMR (300 MHz, $CDCl_3$) δ 6.93-6.91 (m, 2H); 3.05-2.89 (m, 8H); 2.80 (t, J=7.5 Hz, 2H); 1.98 (br s, 1H); 1.90 (t, J=7.5 Hz, 2H); 1.35 (s, 6H); MS: ESI (positive): 216 (M+1).

Example 14

2,2-Difluoro-1-phenyl-1,2,3,6,7,8,9,10-octahydro-8-aza-cyclohepta[e]indene

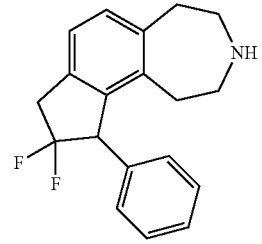 [SMILES: FC1(F)Cc2ccc3c(c2C1c1ccccc1)CCNCC3]

a) 2-Fluoro-1-oxo-1,3,6,7,9,10-hexahydro-2H-8-aza-cyclohepta[e]indene-8-carboxylic acid ethyl ester Into a 500 ml flask, intermediate 3 (6.1 g, 22.34 mmol) dissolved in MeOH (100 ml) was added. To this solution, Selectfluor (15.8 g, 44.68 mmol) was added. The reaction mixture was heated to reflux for 2 hours and then allowed to cool to room temperature. The solvent was evaporated in vacuo and the residue dissolved in DCM and filtered through celite. The filtrate was partitioned with water and the aqueous layer was extracted with DCM (3×). The combined DCM extracts were washed with brine, dried over $Na_2SO_4$, and solvent evaporated in vacuo to give the sub-title product as light yellow solid (6.0 g) that was used without further purification. MS: ESI (positive): 292 (M+1).

b) 2,2-Difluoro-1-oxo-1,3,6,7,9,10-hexahydro-2H-8-aza-cyclohepta[e]indene-8-carboxylic acid ethyl ester Into a 500 ml flask, the product from step (a) (6.01 g, 20.65 mmol) dissolved in DCM (100 ml) was added. The solution was cooled to 0° C. and TEA (17.27 ml, 123.91 mmol) was added, followed by TBDMS-triflate (14.222 ml, 61.95 mmol). After 10 minutes, the ice bath was removed and the mixture was stirred at room temperature for 16 hours. The contents were washed with saturated aqueous $NaHCO_3$, 1M citric acid, saturated aqueous $NaHCO_3$, brine, and dried over $Na_2SO_4$. Evaporation of solvent yielded a brown liquid which was immediately dissolved in acetonitrile (100 ml). The solution was cooled to 0° C. and Selectfluor (14.6 g, 41.3 mmol) was added portion-wise at 0° C. over 30 minutes. The flask was then warmed to room temperature and stirred for 1 hour. The contents were partitioned between DCM and water and the aqueous layer was extracted with DCM (3×). The combined DCM extracts were washed with brine, dried over $Na_2SO_4$, and solvent evaporated in vacuo to give the crude product. Purification by silica-gel chromatography (gradient elution: 0 to 40% EtOAc) gave the sub-title product an off-white solid (5.1 g). $^1$H NMR (300 MHz, $CDCl_3$) δ 7.45 (d, J=7.8 Hz, 1H); 7.23 (d, J=7.5 Hz, 1H); 4.16 (t, J=6.9 Hz, 2H); 3.63-3.57 (m, 6H); 3.46 (t, J=12.9 Hz, 2H); 3.01-2.98 (m, 2H); 1.27 (t, J=7.2 Hz, 3H); MS: ESI (positive): 310 (M+1).

c) 2,2-Difluoro-1-hydroxy-1-phenyl-1,3,6,7,9,10-hexahydro-2H-8-aza-cyclohepta[e]indene-8-carboxylic acid ethyl ester Into a 250 ml flask, the product from step (b) (5.1 g, 16.5 mmol) dissolved in diethyl ether (100 ml) was added. The stirred solution was heated to reflux and phenylmagnesium bromide (3M in ether, 27.5 ml, 82.5 mmol) was added. The reaction mixture was stirred at reflux for 1 hour and then allowed to cool to room temperature. The reaction mixture was quenched with 10% aqueous $NH_4Cl$ (100 ml) and extracted with EtOAc (3×). The combined EtOAc extracts were washed with brine, dried over $Na_2SO_4$, and solvent evaporated in vacuo to give the crude product. Purification by silica-gel chromatography (gradient elution: 0 to 50% EtOAc in hexanes) gave the sub-title compound as a white semi-solid (5.78 g). $^1$H NMR (300 MHz, $CDCl_3$) δ 7.39-7.30 (m, 3H); 7.26-7.17 (m, 3H); 7.10-7.07 (m, 1H); 4.13-3.85 (m, 2H); 3.62-3.50 (m, 2H); 3.43-3.34 (m, 2H); 3.28-3.18 (m, 2H); 2.98-2.86 (m, 3H); 2.77-2.69 (m, 1H); 1.26-1.09 (m, 3H); MS: ESI (positive): 388 (M+1).

d) 1-Chloro-2,2-difluoro-1-phenyl-1,3,6,7,9,10-hexahydro-2H-8-aza-cyclohepta[e]indene-8-carboxylic acid ethyl ester Into a 100 ml flask, the product from step (c) (5.78 g, 14.93 mmol) dissolved in thionyl chloride (50 ml) was added. Pyridine (120 µL, 1.49 mmol) was added and the reaction mixture heated to 70° C. for 1 hour. The reaction mixture was allowed to cool to room temperature and the volatiles were evaporated in vacuo. The residue was partitioned between saturated aqueous $Na_2CO_3$ and EtOAc. The aqueous layer was extracted with EtOAc (3×). The combined EtOAc extracts were washed with brine, dried over $Na_2SO_4$, and solvent evaporated in vacuo to give the sub-title compound as an orange semi-solid (5.9 g) that was used directly in the next step. MS: ESI (positive): 405 (M+1).

e) 2,2-Difluoro-1-phenyl-1,3,6,7,9,10-hexahydro-2H-8-aza-cyclohepta[e]indene-8-carboxylic acid ethyl ester Into a 500 ml Parr bottle, the product from step (d) (5.9 g, 14.56 mmol) dissolved in EtOH (150 ml) was added. To the solution, 5% Pd—C (3 g) was added. The reaction mixture was shaken over hydrogen (50 psi) for 16 hours. The reaction mixture was filtered through celite and the volatiles were evaporated in vacuo to give the crude product. Purification by silica-gel chromatography (gradient elution: 0 to 20% EtOAc in hexanes) gave the sub-title compound as a colorless oil (4.25 g). $^1$H NMR (300 MHz, $CHCl_3$) δ 7.28-7.26 (m, 3H); 7.10 (s, 2H); 7.01-6.98 (m, 2H); 4.64 (d, J=20.1 Hz, 1H); 4.11-4.01 (m, 2H); 3.66-3.60 (m, 1H); 3.54-3.31 (m, 4H); 3.13-3.06 (m, 1H); 2.89-2.85 (m, 2H); 2.67-2.47 (m, 2H); 1.26-1.22 (m, 3H); MS: ESI (positive): 372 (M+1).

f) 2,2-Difluoro-1-phenyl-1,2,3,6,7,8,9,10-octahydro-8-aza-cyclohepta[e]indene Into a 250 ml flask, the product from step (e) (3.75 g, 10.10 mmol) dissolved in acetic acid (50 ml) and HBr (33% in acetic acid, 50 ml) was added. The reaction mixture was heated to 60° C. for 6 hours. The reaction mixture was cooled and the volatiles were evaporated in vacuo. The crude product was dissolved in water (100 ml) and washed with diethyl ether (3×). The aqueous layer was basified with 2M NaOH to pH 10 and then extracted with DCM (3×). The combined DCM extracts were washed with brine, dried over $Na_2SO_4$, and solvent evaporated in vacuo to give the title compound as tan oil (2.8 g) which solidified over time. $^1$H NMR (300 MHz, $CDCl_3$) δ 7.32-7.26 (m, 3H); 7.10-7.07 (m, 2H); 7.02-6.99 (m, 2H); 4.62 (d, J=19.8 Hz, 1H); 3.44-3.35 (m, 2H); 2.99-2.83 (m, 4H); 2.73-2.64 (m, 2H); 2.58-2.45 (m, 2H); 2.33 (bs, 1H); MS: ESI (positive): 300 (M+1).

Example 15

2,2-Difluoro-1-o-tolyl-1,2,3,6,7,8,9,10-octahydro-8-aza-cyclohepta[e]indene

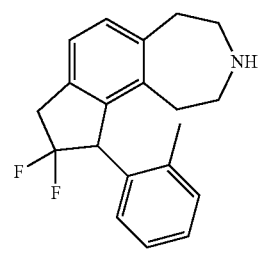 [SMILES: Cc1ccccc1C1c2c(ccc3c2CCNCC3)CC1(F)F]

Example 15 was prepared in a similar fashion to Example 14, except o-tolylmagnesium bromide was used instead of phenylmagnesium bromide (example 14, step (c)). $^1$H NMR (300 MHz, $CDCl_3$) δ 7.25-7.22 (m, 1H); 7.17-7.12 (m, 1H); 7.07-6.98 (m, 3H); 6.47 (d, J=7.5 Hz, 1H); 4.87 (d, J=20.4 Hz, 1H); 3.53-3.29 (m, 2H); 3.00-2.82 (m, 4H); 2.70-2.39 (m, 7H); 1.77 (bs, 1H); MS: ESI (positive): 314 (M+1).

Example 16

2,2-Difluoro-1-m-tolyl-1,2,3,6,7,8,9,10-octahydro-8-aza-cyclohepta[e]indene

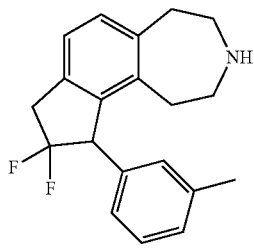 [SMILES: Cc1cccc(C2c3c(ccc4c3CCNCC4)CC2(F)F)c1]

Example 16 was prepared in a similar fashion to Example 14, except m-tolylmagnesium chloride was used instead of phenylmagnesium bromide (example 14, step (c)). $^1$H NMR (300 MHz, CDCl$_3$) δ 7.16 (t, J=7.5 Hz, 1H); 7.10-7.04 (m, 3H); 6.85 (bs, 1H); 6.77-6.74 (m, 1H); 4.59 (d, J=20.4 Hz, 1H); 3.53-3.35 (m, 2H); 2.98-2.83 (m, 4H); 2.73-2.65 (m, 2H); 2.62-2.52 (m, 2H); 2.48 (s, 3H); 1.98 (bs, 1H); MS: ESI (positive): 314 (M+1).

Example 17

2,2-Difluoro-1-p-tolyl-1,2,3,6,7,8,9,10-octahydro-8-aza-cyclohepta[e]indene

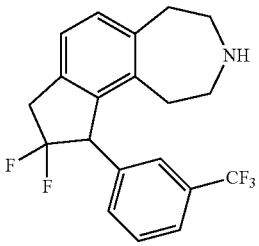 [SMILES: FC(F)(F)c1cccc(C2c3c(ccc4c3CCNCC4)CC2(F)F)c1]

Example 17 was prepared in a similar fashion to Example 14, except p-tolylmagnesium bromide was used instead of phenylmagnesium bromide (example 14, step (c)). $^1$H NMR (300 MHz, CDCl$_3$) δ 7.01-7.04 (m, 4H); 6.89-6.87 (m, 2H); 4.59 (d, J=20.1 Hz, 1H); 3.45-3.33 (m, 2H); 2.94-2.87 (m, 4H); 2.71-2.66 (m, 2H); 2.56-2.51 (m, 2H); 2.31 (s, 3H); 2.22 (bs, 1H); MS: ESI (positive): 314 (M+1).

Example 18

2,2-Difluoro-1-(3-trifluoromethyl-phenyl)-1,2,3,6,7,8,9,10-octahydro-8-aza-cyclohepta[e]indene Example 18 was prepared in a similar fashion to Example 14, except (3-(trifluoromethyl)phenyl)magnesium chloride (prepared from 3-bromobenzotrifluoride (1 eq) in THF, followed by addition of isopropyl magnesium chloride (2M in THF, 1 eq) at room temperature and stirring for 16 hours was used instead of phenylmagnesium bromide (example 14, step (c)) $^1$H NMR (300 MHz, CDCl$_3$) δ 7.55-7.53 (m, 1H); 7.42 (t, J=7.8 Hz, 1H); 7.29 (bs, 1H); 7.20-7.17 (m, 1H); 7.13-7.07 (m, 2H); 4.70 (d, J=19.2, 1H); 3.51-3.36 (m, 2H); 3.01-2.84 (m, 4H); 2.74-2.61 (m, 2H); 2.54-2.49 (m, 2H); 2.01 (bs, 1H); MS: ESI (positive): 368 (M+1).

Example 19

2,2-Difluoro-1-(3-trifluoromethoxy-phenyl)-1,2,3,6,7,8,9,10-octahydro-8-aza-cyclohepta[e]indene

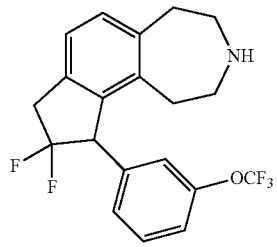 [SMILES: FC(F)(F)Oc1cccc(C2c3c(ccc4c3CCNCC4)CC2(F)F)c1]

Example 19 was prepared in a similar fashion to Example 14, except 3-(trifluoromethoxy)phenylmagnesium bromide was used instead of phenylmagnesium bromide (example 14, step (c)). $^1$H NMR (300 MHz, CDCl$_3$) δ 7.33 (t, J=8.1 Hz, 1H); 7.18-7.14 (m, 3H); 6.88-6.85 (m, 2H); 4.62 (d, J=18.9 Hz, 1H); 3.47-3.37 (m, 2H); 3.26-3.16 (m, 4 µl); 3.01-2.96 (m, 2H); 2.85-2.77 (m, 2H); MS: ESI (positive): 384 (M+1).

Example 20

2,2-Difluoro-1-(4-fluoro-phenyl)-1,2,3,6,7,8,9,10-octahydro-8-aza-cyclohepta[e]indene

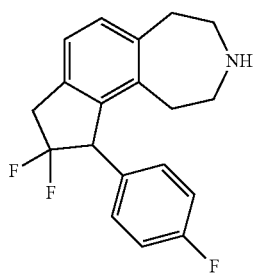 [SMILES: Fc1ccc(C2c3c(ccc4c3CCNCC4)CC2(F)F)cc1]

Example 20 was prepared in a similar fashion to Example 14, except 4-fluorophenylphenylmagnesium bromide was used instead of phenylmagnesium bromide (example 14, step (c)). $^1$H NMR (CDCl$_3$) δ 7.1 (d, J=7.8 Hz, 2H), 6.98 (d, J=7.2 Hz, 4H), 4.62 (d, J=19.2 Hz, 1H), 3.4-3.5 (m, 2H), 2.85-3.05 (m, 4H) 2.4-2.8 (m, 4H); MS: ESI (positive): 318 (M+H).

Example 21

2,2-Difluoro-1-(3-fluoro-phenyl)-1,2,3,6,7,8,9,10-octahydro-8-aza-cyclohepta[e]indene

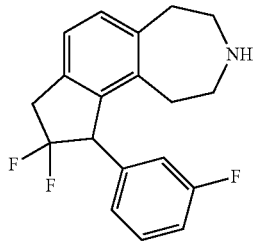 [SMILES: Fc1cccc(C2c3c(ccc4c3CCNCC4)CC2(F)F)c1]

Example 21 was prepared in a similar fashion to Example 14, except 3-fluorophenylphenylmagnesium bromide was used instead of phenylmagnesium bromide (example 14, step (c)). $^1$H NMR (CDCl$_3$) δ 7.23-7.30 (m, 1H), 7.09 (d, J=7.8 Hz, 1H), 7.06 (d, J=7.5 Hz, 1H), 6.96 (m, 1H), 6.84 (d, J=7.8 Hz, 1H), 6.68 (d, J=9.6 Hz, 1H), 4.63 (d, J=19.8 Hz, 1H), 3.35-3.46 (m, 2H), 2.83-2.97 (m, 4H), 2.47-2.74 (m, 4H); MS: ESI (positive): 318 (M+H).

Example 22

1-Cyclopropyl-2,2-difluoro-1,2,3,6,7,8,9,10-octahydro-8-aza-cyclohepta[e]indene

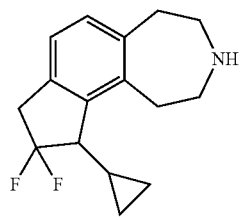 [SMILES: FC1(F)Cc2ccc3c(c2C1C1CC1)CCNCC3]

Example 22 was prepared in a similar fashion to Example 14, except cyclopropylmagnesium bromide (0.5 M in THF) was used instead of phenylmagnesium bromide (example 14, step (c)). $^1$H NMR (300 MHz, CDCl$_3$) δ 7.00-6.91 (m, 2H); 3.52-3.10 (m, 3H); 3.00-2.89 (m, 8H); 0.94-0.82 (m, 1H); 0.65-0.56 (m, 1H); 0.52-0.43 (m, 1H); 0.37-0.29 (m, 1H); 0.08-0.02 (m, 1H); MS: ESI (positive): 264 (M+H).

Example 23

1-(3-Chloro-phenyl)-2,2-difluoro-1,2,3,6,7,8,9,10-octahydro-8-aza-cyclohepta[e]indene

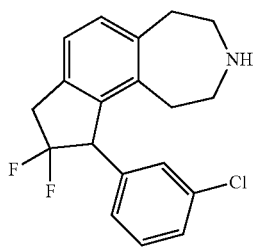

a) 1-(3-Chloro-phenyl)-2,2-difluoro-1-hydroxy-1,3,6,7,9,10-hexahydro-2H-8-aza-cyclohepta[e]indene-8-carboxylic acid ethyl ester Step (a) was conducted in a similar fashion to example 14, step (c), except 3-chlorophenylmagnesium bromide was used instead of phenylmagnesium bromide to give the sub-title compound. MS: ESI (positive): 422 (M+1).

b) 1-Chloro-1-(3-chloro-phenyl)-2,2-difluoro-1,3,6,7,9,10-hexahydro-2H-8-aza-cyclohepta[e]indene-8-carboxylic acid ethyl ester Step (b) was conducted in a similar fashion to example 14, step (d), except the product of step (a) was used to give the sub-title compound. MS: ESI (positive): 440 (M+1).

c) 1-(3-Chloro-phenyl)-2,2-difluoro-1,3,6,7,9,10-hexahydro-2H-8-aza-cyclohepta[e]indene-8-carboxylic acid ethyl ester Into an appropriately sized flask, the product from step (b) (110 mg, 0.25 mmol) in toluene (3 ml) was added. The flask was purged with nitrogen and tributyltin hydride (134 μL, 0.5 mmol) was added. The reaction mixture was placed in a pre-heated (110° C.) oil bath and stirred for 20 minutes. The reaction was cooled and quenched with saturated aqueous NaHCO$_3$ and extracted with EtOAc (3×). The combined EtOAc extracts were washed with brine, dried over Na$_2$SO$_4$, and solvent evaporated in vacuo to give the crude product which was purified by silica-gel chromatography (gradient elution: 0 to 20% EtOAc in hexanes) to give the sub-title compound as a white semi-solid (52 mg). MS: ESI (positive): 406 (M+1).

d) 1-(3-Chloro-phenyl)-2,2-difluoro-1,2,3,6,7,8,9,10-octahydro-8-aza-cyclohepta[e]indene Step (d) was conducted in a similar fashion to example 14, step (0, except the product of step (c) was used to give the title compound. $^1$H NMR (300 MHz, CDCl$_3$) δ 7.25-7.22 (m, 2H); 7.12-7.05 (m, 2H); 6.99 (bs, 1H); 6.92-6.89 (m, 1H); 4.60 (d, J=18.9 Hz, 1H); 3.46-3.35 (m, 2H); 2.99-2.89 (m, 3H); 2.74-2.62 (m, 2H); 2.57-2.49 (m, 2H); 2.24-2.19 (m, 1H); 2.01 (bs, 1H); MS: ESI (positive): 334 (M+1).

Example 24

1-(4-Chloro-phenyl)-2,2-difluoro-1,2,3,6,7,8,9,10-octahydro-8-aza-cyclohepta[e]indene

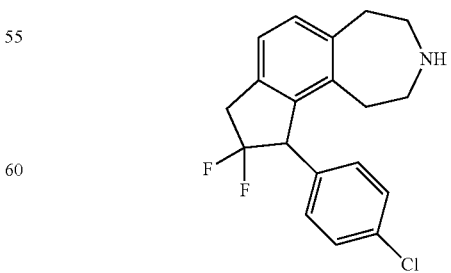

Example 24 was prepared in a similar fashion to Example 23, except 4-chlorophenylmagnesium bromide was used instead of 3-chlorophenylmagnesium bromide (example 23, step (a)). ¹H NMR (300 MHz, CDCl₃) δ 7.29-7.24 (m, 2H); 7.10-7.04 (m, 2H); 6.95-6.90 (m, 2H); 4.60 (d, J=19.8 Hz, 1H); 3.44-3.40 (m, 1H); 3.36-3.33 (m, 1H); 2.96-2.84 (m, 4H); 2.74-2.61 (m, 2H); 2.55-2.48 (m, 2H); 1.66 (bs, 1H); MS: ESI (positive): 334 (M+1).

Example 25

2,2-Difluoro-1-(2-methoxy-phenyl)-1,2,3,6,7,8,9,10-octahydro-8-aza-cyclohepta[e]indene

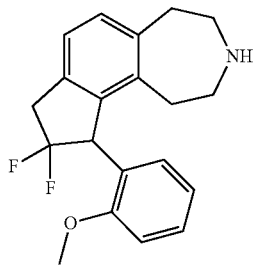 [SMILES: COc1ccccc1C1c2c(ccc3c2CCNCC3)CC1(F)F]

a) 2,2-Difluoro-3,6,7,8,9,10-hexahydro-2H-8-aza-cyclohepta[e]inden-1-one

Into a 100 ml flask, Intermediate 3 (1 g, 3.2 mmol) dissolved in CHCl₃ (20 ml) was added. To this solution, iodotrimethylsilane (4.4 ml, 32.3 mmol) was added. The reaction mixture was heated to 70° C. for 4 hours, and then volatiles were evaporated in vacuo. The residue was dissolved in 2M HCl (30 ml) and washed with diethyl ether (2×). The aqueous layer was basified with 2M NaOH to pH 10 and extracted with DCM (3×). The combined DCM extracts were washed with brine, dried over Na₂SO₄, and solvent evaporated in vacuo to give the sub-title compound as a light yellow solid (607 mg) that was used without purification. MS: ESI (positive): 238 (M+1).

b) 2,2-Difluoro-1-oxo-1,3,6,7,9,10-hexahydro-2H-8-aza-cyclohepta[e]indene-8-carboxylic acid tert-butyl ester Into a 100 ml flask, the product from step (a) (300 mg, 1.26 mmol) dissolved in DCM (10 ml) was added. To this stirred solution, DIEA (268 µL, 1.51 mmol) was added, followed by di-t-butyl dicarbonate (331 mg, 1.51 mmol). The reaction mixture was stirred at room temperature for 16 hours, and then diluted with 2N citric acid (50 ml). The aqueous mixture was extracted with DCM (3×). The combined DCM extracts were washed with brine, dried over Na₂SO₄, and solvent evaporated in vacuo to give the crude product. Purification by silica-gel chromatography (gradient elution: 0 to 20% EtOAc in hexanes) gave the sub-title compound as a white solid (391 mg). ¹H NMR (300 MHz, CDCl₃) δ 7.46-7.43 (m, 1H); 7.23-7.21 (m, 1H); 3.62-3.57 (m, 6H); 3.46 (t, J=12.9 Hz, 2H); 3.00-2.97 (m, 2H); 1.45 (s, 9H); MS: ESI (positive): 338 (M+1).

c) 2,2-Difluoro-1-hydroxy-1-(2-methoxy-phenyl)-1,3,6,7,9,10-hexahydro-2H-8-aza-cyclohepta[e]indene-8-carboxylic acid tert-butyl ester Into a glass vial containing the product from step (b) (130 mg, 0.385 mmol) in diethyl ether (5 ml), 2-methoxyphenyl magnesium bromide (3.85 ml, 1.92 mmol) was added. The reaction mixture was stirred at reflux for 30 minutes. The reaction was cooled to room temperature, quenched with of 10% aqueous NH₄Cl (50 ml), and extracted with EtOAc (3×). The combined EtOAc extracts were washed with brine, dried over Na₂SO₄, and the solvent evaporated in vacuo to give the crude product. Purification by silica-gel chromatography (gradient elution: 0 to 40% EtOAc in hexanes) gave the sub-title compound as a yellow oil (145 mg). MS: ESI (positive): 446 (M+1).

d) 2,2-Difluoro-1-(2-methoxy-phenyl)-1,2,3,6,7,8,9,10-octahydro-8-aza-cyclohepta[e]indene Into a glass vial, the product from step (c) (112 mg, 0.251 mmol) dissolved in 2 ml DCM was added. To this stirred solution, triethylsilane (603 µL, 3.77 mmol) was added, followed by TFA (290 µL, 3.77 mmol). After stirring at room temperature for 16 hours, additional triethylsilane (603 µL, 3.77 mmol) and TFA (290 µL, 3.77 mmol) were added. The reaction mixture was stirred for an additional 16 hours. The volatiles were then evaporated in vacuo and the residue diluted with 2M HCl (20 ml). The aqueous mixture was washed with diethyl ether (2×), basified with 2M NaOH to pH 10, and extracted with DCM (3×). The combined DCM extracts were washed with brine, dried over Na₂SO₄, and solvent evaporated in vacuo to give the title compound as a white semi-solid (52 mg). ¹H NMR (300 MHz, CDCl₃) δ 7.23-7.20 (m, 1H); 7.08-7.02 (m, 2H); 6.95-6.91 (m, 1H); 6.78 (t, J=7.5 Hz, 1H); 6.51 (bs, 1H); 5.15 (d, J=21.0 Hz, 1H); 3.91 (s, 3H); 3.47-3.28 (m, 2H); 2.97-2.81 (m, 4H); 2.72-2.62 (m, 2H); 2.51-2.46 (2H); 1.68 (bs, 1H); MS: ESI (positive): 330 (M+1).

Example 26

2,2-Difluoro-1-(3-methoxy-phenyl)-1,2,3,6,7,8,9,10-octahydro-8-aza-cyclohepta[e]indene

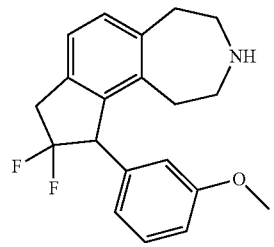 [SMILES: COc1cccc(C2c3c(ccc4c3CCNCC4)CC2(F)F)c1]

Example 26 was prepared in a similar fashion to Example 25, except 3-methoxyphenylmagnesium bromide was used instead of 2-methoxyphenyl magnesium bromide (Example 25, step (c)). ¹H NMR (300 MHz, CDCl₃) δ 7.20 (t, 8.1 Hz, 1H); 7.09-7.03 (m, 2H); 6.82-6.78 (m, 1H); 6.60-6.56 (m, 2H); 4.59 (d, J=20.1 Hz, 1H); 3.76 (s, 3H); 3.47-3.34 (m, 2H); 2.98-2.82 (m, 4H); 2.74-2.62 (m, 2H); 2.59-2.51 (m, 2H); 1.81 (bs, 1H); MS: ESI (positive): 330 (M+1).

Example 27

2,2-Difluoro-1-(4-methoxy-phenyl)-1,2,3,6,7,8,9,10-octahydro-8-aza-cyclohepta[e]indene

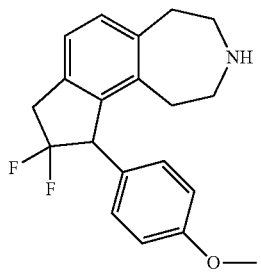 [SMILES: COc1ccc(C2c3c(ccc4c3CCNCC4)CC2(F)F)cc1]

Example 27 was prepared in a similar fashion to Example 25, except 4-methoxyphenylmagnesium bromide was used instead of 2-methoxyphenyl magnesium bromide (Example 25, step (c)). $^1$H NMR (300 MHz, CDCl$_3$) δ 7.09-7.03 (m, 2H); 6.93-6.90 (m, 2H); 6.84-6.79 (m, 2H); 4.57 (d, J=20.1 Hz, 1H); 3.78 (s, 3H); 3.44-3.32 (m, 2H); 2.96-2.82 (m, 4H); 2.73-2.63 (m, 2H); 2.58-2.51 (m, 2H); 1.83 (bs, 1H); MS: ESI (positive): 330 (M+1).

Example 28

2,2-Difluoro-1-pyridin-3-yl-1,2,3,6,7,8,9,10-octahydro-8-aza-cyclohepta[e]indene

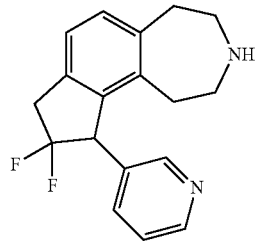 [SMILES: FC1(F)Cc2ccc3c(c2C1c1cccnc1)CCNCC3]

a) 2,2-Difluoro-1-hydroxy-1-pyridin-3-yl-1,3,6,7,9,10-hexahydro-2H-8-aza-cyclohepta[e]indene-8-carboxylic acid ethyl ester Into a 1 L flask containing 3-bromopyridine (9.46 ml, 97.1 mmol) in THF (200 ml), isopropylmagnesium chloride (2M in THF, 48.5 ml, 97.1 mmol) was added. The reaction mixture was heated to 50° C. and stirred for 5 hours. Next, a solution of Intermediate 3 (6.0 g, 19.41 mmol) in THF (50 ml) was added drop-wise. The reaction mixture was stirred at 50° C. for 1 hour. The reaction mixture was then cooled to 0° C., quenched with saturated aqueous Na$_2$CO$_3$ (200 ml), and extracted with DCM (3×). The combined DCM extracts were washed with brine, dried over Na$_2$SO$_4$, and solvent evaporated in vacuo to give the crude product. Purification by silica-gel chromatography (gradient elution: 0 to 70% EtOAc in hexanes) gave the sub-title compound as a white semi-solid (5.9 g). MS: ESI (positive): 389 (M+1).

b) 1-Bromo-2,2-difluoro-1-pyridin-3-yl-1,3,6,7,9,10-hexahydro-2H-8-aza-cyclohepta[e]indene-8-carboxylic acid ethyl ester Into a 500 ml flask containing the product from step (a) (5.9 g, 15.20 mmol) in DCE (50 ml), thionyl bromide (5.89 ml, 76.03 mmol) was added, followed by pyridine (123 μL, 1.52 mmol). The stirred reaction mixture was heated to 70° C. for 30 minutes. The reaction mixture was then allowed to cool to room temperature and was carefully poured over ice-cold saturated aqueous Na$_2$CO$_3$ and extracted with DCM (3×). The combined DCM extracts were washed with brine, dried over Na$_2$SO$_4$, and solvent evaporated in vacuo to give the sub-title compound as a pale red semi-solid that was used without further purification. MS: ESI (positive): 451, 453 (M+1).

c) 2,2-Difluoro-1-pyridin-3-yl-1,3,6,7,9,10-hexahydro-2H-8-aza-cyclohepta[e]indene-8-carboxylic acid ethyl ester Into a 500 ml flask, the product from step (b) (15.2 mmol) dissolved in toluene (100 ml) was placed. The flask was purged with Ar, followed by the addition of tributyltin hydride (8.36 ml, 31.11 mmol). The reaction mixture was placed in a pre-heated (110° C.) oil bath and stirred for 20 minutes. The reaction mixture was cooled, quenched with saturated aqueous Na$_2$CO$_3$, and extracted with EtOAc (3×). The combined EtOAc extracts were washed with brine, dried over Na$_2$SO$_4$, and solvent evaporated in vacuo to give the crude product. Purification by silica-gel chromatography (gradient elution: 0 to 15% DCM w/20% MeOH, 1% NH$_4$OH in DCM:) gave the sub-title compound as a yellow oil (3.7 g). $^1$H NMR (300 MHz, CDCl$_3$) δ 8.54-8.52 (m, 1H); 8.37-8.33 (m, 1H); 7.23-7.21 (m, 2H); 7.15-7.09 (m, 2H); 4.67 (d, J=19.2, 1H); 4.14-4.08 (m, 2H); 3.69-3.60 (m, 1H); 3.53-3.48 (m, 2H); 3.42-3.34 (m, 2H); 3.21-3.10 (m, 1H); 2.92-2.87 (m, 2H); 2.65-2.58 (m, 1H); 2.52-2.44 (m, 1H); 1.32-1.20 (m, 3H); MS: ESI (positive): 373 (M+1).

d) 2,2-Difluoro-1-pyridin-3-yl-1,2,3,6,7,8,9,10-octahydro-8-aza-cyclohepta[e]indene Into a 250 ml flask, the product from step (c) (3.7 g, 9.9 mmol) dissolved in acetic acid (50 ml) and HBr (33% in acetic acid, 50 ml) was added. The stirred reaction mixture was heated to 60° C. for 6 hours. The reaction mixture was cooled and the volatiles were evaporated in vacuo. The crude product was dissolved in water (100 ml) and washed with diethyl ether (3×). The aqueous layer was basified with 2M NaOH and then extracted with DCM (3×). The combined DCM extracts were washed with brine, dried over Na$_2$SO$_4$, and solvent evaporated in vacuo to give the title compound as tan oil (2.8 g) which solidified over time. $^1$H NMR (300 MHz, CDCl$_3$) δ 8.52 (dd, J=4.5 Hz, J=1.8 Hz, 1H); 8.36-8.35 (m, 1H); 7.29-7.20 (m, 2H); 7.12-7.06 (m, 2H); 4.66 (d, J=18.9 Hz, 1H); 3.47-3.44 (m, 1H); 3.38 (d, J=6.9 Hz, 1H); 2.99-2.85 (m, 4H); 2.74-2.62 (m, 2H); 2.55-2.48 (m, 3H); MS: ESI (positive): 301 (M+1).

Example 29

2,2-Difluoro-1-pyridin-4-yl-1,2,3,6,7,8,9,10-octahydro-8-aza-cyclohepta[e]indene

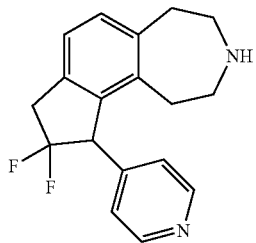

Example 29 was prepared in a similar fashion to Example 28, except 4-bromopyridine was used instead of 3-bromopyridine (Example 28, step (a)). $^1$H NMR (300 MHz, CDCl$_3$) δ 8.55-8.53 (m, 2H); 7.13-7.05 (m, 2H); 6.97-6.95 (m, 2H); 4.62 (d, J=19.5 Hz, 1H); 3.46-3.44 (m, 1H); 3.38 (d, J=6.6 Hz, 1H); 3.00-2.87 (m, 4H); 2.75-2.60 (m, 2H); 2.56-2.46 (m, 2H); 1.96 (bs, 1H). MS: ESI (positive): 301 (M+1).

Example 30

4-Chloro-2,2-difluoro-1-pyridin-3-yl-1,2,3,6,7,8,9,10-octahydro-8-aza-cyclohepta[e]indene

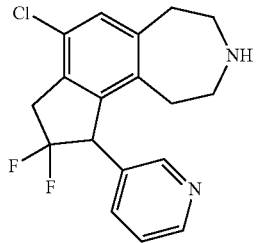 [SMILES: FC1(F)Cc2c(Cl)cc3c(c2C1c1cccnc1)CCNCC3]

Example 30 was prepared in a similar fashion to Example 28, except Intermediate 4 was used as the starting material (Example 28, step (a)). $^1$H NMR (300 MHz, CDCl$_3$) δ 8.55-8.53 (m, 1H); 8.36 (s, 1H); 7.29-7.21 (m, 2H); 7.13 (s, 1H); 4.70 (d, J=19.2 Hz, 1H); 3.59-3.32 (m, 2H); 2.95-2.82 (m, 4H); 2.71-2.56 (m, 2H); 2.50-2.43 (2H); 1.82 (bs, 1H); MS: ESI (positive): 335 (M+1).

Example 31

1-Ethyl-2,2-difluoro-1,2,3,6,7,8,9,10-octahydro-8-aza-cyclohepta[e]indene

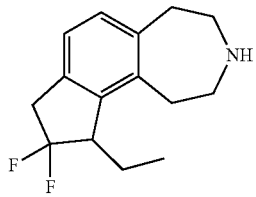

a) 1-Ethylidene-2,2-difluoro-1,3,6,7,9,10-hexahydro-2H-8-aza-cyclohepta[e]indene-8-carboxylic acid ethyl ester Into a glass vial, ethyltriphenylphosphonium bromide (534 mg, 1.43 mmol) dissolved in THF (5 ml) was placed. To this mixture, LHDMS (1M in THF, 1.43 ml, 1.43 mmol) was added. The resulting dark colored solution was stirred at room temperature for 30 minutes, followed by drop-wise addition of the product from Example 14, step (b) (127 mg, 0.411 mmol) in THF (3 ml). The reaction mixture was stirred at 40° C. for 30 minutes. The contents were allowed to cool to room temperature, and water (50 ml) was added. The aqueous mixture was extracted with EtOAc (3×). The combined EtOAc extracts were washed with brine, dried over Na$_2$SO$_4$, and solvent evaporated in vacuo. The crude residue was purified by silica-gel chromatography (gradient elution: 0 to 20% EtOAc in hexanes) to give the sub-title product as a white semi-solid (53 mg). MS: ESI (positive): 322 (M+1).

b) 1-Ethyl-2,2-difluoro-1,3,6,7,9,10-hexahydro-2H-8-aza-cyclohepta[e]indene-8-carboxylic acid ethyl ester Into a 100 ml flask, the product from step (a) dissolved in EtOH (20 ml) was added. The flask was purged with Ar and 10% Pd—C (15 mg) was added. The reaction was stirred over hydrogen (atmospheric pressure) for 16 hours. The reaction mixture was filtered through celite and the solvent evaporated in vacuo. The crude residue was purified by silica-gel chromatography (gradient elution: 0 to 20% EtOAc in hexanes) to give the sub-title product as a colorless oil (42 mg). $^1$H NMR (300 MHz, CDCl$_3$) δ 7.02-6.96 (m, 2H); 4.17 (q, J=7.2 Hz, 2H); 3.65-3.56 (m, 4H); 3.49-3.21 (m, 3H) 2.89-2.83 (m, 4H); 1.76-1.56 (m, 2H); 1.28 (t, J=6.9 Hz, 3H); 0.94 (t, J=7.5 Hz, 3H); MS: ESI (positive): 324 (M+1).

c) 1-Ethyl-2,2-difluoro-1,2,3,6,7,8,9,10-octahydro-8-aza-cyclohepta[e]indene Into a glass vial containing the product from step (b) (42 mg, 0.130 mmol) dissolved in CHCl$_3$ (2 ml), TMSI (176 µL, 1.3 mmol) was added. The stirred reaction mixture was heated to 60° C. for 2 hours. The volatiles were evaporated in vacuo and 2M HCl (2 ml) and water (20 ml) were added. The aqueous mixture was washed with diethyl ether (2×). The aqueous layer was then basified with 2M NaOH to pH 10 and extracted with DCM (3×). The combined DCM extracts were washed with brine, dried over Na$_2$SO$_4$, and solvent evaporated in vacuo give the title compound as a colorless semi-solid (16 mg). $^1$H NMR (300 MHz, CDCl$_3$) 7.00-6.93 (m, 2H); 3.43-3.21 (m, 3H); 2.96-2.86 (m, 8H); 2.20 (bs, 1H); 1.75-1.62 (m, 2H); 0.92 (t, J=7.5 Hz, 3H); MS: ESI (positive): 252 (M+1).

Example 32

2,2-Difluoro-1-methyl-1,2,3,6,7,8,9,10-octahydro-8-aza-cyclohepta[e]indene

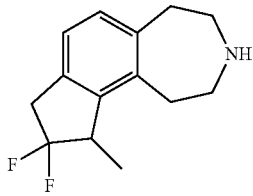

Example 32 was prepared in a similar fashion to Example 31, except methyltriphenylphosphonium bromide was used instead of ethyltriphenylphosphonium bromide (Example 31, step (a)). $^1$H NMR (300 MHz, CDCl$_3$) δ 7.00-6.94 (m, 2H); 3.51-3.22 (m, 3H); 3.01-2.90 (m, 8H); 2.14 (bs, 1H); 1.25-1.20 (m, 3H). MS: ESI (positive): 238 (M+1).

Example 33

1-Benzyl-2,2-difluoro-1,2,3,6,7,8,9,10-octahydro-8-aza-cyclohepta[e]indene

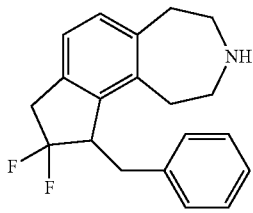

Example 33 was prepared in a similar fashion to Example 31, except benzyltriphenylphosphonium bromide was used instead of ethyltriphenylphosphonium bromide (Example 31, step (a)). $^1$H NMR (300 MHz, CDCl$_3$) δ 7.22-7.19 (m, 3H); 7.00-6.97 (m, 3H); 6.91-6.88 (m, 1H); 3.79-3.68 (m, 1H); 3.23-3.00 (m, 3H); 2.98-2.92 (m, 3H); 2.85-2.78 (m, 3H); 2.70-2.69 (m, 3H); 2.11 (bs, 1H); MS: ESI (positive): 314 (M+1).

Example 34

2,2-Difluoro-1,1-dimethyl-1,2,3,6,7,8,9,10-octahydro-8-aza-cyclohepta[e]indene

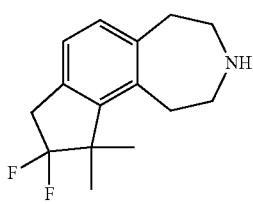

a) 2,2-Difluoro-1-hydroxy-1-methyl-1,3,6,7,9,10-hexahydro-2H-8-aza-cyclohepta[e]indene-8-carboxylic acid ethyl ester Into a glass vial containing Intermediate 3 (200 mg, 0.647 mmol) in diethyl ether (7 ml), methylmagnesium bromide (3M diethyl ether, 2.15 ml, 6.47 mmol) was added at reflux. The reaction mixture was stirred at reflux for 20 minutes. The reaction was cooled, quenched with 10% aqueous NH$_4$Cl, and extracted with EtOAc (3×). The combined EtOAc extracts were washed with brine, dried over Na$_2$SO$_4$, and solvent evaporated in vacuo to give the sub-title compound as a yellow semi-solid (214 mg) that was used without further purification. MS: ESI (positive): 326 (M+1).

b) 1-Chloro-2,2-difluoro-1-methyl-1,3,6,7,9,10-hexahydro-2H-8-aza-cyclohepta[e]indene-8-carboxylic acid ethyl ester Into a glass vial containing the product from step (a) (231 mg, 0.710 mmol) dissolved in SOCl$_2$ (2 ml), pyridine (1 μL, 0.0071 mmol) was added. The stirred reaction mixture was heated to 50° C. for 30 minutes. The volatiles were evaporated in vacuo and the residue diluted with water (50 ml). The aqueous mixture was extracted with EtOAc (3×). The combined EtOAc extracts were washed with brine, dried over Na$_2$SO$_4$, and solvent evaporated in vacuo to give the sub-title compound as a dark yellow oil (214 mg) that was used without further purification. MS: ESI (positive): 344 (M+1).

c) 2,2-Difluoro-1,1-dimethyl-1,3,6,7,9,10-hexahydro-2H-8-aza-cyclohepta[e]indene-8-carboxylic acid ethyl ester Into a glass vial the product from step (b) (214 mg, 0.623 mmol) dissolved in cyclohexane (3 ml) was added. To this solution, AlMe$_3$ (2M in hexanes, 1.2 ml, 2.49 mmol) was added. The reaction mixture was heated to 80° C. and stirred for 1 hour. The reaction mixture was allowed to cool to room temperature and was quenched by the addition of 2M HCl (20 ml). The aqueous mixture was extracted with EtOAc (3×). The combined EtOAc extracts were washed with brine, dried over Na$_2$SO$_4$, and solvent evaporated in vacuo to give the crude product. Purification by silica-gel chromatography (gradient elution: 0 to 20% EtOAc in hexanes) gave the sub-title compound as an orange oil (20 mg). NMR (300 MHz, CDCl$_3$) δ 6.99 (s, 2H); 4.15 (q, J=7.2 Hz, 2H); 3.62-3.59 (m, 4H); 3.29 (t, J=14.1 Hz, 2H); 3.01-2.91 (m, 2H); 1.39 (s, 6H); 1.26 (t, J=7.2 Hz, 3H); MS: ESI (positive): 324 (M+1).

d) 2,2-Difluoro-1,1-dimethyl-1,2,3,6,7,8,9,10-octahydro-8-aza-cyclohepta[e]indene Into a glass vial containing the product from step (c) (20 mg, 0.061 mmol) dissolved in CHCl$_3$ (2 ml), TMSI (84 μL, 0.619 mmol) was added. The reaction mixture was heated to 60° C. for 6 hours. The volatiles were evaporated in vacuo and the residue diluted with 2M HCl (2 ml) and water (20 ml). The aqueous mixture was washed with diethyl ether (2×). The aqueous layer was then basified with 2M NaOH to pH 10 and extracted with DCM (3×). The combined DCM extracts were washed with brine, dried over Na$_2$SO$_4$, and solvent evaporated in vacuo to give the title compound as a colorless oil (4.7 mg). $^1$H NMR (300 MHz, CDCl$_3$) δ 6.99-6.96 (m, 2H); 3.28

(t, J=14.1 Hz, 2H); 3.03-2.90 (m, 8H); 1.89 (bs, 1H); 1.39 (s, 6H); MS: ESI (positive): 252 (M+1).

Example 35

1,1-Dimethyl-4-phenyl-1,2,3,6,7,8,9,10-octahydro-8-aza-cyclohepta[e]indene

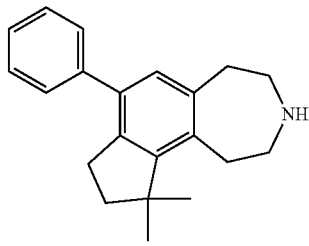 [SMILES: CC1(C)CCc2c(-c3ccccc3)cc3c(c21)CCNCC3]

a) 4-Iodo-1,1-dimethyl-1,3,6,7,9,10-hexahydro-2H-8-aza-cyclohepta[e]indene-8-carboxylic acid propyl ester The product of step (a) was prepared in a similar fashion to Example 13, step (a), except Intermediate 1 was used instead of Intermediate 3. $^1$H NMR (300 MHz, CDCl$_3$) δ 7.35 (s, 1H); 4.15 (q, J=6.9 Hz, 2H); 3.59-3.56 (m, 4H); 2.97-2.94 (m, 2H); 2.83-2.76 (m, 4H); 1.90 (t, J=7.5 Hz, 2H); 1.34 (s, 6H); 1.27 (t, J=7.2 Hz, 3H); MS: ESI (positive): 450 (M+1).

b) 1,1-Dimethyl-4-phenyl-1,3,6,7,9,10-hexahydro-2H-8-aza-cyclohepta[e]indene-8-carboxylic acid propyl ester Into a glass microwave vial, the product from step (a) (166 mg, 0.401 mmol), phenyl boronic acid (59 mg, 0.482 mmol), potassium phosphate tribasic (170 mg, 0.802 mmol), palladium acetate (9 mg, 0.040 mmol), and XPhos (38 mg, 0.080 mmol) in THF (2 ml) were added. The reaction mixture was heated in the microwave to 120° C. for 12 hours and then allowed to cool to room temperature. The mixture was filtered through celite and the filtrate was partitioned between saturated aqueous NaHCO$_3$ and EtOAc. The aqueous layer was extracted with EtOAc (3×). The combined EtOAc extracts were washed with brine, dried over Na$_2$SO$_4$, and solvent evaporated in vacuo to give the crude product. Purification by silica-gel chromatography (gradient elution: 0-20%, EtOAc in hexanes) gave the sub-title compound as a white semi-solid (71 mg). $^1$H NMR (300 MHz, CDCl$_3$) δ 7.41-7.39 (m, 4H); 7.33-7.30 (m, 1H); 7.00 (s, 1H); 4.17 (q, J=6.9 Hz, 2H); 3.67-3.61 (m, 4H); 3.08-3.05 (m, 2H); 2.95-2.93 (m, 2H); 2.84 (t, J=7.2 Hz, 2H); 1.88 (t, J=7.5 Hz, 2H); 1.40 (s, 6H); 1.27 (t, J=6.9 Hz, 3H); MS: ESI (positive): 400 (M+H).

c) 1,1-Dimethyl-4-phenyl-1,2,3,6,7,8,9,10-octahydro-8-aza-cyclohepta[e]indene

Into a glass vial containing the product from step (b) (71 mg, 0.195 mmol) dissolved in CHCl$_3$ (2 ml), TMSI (266 μL, 1.95 mmol) was added. The reaction mixture was heated to 60° C. for 4 hours. The volatiles were evaporated in vacuo and the residue was dissolved in 2M HCl (3 ml) and water (20 ml). The aqueous mixture was washed with diethyl ether (2×). The aqueous layer was then basified with 2M NaOH to pH 10 and extracted with DCM (3×). The combined DCM extracts were washed with brine, dried over Na$_2$SO$_4$, and solvent evaporated in vacuo gave the crude product. Purification by preparative reverse phase HPLC gave the title compound as a colorless oil (9.9 mg). $^1$H NMR (300 MHz, CDCl$_3$) δ 8.66 (bs, 1H); 7.41-7.26 (m, 5H); 7.00 (s, 1H); 3.31-3.15 (m, 8H); 2.84 (t, J=7.5 Hz, 2H); 1.89 (t 7.2 Hz, 2H); 1.33 (s, 6H); MS: ESI (positive): 328 (M+H).

Example 36

1-Ethyl-1,2,7,8,9,10-hexahydro-6H-3-oxa-8-aza-cyclohepta[e]indene

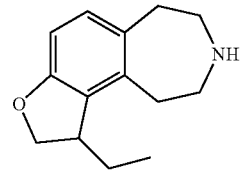 [SMILES: CCC1COc2ccc3c(c21)CCNCC3]

a) 7-Nitro-2,3,4,5-tetrahydro-1H-benzo[d]azepine

To a cooled (0° C.) solution of trifluoroacetic acid (67.2 ml, =869.38 mmol), 2,3,4,5-Tetrahydro-1H-benzo[d]azepine (18 g, 122.44 mmol) was added drop-wise over a period of 20 min. To this, concentrated sulphuric acid (23.4 ml, 440.78 mmol) was added over a period of 45 min at 0° C., and the mixture was stirred for an additional 30 minutes. To this reaction mixture, concentrated nitric acid (8.1 ml, 192.23 mmol) was added drop-wise at 0° C. over a period of 1 h, followed by stirring at room temperature for 2 h. To the reaction mixture, ethyl acetate (250 ml) was added drop-wise at 0° C. The resulting precipitate was filtered and washed with ethyl acetate (100 ml). The crude solid product was added to chloroform (250 ml), washed with 10% sodium hydroxide solution (150 ml), dried over Na$_2$SO$_4$, and concentrated to give the sub-title compound as a light yellow solid (17.4 g). $^1$H NMR (300 MHz, DMSO-d$_6$) δ 7.99-7.93 (m, 2H); 7.38 (d, J=8.1 Hz, 1H); 2.98-2.94 (m, 4H); 2.79-2.76 (m, 4H); MS: ESI (positive): 193 (M+H).

b) 2,2,2-Trifluoro-1-(7-nitro-1,2,4,5-tetrahydrobenzo[d]azepin-3-yl)-ethanone

Into an appropriately sized flask, the product from step (a) (17.4 g, 90.6 mmol) dissolved in DCM (200 ml) was placed. The stirred reaction mixture was cooled to 0° C. and DIEA (23.6 ml, 135.9 mmol) was added, followed by slow addition of TFAA (18.9 ml, 135.9 mmol). The reaction mixture was allowed to warm to room temperature and after 30 minutes the reaction was quenched with 2N HCl (150 ml). The aqueous layer was extracted with DCM (3×). The combined DCM extracts were washed with water, saturated NaHCO$_3$ (2×), brine, dried over Na$_2$SO$_4$, and solvent evaporated in vacuo to give the sub-title compound as a light yellow solid (17.0 g) that was used without further purification. $^1$H NMR (300 MHz, CDCl$_3$) δ 8.06 (d, J=6 Hz, 2H); 7.35 (t, J=8.1 Hz, 1H); 3.85-3.75 (m, 4H); 3.14-3.09 (m, 4H); MS: ESI (positive): 289 (M+H).

c). 1-(7-Amino-1,2,4,5-tetrahydro-benzo[d]azepin-3-yl)-2,2,2-trifluoro-ethanone

Into a 500 ml round bottomed flask, the product from step (b) (17 g) and ammonium formate (17 g) in THF (250 ml)

were added. To the nitrogen purged reaction mixture, 10% Pd—C (4 g) was added. The reaction mixture was stirred at reflux for 3 hours. The reaction mixture was allowed to cool to room temperature and filtered through celite. The filtrate was diluted with water (200 ml) and extracted with EtOAc (3×). The combined EtOAc extracts were washed with saturated NaHCO3, brine, dried over NaSO4, and solvent evaporated in vacuo to give the sub-title compound as an off-white solid (12.9 g). $^1$H NMR (300 MHz, DMSO-d$_6$) δ 6.83-6.78 (m, 1H); 6.39-6.31 (m, 2H); 4.91 (s, 2H); 3.66-3.56 (m, 4H); 2.81-2.73 (m, 4H); MS: ESI (positive): 259 (M+H).

d) 2,2,2-Trifluoro-1-(7-hydroxy-1,2,4,5-tetrahydro-benzo[d]azepin-3-yl)-ethanone Into a 250 ml flask, the product of step (c) (2 g, 7.75 mmol) dissolved in water (8.5 ml) and concentrated H$_2$SO$_4$ (1.5 ml) was added. The stirred mixture was heated to 70° C., followed by the addition of a solution NaNO$_2$ (615 mg, 8.91 mmol) in water (20 ml). The reaction mixture was stirred at 70° C. for 1 hour. The mixture was then allowed to cool to room temperature and diluted with water (50 ml). The aqueous mixture was extracted with EtOAc (3×). The combined EtOAc extracts were washed with brine, dried over Na$_2$SO$_4$, and solvent evaporated in vacuo to give the sub-title compound as a brown solid (1.8 g) that was used without further purification. MS: ESI (positive): 260 (M+H).

e) 1-(7-Bromo-8-hydroxy-1,2,4,5-tetrahydro-benzo[d]azepin-3-yl)-2,2,2-trifluoro-ethanone Into a 100 ml flask, the product of step (d) (1.65 g, 6.37 mmol) dissolved in acetonitrile (25 ml) was added. To this stirred solution, NBS (1.07 g, 6.05 mmol) was added. The reaction mixture was heated to 80° C. for 15 minutes and then partitioned between water and EtOAc. The aqueous layer was extracted with EtOAc (3×). The combined EtOAc extracts were washed with brine, dried over Na$_2$SO$_4$, and solvent evaporated in vacuo to give the crude product. Purification by silica-gel chromatography (gradient elution: 0 to 40% EtOAc in hexanes) gave the sub-title compound as a yellow solid (1.4 g). MS: ESI (positive): 338, 340 (M+H).

f) 1-(8-Bromo-7-hydroxy-6-iodo-1,2,4,5-tetrahydro-benzo[d]azepin-3-yl)-2,2,2-trifluoro-ethanone Into a 100 ml flask, the product of step (e) (1.03 g, 3.05 mmol) dissolved in TFA (10 ml) was added. To this stirred solution, NIS (828 mg, 3.68 mmol) was added. The reaction mixture was stirred at room temperature for 45 minutes, then carefully poured over ice-cold saturated aqueous NaHCO$_3$ (200 ml). The aqueous mixture was extracted with EtOAc (3×). The combined EtOAc extracts were washed with brine, dried over Na$_2$SO$_4$, and solvent evaporated in vacuo to give the crude product. Purification by silica-gel chromatography (gradient elution: 0 to 30% EtOAc in hexanes) gave the sub-title compound as a yellow solid (166 mg). $^1$H NMR (300 MHz, CDCl$_3$) δ 7.29 (s, 1H); 5.99 (s, 1H); 3.76-3.67 (m, 4H); 3.33-3.30 (m, 2H); 3.00-2.96 (m, 2H); MS: ESI (positive): 464, 466 (M+H).

g) 1-(8-Bromo-7-but-2-enyloxy-6-iodo-1,2,4,5-tetrahydro-benzo[d]azepin-3-yl)-2,2,2-trifluoro-ethanone Into a glass vial containing the product from step (I) (166 mg, 0.358 mmol) dissolved in DMF (3 ml), K$_2$CO$_3$ (247 mg, 1.79 mmol) was added, followed by crotyl bromide (110 μL, 1.075 mmol). The reaction mixture was stirred at room temperature for 1 hour. The reaction mixture was diluted with water (50 ml) and extracted with EtOAc (3×). The combined EtOAc extracts were washed with brine, dried over Na$_2$SO$_4$, and solvent evaporated in vacuo to give the crude product. Purification by silica-gel chromatography (gradient elution: 0 to 20% EtOAc in hexanes) gave the sub-title compound as a colorless oil (155 mg). $^1$H NMR (300 MHz, CDCl$_3$) δ 7.32 (d, J=9.9 Hz, 1H); 5.93-5.89 (m, 2H); 4.44-4.42 (m, 2H); 3.78-3.67 (m, 4H); 3.35-3.30 (m, 2H); 3.00-2.97 (m, 2H); 1.78 (d, J=4.8 Hz, 3H); MS: ESI (positive): 518, 520 (M+H).

h) 1-(4-Bromo-1-ethyl-1,2,6,7,9,10-hexahydro-3-oxa-8-aza-cyclohepta[e]inden-8-yl)-2,2,2-trifluoro-ethanone Into a 100 ml flask containing the product of step (g) (642 mg, 1.24 mmol) dissolved in EtOH (20 ml), TEA (1.7 ml, 12.4 mmol), hypophosphorous acid (2.3 ml, 12.4 mmol), and AIBN (407 mg, 2.48 mmol) were added. The reaction mixture was heated to 90° C. for 30 minutes, and then the volatiles were evaporated in vacuo. The resulting residue was diluted with water (100 ml) and extracted with DCM (3×). The combined DCM extracts were washed with brine, dried over Na$_2$SO$_4$, and solvent evaporated in vacuo to give the crude product. Purification by silica-gel chromatography (gradient elution: 0 to 30% EtOAc in hexanes) gave the sub-title compound as a white solid that was contaminated with AIBN. This material was used as obtained in the next step. MS: ESI (positive): 392, 394 (M+H).

i) 1-(1-Ethyl-1,2,6,7,9,10-hexahydro-3-oxa-8-aza-cyclohepta[e]inden-8-yl)-2,2,2-trifluoro-ethanone Into a 100 ml flask containing the product from step (h) dissolved in EtOH (20 ml), 10% Pd—C (1 g) was added. The reaction was stirred over hydrogen (atmospheric pressure) for 2 hours. The mixture was filtered through celite and the solvent evaporated in vacuo. The crude product residue was diluted with 2M HCl (100 ml) and extracted with EtOAc (3×). The combined EtOAc extracts were washed with brine, dried over Na$_2$SO$_4$, and solvent evaporated in vacuo. The residue was purified by silica-gel chromatography (gradient elution: 0 to 20% EtOAc in hexanes) to give the sub-title compound as a white semi-solid (140 mg). $^1$H NMR (300 MHz, CDCl$_3$) δ 6.91 (t, J=8.1 Hz, 1H); 6.60-6.56 (m, 1H); 4.52-4.38 (m, 2H); 3.78-3.65 (m, 4H); 3.33-3.24 (m, 1H); 2.94-2.87 (m, 4H); 1.63-1.49 (m, 2H); 0.99-0.90 (m, 3H); MS: ESI (positive): 314 (M+H).

j) 1-Ethyl-1,2,7,8,9,10-hexahydro-6H-3-oxa-8-aza-cyclohepta[e]indene

The product of step (i) (45 mg, 0.143 mmol) was dissolved in an appropriately sized flask in MeOH (3 ml). To this mixture water (1 ml) and K$_2$CO$_3$ (500 mg, 3.62 mmol) were added. The reaction mixture was stirred at room temperature until the product formation was complete by LCMS. The reaction mixture was diluted with water (>10× total volume) and extracted with DCM (3×). The combined DCM extracts were washed with brine, dried (Na$_2$SO$_4$), and solvent evaporated in vacuo to provide the title compound (15.8 mg). $^1$H NMR (300 MHz, CDCl$_3$) δ 6.86 (d, J=7.8 Hz, 1H); 6.52 (d, J=8.1 Hz, 1H); 4.49-4.44 (m, 1H); 4.39-4.35 (m, 1H); 3.31-

3.21 (m, 1H); 2.99-2.85 (m, 8H); 2.07 (bs, 1H); 1.58-1.52 (m, 2H); 0.92 (t, J=7.5 Hz, 3H). MS: ESI (positive): 218 (M+H).

Example 37

1-Ethyl-2,3,8,9,10,11-hexahydro-1H,7H-4-oxa-9-aza-cyclohepta[a]naphthalene

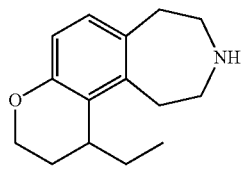 [SMILES: CCC1CCOc2ccc3c(c21)CCNCC3]

a) 7-Nitro-1,2,4,5-tetrahydro-benzo[d]azepine-3-carboxylic acid ethyl ester

To a stirred solution of the product from Example 36, step (a) (5 g, 26.0 mmol) dissolved in DCM (75 ml), DIEA (6.8 ml, 39 mmol) was added. The reaction mixture was cooled to 0° C. and ethyl chloroformate was added (3.0 ml, 31.2 mmol). The reaction mixture was stirred at 0° C. for 2 hours and then allowed to warm to room temperature. The reaction mixture was diluted with 2N HCl (150 ml) and extracted with DCM (3×). The combined DCM extracts were washed with brine, dried over $Na_2SO_4$, and solvent evaporated in vacuo to give the crude product. Purification by silica-gel chromatography (gradient elution: 0 to 50% EtOAc in hexane) gave the sub-title compound as a light yellow solid (4.7 g). $^1$H NMR (300 MHz, DMSO-$d_6$) δ 8.07 (d, J=2.4 Hz, 1H); 8.01 (dd, J=8.1 Hz, 2.4 Hz, 1H); 7.45 (d, J=8.1 Hz, 1H); 4.07 (q, J=6.9 Hz, 2H); 3.54-3.51 (m, 4H); 3.04-3.01 (m, 4H); 1.19 (t, J=7.2 Hz, 3H).

b). 7-Amino-1,2,4,5-tetrahydro-benzo[d]azepine-3-carboxylic acid ethyl ester

Into a Parr hydrogenation bottle, the product from step (a) (17 g) dissolved in EtOAc (200 ml) was added. To the Ar purged bottle 10% Pd—C (1.7 g) was added. The reaction mixture was shaken under hydrogen (50 psi) for 3 hours. The reaction mixture was filtered through celite and solvent evaporated in vacuo to give the sub-title compound as an off-white solid (12.9 g). $^1$H NMR (300 MHz, CDCl$_3$) δ 6.77 (d, J=7.8 Hz, 1H); 6.35 (s, 1H); 6.30 (d, J=8.1 Hz, 1H); 4.84 (s, 2H); 4.06 (q, J=6.9 Hz, 2H); 3.43 (bs, 4H); 2.66 (bs, 4H); 1.19 (t, 7.2 Hz, 3H). MS: ESI (positive): 235 (M+H).

c) 7-Hydroxy-1,2,4,5-tetrahydro-benzo[d]azepine-3-carboxylic acid ethyl ester

Into a 250 ml flask, the product from step (b) (3 g, 12.82 mmol) dissolved in water (15 ml) and concentrated $H_2SO_4$ (1.02 ml, 19.23 mmol) was added The reaction mixture was heated to 70° C. and stirred for 15 minutes. A solution of $NaNO_2$ (1.01 g, 14.74 mmol) in water (30 ml) was quickly added, followed by addition of THF (45 ml). The reaction mixture was stirred at 70° C. for 30 minutes and then allowed to cool to room temperature. The reaction mixture was extracted with EtOAc (3×). The combined EtOAc extracts were washed with brine, dried over $Na_2SO_4$, and solvent evaporated in vacuo to give the sub-title compound as a yellow solid (2.0 g) that was used without further purification. MS: ESI (positive): 236 (M+H).

d) 7-Hydroxy-8-iodo-1,2,4,5-tetrahydro-benzo[d]azepine-3-carboxylic acid ethyl ester Into a 100 ml flask, the product of step (c) (503 mg, 2.14 mmol) dissolved in acetonitrile (20 ml) and TFA (2 ml) was added. To this stirred solution, NIS (458 mg, 2.03 mmol) was added. After stirring for 30 minutes at room temperature, the reaction was diluted with water (200 ml) and extracted with EtOAc (3×). The combined EtOAc extracts were washed with brine, dried over $Na_2SO_4$, and solvent evaporated in vacuo to give the crude product. Purification by silica-gel chromatography (gradient elution: 0 to 40% EtOAc in hexanes) gave the sub-title compound as a yellow solid (616 mg). $^1$H NMR (300 MHz, CDCl$_3$) δ 7.39 (s, 1H); 6.77 (s, 1H); 5.42 (bs, 1H); 4.18 (q, J=7.2 Hz, 2H); 3.61-3.52 (m, 4H); 2.81-2.72 (m, 4H); 1.26 (t, J=6.9 Hz, 3H); MS: ESI (positive): 362 (M+H).

e). 7-(2-Carboxy-ethoxy)-8-iodo-1,2,4,5-tetrahydro-benzo[d]azepine-3-carboxylic acid ethyl ester Into a 100 ml flask, the product of step (d) (1.28 g, 3.54 mmol) dissolved in DMF (15 ml) was added. The solution was cooled to 0° C. and NaH (354 mg, 8.86 mmol) was added, followed by 3-iodopropionic acid (1.06 g 5.31 mmol). The reaction mixture was allowed to warm to room temperature and stirred for 1.5 hours, after which time it was heated to 70° C. for an additional 1 hour. The reaction mixture was cooled to room temperature and quenched by the addition of water (100 ml) and 2M NaOH (15 ml). The aqueous mixture was washed with EtOAc (2×), acidified with 2M HCl to pH 2, and extracted with EtOAc (3×). The combined EtOAc extracts were washed with brine, dried over $Na_2SO_4$, and solvent evaporated in vacuo to give crude product. Purification by silica-gel chromatography (gradient elution: 0 to 60% EtOAc in hexanes) gave the sub-title compound as an off-white solid (580 mg) and recovered starting material (515 mg). MS: ESI (positive): 434 (M+H).

f) 5-Iodo-1-oxo-2,3,7,8,10,11-hexahydro-1H-4-oxa-9-aza-cyclohepta[a]naphthalene-9-carboxylic acid ethyl ester Into a 100 ml flask, the product from step (e) (312 mg, 0.72 mmol) dissolved in DCM (20 ml) was added. The solution was cooled to 0° C., and oxalyl chloride (94 μL, 1.07 mmol) was added, followed by 2 drops of DMF. After 30 minutes, volatiles were evaporated in vacuo and the residue was dissolved in fresh DCM (20 ml) and cooled to 0° C. Aluminum chloride (386 mg, 2.88 mmol) was then added and the reaction mixture stirred for 1 hour. The reaction was quenched with saturated aqueous NH$_4$Cl, and the organic layer was extracted with DCM (3×). The combined DCM extracts were washed with brine, dried over $Na_2SO_4$, and solvent evaporated in vacuo to give the crude product. Purification by silica-gel chromatography (gradient elution: 0 to 40% EtOAc in hexanes) gave the sub-title compound as a light yellow solid (170 mg). $^1$H NMR (300 MHz, CDCl$_3$) δ 7.69 (s, 1H); 4.56 (t, J=6.3 Hz, 2H); 4.12 (q, J=7.2 Hz, 2H); 3.68-3.51 (m, 6H); 2.85 (t, J=6.6 Hz, 4H); 1.23 (t, J=7.2 Hz, 3H); MS: ESI (positive): 416 (M+H).

g). 1-Ethyl-1-hydroxy-5-iodo-2,3,7,8,10,11-hexahydro-1H-4-oxa-9-aza-cyclohepta[a]naphthalene-9-carboxylic acid ethyl ester Into a glass vial containing the product from step (f) (170 mg, 0.409 mmol) dissolved in diethyl ether (4 ml), ethylmagnesium bromide (3M diethyl ether, 1.3 ml, 4.09 mmol) was added at reflux. The reaction mixture was stirred at reflux for 20 minutes. The reaction mixture was allowed to cool to room temperature and was then quenched with saturated aqueous NH₄Cl (30 ml). The aqueous mixture was extracted with EtOAc (3×). The combined EtOAc extracts were washed with brine, dried over Na₂SO₄, and solvent evaporated in vacuo to give a yellow oil (197 mg) that was used without further purification. MS: ESI (positive): 446 (M+H).

h). 1-Ethyl-5,7,8,10,11-hexahydro-1H-4-oxa-9-aza-cyclohepta[a]naphthalene-9-carboxylic acid ethyl ester Into a glass vial containing the product from step (g) (197 mg) dissolved in DCM (2 ml) triethylsilane (594 μL, 3.71 mmol) was added at 0° C., followed by boron trifluoride etherate (287 μL, 2.32 mmol). After stirring at 0° C. for 20 minutes, the reaction was quenched with saturated aqueous NaHCO₃ and the aqueous layer was extracted with DCM (3×). The combined DCM extracts were washed with brine, dried over Na₂SO₄, and solvent evaporated in vacuo to give the crude product. Purification by silica-gel chromatography (gradient elution: 0-30% EtOAc in hexanes) gave the sub-title compound as a colorless oil (145 mg). MS: ESI (positive): 430 (M+H).

i) 1-Ethyl-2,3,7,8,10,11-hexahydro-1H-4-oxa-9-aza-cyclohepta[a]naphthalene-9-carboxylic acid ethyl ester Into a Parr hydrogenation bottle, the product of step (h) (145 mg) dissolved in EtOH (15 ml) and AcOH (5 ml) was added. To this solution, 10% Pd—C (20 mg) was added. The mixture was shaken over hydrogen (50 psi) at 50° C. for 2 hours. The reaction mixture was filtered through celite and the solvent was evaporated in vacuo. The residue was diluted with saturated aqueous Na₂CO₃ and extracted with EtOAc (3×). The combined EtOAc extracts were washed with brine, dried over Na₂SO₄, and solvent evaporated in vacuo to give the sub-title compound (95 mg) that was used without further purification. MS: ESI (positive): 304 (M+H).

j) 1-Ethyl-2,3,8,9,10,11-hexahydro-1H,7H-4-oxa-9-aza-cyclohepta[a]naphthalene

Into a sealed tube, the product from step (i) (95 mg, 0.313 mmol) dissolved in EtOH (2 ml) and water (500 μl) was added. To this stirred solution, KOH (275 mg, 4.9 mmol) was added. The reaction mixture was heated to 120° C. for 24 hours. The reaction mixture was allowed to cool to room temperature and was diluted with 2M HCl (15 ml) and water (15 ml). The aqueous mixture was washed with EtOAc (2×). The aqueous layer was then basified with 2M NaOH to pH 10 and extracted with DCM (3×). The combined DCM extracts were washed with brine, dried over Na₂SO₄, and solvent evaporated in vacuo to give the title compound as a yellow oil (40 mg). $^1$H NMR (300 MHz, CDCl₃) δ 6.86 (d, J=8.1 Hz, 1H); 6.57 (d, J=8.1 Hz, 1H); 4.22-4.17 (m, 1H); 4.12-4.03 (m, 1H); 3.00-2.84 (m, 8H); 2.83-2.72 (m, 1H); 2.06 (bs, 1H); 1.97-1.92 (m, 2H); 1.56-1.45 (m, 2H); 1.01 (t, J=6.0 Hz, 3H); MS: ESI (positive): 232 (M+H).

Example 38

2,2-Difluoro-1-methoxy-1,2,3,6,7,8,9,10-octahydro-8-aza-cyclohepta[e]indene

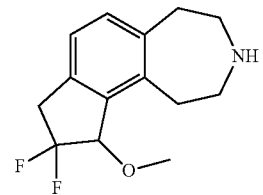 [SMILES: COC1c2c(ccc3c2CCNCC3)CC1(F)F]

a) 2,2-Difluoro-3,6,7,8,9,10-hexahydro-2H-8-aza-cyclohepta[e]inden-1-one

The product from Example 14, step (b) (0.20 g, 0.65 mmol) was dissolved in acetic acid (5 ml). To this solution was added 33% HBr in acetic acid (5 ml). The stirred reaction mixture was heated to 60° C. for 6 hours. Volatiles were evaporated in vacuo and the residue diluted with water. The aqueous mixture was washed with diethyl ether (2×). The pH of the aqueous layer was then adjusted to 10-12 by addition of 2M NaOH. The aqueous mixture was then extracted with DCM (3×). The combined DCM extracts were washed with brine, dried (Na₂SO₄), and solvent evaporated in vacuo to give the sub-title compound as a tan solid (132 mg) that was used in the next step without further purification. MS: ESI (positive): 238 (M+H).

b). 2,2-Difluoro-1-oxo-1,3,6,7,9,10-hexahydro-2H-8-aza-cyclohepta indene-8-carboxylic acid benzyl ester To a stirred solution of the product from step (a) (0.13 g, 0.56 mmol) dissolved in DCM (5 ml) at 0° C. was added DIEA (0.12 ml, 0.67 mmol) and benzyl chloroformate (0.095 ml, 0.67 mmol). The reaction mixture was allowed to stir at RT for 1 hour. The reaction mixture was diluted with 1N HCl and extracted with DCM (3×). The combined DCM extracts were washed with brine, dried (Na₂SO₄), and solvent evaporated in vacuo to give the crude product which was purified by flash silica-gel chromatography (gradient elution: 0-40% EtOAc in hexanes) to give the sub-title compound as a colorless oil (180 mg). MS: ESI (positive): 372 (M+H).

c). 2,2-Difluoro-1-hydroxy-1,3,6,7,9,10-hexahydro-2H-8-aza-cyclohepta[e]indene-8-carboxylic acid benzyl ester To a stirred solution of the product from step (b) (0.18 g, 0.49 mmol) dissolved in ethanol (2 ml) was added NaBH₄ (0.046, 1.21 mmol). The reaction mixture was allowed to stir at RT for 1 hour. The reaction mixture was diluted with water and extracted with DCM (3×). The combined DCM extracts were washed with brine, dried (Na₂SO₄), and solvent evaporated in vacuo to give the sub-titled compound as a white semi-solid (0.13 g) which was used as obtained in the next step. MS: ESI (positive): 374 (M+H).

d). 2,2-Difluoro-1-methoxy-1,3,6,7,9,10-hexahydro-2H-8-aza-cyclohepta[e]indene-8-carboxylic acid benzyl ester To a stirred solution of the product from step (c) (0.13 g, 0.35 mmol) dissolved in THF (2 ml) at 0° C. was added NaH (0.046, 0.86 mmol). The reaction mixture was allowed to stir for 10 minutes followed by the addition of methyl iodide (0.053 mL, 0.86 mmol). The reaction mixture was stirred at RT for 24 hours. The reaction mixture was diluted with water and extracted with ethyl acetate (3×). The combined ethyl acetate extracts were washed with brine, dried ($Na_2SO_4$), and solvent evaporated in vacuo to give the sub-titled compound as a yellow oil (0.10 g). MS: ESI (positive): 388 (M+H).

e). 2,2-Difluoro-1-methoxy-1,2,3,6,7,8,9,10-octahydro-8-aza-cyclohepta[e]indene The product from step (d) was purified and deprotected according to the chiral HPLC section below to give the titled compound. $^1$H NMR (300 MHz, $CDCl_3$) δ 10.10 (bs, 1H); 7.15 (d, J=6.6 Hz, 1H); 7.06 (d, J=6.6 Hz, 1H); 4.70 (d, J=12.3 Hz, 1H); 3.63 (s, 3H); 3.57-3.25 (m, 10H); MS: ESI (positive): 254 (M+H).

Example 39

1-Phenyl-7,8,9,10-tetrahydro-6H-3-oxa-8-aza-cyclohepta[e]indene

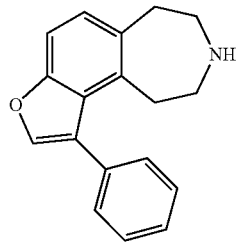 [SMILES: c1ccc(-c2coc3ccc4c(c23)CCNCC4)cc1]

a). 2,2,2-Trifluoro-1-(7-hydroxy-8-iodo-1,2,4,5-tetrahydro-benzo[d]azepin-3-yl)-ethanone Chloroform (6 ml) was added to a round bottom flask containing the product from step (d) (0.800 g, 3.0 mmol) example 36. To the stirred solution was added TFA (1.5 ml) and NIS (0.765 g, 3.4 mmol, 1.1 eq). The reaction mixture was stirred at room temperature for 30 minutes and then poured over ice. The mixture was extracted with dichloromethane (3×). The organic layers were combined and washed with saturated sodium thiosulfate, followed by saturated sodium bicarbonate, and brine. Purification by silica-gel chromatography (gradient elution: 0-100% EtOAc in hexanes) gave the sub-title compound as a white solid (528 mg). MS: ESI (positive): 385 (M+H).

b). 2,2,2-Trifluoro-1-[7-iodo-8-(2-oxo-2-phenyl-ethoxy)-1,2,4,5-tetrahydro-benzo[d]azepin-3-yl]-ethanone Dry acetone (6 ml) was added to a flask containing the product from step (a) (0.528 g, 1.3 mmol). To this was added 2-Bromo-1-phenyl-ethanone (0.327 g, 1.6 mmol, 1.2 eq) and potassium carbonate (0.378 g, 2.7 mmol, 2.0 eq). The reaction mixture was allowed to stir for 16 hours at room temperature. The acetone was removed under vacuum and the solid was dissolved in dichloromethane, washed with 4N HCl, and brine. Purification by silica-gel chromatography (gradient elution: 0-100% EtOAc in hexanes) gave the sub-title compound as a white solid (552 mg). MS: ESI (positive): 504 (M+H).

c). 4-Iodo-1-phenyl-7,8,9,10-tetrahydro-6H-3-oxa-8-aza-cyclohepta[e]indene

Poly phosphoric acid (~1 ml) was added to a vial containing the product from step (b) (0.255 g, 0.50 mmol) and heated to 90° C. for 20 minutes. Water was added to the reaction mixture and extracted with dichloromethane (3×). The organic layers were washed with saturated sodium bicarbonate, and brine. To the crude material was added 8 ml of methanol, 5 ml of water, and potassium carbonate (~100 mg). The reaction mixture was allowed to stir at room temperature for 16 hours. The reaction mixture was concentrated and to this was added 2N HCl, and extracted with dichloromethane (3×). Purification by silica-gel chromatography (gradient elution: 0-20% methanol in dichloromethane) gave the sub-title compound as an off white solid (0.034 mg). MS: ESI (positive): 390 (M+H).

d) 1-Phenyl-7,8,9,10-tetrahydro-6H-3-oxa-8-aza-cyclohepta[e]indene

To a solution of ethanol (5 ml) was added the product from step (c) (0.034 g, 0.09 mmol) and Pd/C (0.07 g). The reaction vessel was placed under hydrogen atmosphere and purged 3×. Hydrogen was added and the reaction was stirred at atmospheric pressure for 18 hours. The reaction mixture was filtered over celite and the ethanol was removed under vacuum. No further purification was needed. The sub-title compound was isolated as a white solid (6.4 mg). $^1$H NMR (300 MHz, $CDCl_3$) δ 7.549 (s, 1H); 7.44-7.32 (m, 6H); 7.13 (d, J=8.4 Hz, 1H); 3.28-3.11 (m, 8H); MS: ESI (positive): 264 (M+H).

Example 40

1-Thiazol-2-yl-1,2,3,6,7,8,9,10-octahydro-8-aza-cyclohepta[e]indene

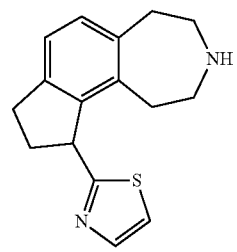 [SMILES: c1csc(C2CCc3ccc4c(c32)CCNCC4)n1]

a) 1-Thiazol-2-yl-1,2,3,6,7,8,9,10-octahydro-8-aza-cyclohepta[e]inden-1-ol

To a stirred solution of 2-bromothiazole (0.66 ml, 7.32 mmol) in THF (20 ml) was added isopropyl magnesium chloride (2M, 3.7 ml, 7.32 mmol). The reaction mixture was heated to 60° C. for 6 hours. The reaction mixture was then cooled to RT and a solution of intermediate 3 (0.20 g, 0.73 mmol) in THF (2 ml) was added. The reaction was heated to 60° C. for 1 hour and then cooled to RT and stirred overnight. The reaction mixture was quenched by addition of saturated ammonium chloride (~75 ml) and extracted with DCM (3×). The combined DCM extracts were washed with brine, dried ($Na_2SO_4$), and solvent evaporated in vacuo to give the crude product as a dark solid. Purification by flash silica-gel chromatography (gradient elution: 0-100% EtOAc in hexanes) gave the sub-title compound (0.21 g) as a yellow oil. MS: ESI (positive): 287 (M+H).

b) 2,2,2-Trifluoro-1-(1-hydroxy-1-thiazol-2-yl-1,3,6,7,9,10-hexahydro-2H-8-aza-cyclohepta[e]inden-8-yl)-ethanone To a stirred solution of the product from step (a) (0.32 g, 1.13 mmol) in DCM (5 ml) at 0° C. was added DIEA (0.22 ml, 1.24 mmol) and TFAA (0.18 ml, 1.24 mmol). The reaction mixture was stirred at 0° C. for 10 minutes and then allowed to warm to RT. The reaction mixture was stirred at RT for 30 minutes after which time TLC showed no starting material. The reaction mixture was then diluted with water (30 ml). The mixture was then extracted into DCM (3×). The combined DCM extracts were washed with brine, dried ($Na_2SO_4$), and solvent evaporated in vacuo to give the sub-titled compound as a tan oil that was used without purification in the next step. MS: ESI (positive): 383 (M+H).

c) 2,2,2-Trifluoro-1-(1-thiazol-2-yl-6,7,9,10-tetrahydro-3H-8-aza-cyclohepta[e]inden-8-yl)-ethanone The product from step (b) (1.13 mmol) was dissolved in 4N HCl/dioxane and heated to 60° C. for 1 hour after which time LCMS indicated no starting material. The reaction mixture was cooled to RT and the solvent was evaporated in vacuo to give the crude product as a brown semi-solid. Purification by flash silica-gel chromatography (gradient elution: 0-50% EtOAc in hexanes) gave the sub-title compound (22 mg) as a yellow oil. MS: ESI (positive): 365 (M+H).

d) 2,2,2-Trifluoro-1-(1-thiazol-2-yl-1,3,6,7,9,10-hexahydro-2H-8-aza-cyclohepta[e]inden-8-yl)-ethanone The product from step (c) (22 mg) was dissolved in ethanol (30 ml) placed in a Parr Hydrogenation bottle. To this solution was added 10% Pd—C (100 mg). The mixture was shaken at 50° C. over 50 psi of hydrogen for 16 hours. The reaction mixture was purged with Nitrogen, cooled to RT, and filtered thru a pad of celite. The solvent was evaporated in vacuo to give the crude product as a light yellow oil. Purification by flash silica-gel chromatography (gradient elution: 0-50% EtOAc in hexanes) gave the sub-title compound (17 mg) as a white film. MS: ESI (positive): 367 (M+H).

e) 1-Thiazol-2-yl-1,2,3,6,7,8,9,10-octahydro-8-aza-cyclohepta[e]indene

The product from step (d) was purified and deprotected according to the chiral HPLC section below to give the titled compound. $^1$H NMR (300 MHz, $CDCl_3$) δ 7.68 (d, 3.3 Hz, 1H); 7.14 (d, J=3.3 Hz, 1H); 7.08 (d, J=7.5 Hz, 1H); 7.04 (d, J=7.5 Hz, 1H); 4.91 (dd, J=1.8 Hz, 8.7 Hz, 1H); 3.22-3.10 (m, 1H); 3.03-2.81 (m, 8H); 2.78-2.56 (m, 2H); 2.40-2.32 (m, 1H); MS: ESI (positive): 271 (M+H).

Example 41

1-Ethoxy-2,2-difluoro-1,2,3,6,7,8,9,10-octahydro-8-aza-cyclohepta[e]indene

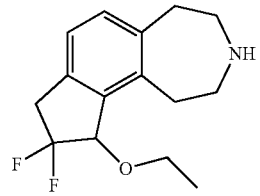 [SMILES: CCOC1c2c(ccc3c2CCNCC3)CC1(F)F]

Example 41 was prepared in a similar fashion to Example 38, except iodoethane used instead of iodomethane (Example 38, step (d)). $^1$H NMR (300 MHz, $CDCl_3$) δ 7.07 (d, 7.5 Hz, 1H); 6.95 (d, J=7.5 Hz, 1H); 4.75 (d, J=12.9 Hz, 1H); 4.03-3.93 (m, 1H); 3.76-3.66 (m, 1H); 3.59-3.42 (m, 1H); 3.34-3.21 (m, 1H); 2.97-2.88 (m, 8H); 1.26 (t, J=7.2 Hz, 3H); MS: ESI (positive): 268 (M+1).

Example 42

2,2-Difluoro-1,2,3,6,7,8,9,10-octahydro-8-aza-cyclohepta[e]indene

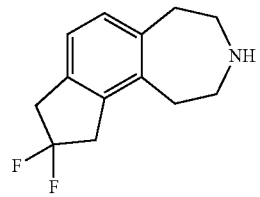 [SMILES: FC1(F)Cc2ccc3c(c2C1)CCNCC3]

a). 2,2-Difluoro-1-hydroxy-1,3,6,7,9,10-hexahydro-2H-8-aza-cyclohepta[e]indene-8-carboxylic acid ethyl ester To a stirred solution of the product from Example 14, step (b) (0.10 g, 0.32 mmol) in ethanol (5 ml) was added $NaBH_4$ (30 mg, 0.79 mmol). The reaction mixture was allowed to stir at RT for 1 hour. The reaction mixture was diluted with water and extracted with DCM (3×). The combined DCM extracts were washed with brine, dried ($Na_2SO_4$), and solvent evaporated in vacuo to give the sub-titled compound as a white semi-solid (92 mg) which was used as obtained in the next step. MS: ESI (positive): 312 (M+H).

b). 1-Chloro-2,2-difluoro-1,3,6,7,9,10-hexahydro-2H-8-aza-cyclohepta[e]indene-8-carboxylic acid ethyl ester To a stirred solution of the product from step (a) (25 mg) in $SOCl_2$ (1 ml) was added pyridine (1 ml). The mixture was heated to 70° C. for 30 minutes after which LCMS indicates no starting material. The volatiles were evaporated in vacuo. The residue was dissolved in EtOAc and washed with 1 M citric acid, saturated $NaHCO_3$, brine, dried ($Na_2SO_4$), and solvent evaporated in vacuo to give the sub-titled compound (21 mg) as a colorless oil which was used as obtained in the next step. MS: ESI (positive): 330 (M+H).

c). 2,2-Difluoro-1,3,6,7,9,10-hexahydro-2H-8-aza-cyclohepta[e]indene-8-carboxylic acid ethyl ester The product from step (b) (21 mg) was dissolved in EtOAc (40 ml) and placed in a parr hydrogenation bottle. To this solution was added 5% Pd—C (10 mg). The mixture was shaken under 50 psi of hydrogen for 2 hours after which LCMS indicated no starting material. The mixture was purged with Nitrogen and filtered thru a bed of celite. The solvent was evaporated in vacuo to give the sub-titled compound (20 mg) as a yellow oil. MS: ESI (positive): 296 (M+H).

d). 2,2-Difluoro-1,2,3,6,7,8,9,10-octahydro-8-aza-cyclohepta[e]indene

To a stirred solution of the product from step (c) (20 mg, 0.07 mmol) in chloroform (2 ml) was added TMSI (0.092 ml, 0.7 mmol). The reaction mixture was heated to 60° C. for 6 hours after which LCMS indicated no starting material. The reaction mixture was cooled to RT and the volatiles were removed in vacuo. The residue was dissolved in 1N HCl (10 ml) and washed with diethyl ether (3×). The aqueous layer pH was then adjusted to 12 by addition of 2M NaOH. The aqueous mixture was then extracted with DCM (3×). The combined DCM extracts were washed with brine, dried (Na$_2$SO$_4$), and solvent evaporated in vacuo to give the titled compound as a colorless oil (9 mg). $^1$H NMR (300 MHz, CDCl$_3$) δ 6.99 (d, J=7.8 Hz, 1H); 6.96 (d, 7.8 Hz, 1H); 3.47-3.34 (m, 4H); 2.98-2.82 (m, 8H); 2.09 (bs, 1H); MS: ESI (positive): 224 (M+1).

Example 43

1-Methoxy-1,2,3,6,7,8,9,10-octahydro-8-aza-cyclo-hepta[e]indene

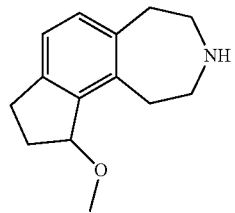 [SMILES: COC1CCc2ccc3c(c21)CCNCC3]

a). 1-Hydroxy-1,3,6,7,9,10-hexahydro-2H-8-aza-cyclohepta[e]indene-8-carboxylic acid ethyl ester To a stirred solution of Intermediate 3 (0.12 g, 0.37 mmol) in ethanol (2 ml) was added NaBH$_4$ (28 gm, 0.74 mmol). The reaction mixture was allowed to stir at RT for 1 hour. The reaction mixture was diluted with water and extracted with DCM (3×). The combined DCM extracts were washed with brine, dried (Na$_2$SO$_4$), and solvent evaporated in vacuo to give the sub-titled compound as a colorless oil (104 mg) which was used as obtained in the next step. MS: ESI (positive): 276 (M+H).

b). 1-Methoxy-1,3,6,7,9,10-hexahydro-2H-8-aza-cyclohepta[e]indene-8-carboxylic acid ethyl ester To a stirred solution of the product from step (a) (45 mg, 0.16 mmol) in DMF (2 ml) at RT over an argon atmosphere was added NaH (16 mg, 0.41 mmol). The reaction mixture was stirred until gas evolution had ceased and then iodomethane (0.025 ml, 0.41 mmol) was added. The reaction mixture was stirred at RT for 24 hours. The reaction mixture was diluted with water and extracted with ethyl acetate (3×). The combined ethyl acetate extracts were washed with brine, dried (Na$_2$SO$_4$), and solvent evaporated in vacuo to give the sub-titled compound as a colorless oil (52 mg). MS: ESI (positive): 290 (M+H).

c). 1-Methoxy-1,2,3,6,7,8,9,10-octahydro-8-aza-cyclohepta[e]indene

The product from step (b) (52 mg, 0.18 mmol) was dissolved in ethanol (2 and placed in a pressure tube. To this solution was added KOH (0.20 g, 3.60 mmol) and water (0.5 ml). The tube was sealed and the contents stirred at 120° C. for 48 hours. The reaction mixture was then cooled to RT and acidified with 2N HCl to pH 3. The aqueous mixture was then washed with diethyl ether (3×). The aqueous phase pH was then adjusted to 12 by addition of 2M NaOH and extracted with DCM (3×). The combined DCM extracts were washed with brine, dried (Na$_2$SO$_4$), and solvent evaporated in vacuo to give the titled compound as a colorless oil (19 mg). $^1$H NMR (300 MHz, CDCl$_3$) δ 7.02 (d, J=7.5 Hz, 1H); 6.98 (d, J=7.5 Hz, 1H); 4.92 (dd, J=5.4 Hz, 2.7 Hz, 1H); 3.35 (s, 3H); 3.15-2.76 (m, 10H); 2.24-2.12 (m, 2H); 1.99 (bs, 1H); MS: ESI (positive): 218 (M+1).

Chiral HPLC

The racemic free base products required derivatization of the basic amine to effectively separate the enantiomers.

Derivatization: Use of Trifluoracetimide Protecting Group
Formation

Into an appropriately sized flask, the racemic free base (1 eq) in DCM was placed. The reaction mixture was cooled to 0° C. and DIEA (1.5 eq) was added, followed by trifluoroacetic anhydride (1.5 eq). The reaction mixture was allowed to warm to room temperature, and after 30 minutes the reaction was quenched with water. The aqueous layer was extracted with DCM (3×). The combined DCM extracts were washed with brine, dried over Na$_2$SO$_4$, and solvent evaporated in vacuo to give the crude product. Purification by silica-gel chromatography gave the racemic trifluoroacetimide protected compound which was purified via chiral HPLC.

Deprotection

Each purified enantiomer was separately dissolved in an appropriately sized flask in MeOH. To this mixture, water was added at a ratio of 5 parts MeOH to 2 parts water. To the reaction mixture, K$_2$CO$_3$ was added (at a ratio of 100 mg/1 ml total volume). The reaction mixture was stirred at room temperature until the product formation was complete by LCMS. The reaction mixture was diluted with water (>10× total volume) and extracted with DCM (3×). The combined DCM extracts were washed with brine, dried (Na$_2$SO$_4$), and solvent evaporated in vacuo to give the individual enantiomers.

Derivatization: Use of the Cbz-Protecting Group
Formation

Into an appropriately sized flask, the racemic free base (1 eq) in DCM was placed. The reaction mixture was cooled to 0° C. and DIEA (1.5 eq) was added, followed by benzyl chloroformate (1.5 eq). The reaction mixture was allowed to warm to room temperature, and after 45 minutes, the reaction was quenched with 1M acetic acid. The aqueous layer was extracted with DCM (3×). The combined DCM extracts were washed with brine, dried over $Na_2SO_4$, and solvent evaporated in vacuo. The crude residue was purified by silica gel chromatography to give the racemic Cbz-protected compound which was purified via chiral HPLC.

Deprotection

Each purified enantiomer (1 eq) was separately dissolved in an appropriately sized flask in acetonitrile. The reaction mixture was cooled to 0° C. and iodotrimethylsilane (2 eq) was added drop-wise. After 1 hour, additional iodotrimethylsilane (2 eq) was added drop-wise, and the reaction mixture was stirred at 0° C. for an additional hour. The reaction mixture was partitioned between 1M AcOH and diethyl ether. The aqueous layer was washed with diethyl ether (3×). The aqueous layer was then basified with saturated aqueous $Na_2CO_3$ to pH 10. The basic aqueous layer was extracted with DCM (3×). The combined DCM extracts were washed with brine, dried over $Na_2SO_4$ and solvent evaporated in vacuo to give the individual enantiomers.

TABLE 1

Chiral HPLC data

| Compound | N-Protecting Group | Column type solvent conditions, flow rate | Peak 1 ($R_t$, min) | Peak 2 ($R_t$, min) |
|---|---|---|---|---|
| Example 2 | trifluoro-acetamide | Chiralpak AD-RH; 15% $H_2O$/85% MeOH, 8 ml/min | 13.8 | 16.5 |
| Example 3 | trifluoro-acetamide | Chiralpak AD-RH; 10% $H_2O$/90% MeOH, 8 ml/min | 10.2 | 11.9 |
| Example 4 | trifluoro-acetamide | Chiralpak AD-RH; 15% $H_2O$/85% MeOH, 7 ml/min | 17.8 | 23.0 |
| Example 5 | trifluoro-acetamide | Chiralpak AD-RH; 15% $H_2O$/85% MeOH, 7 ml/min | 17.3 | 19.6 |
| Example 6 | trifluoro-acetamide | Chiralpak AD-RH; 15% $H_2O$/85% MeOH, 7 ml/min | 15.0 | 17.1 |
| Example 7 | trifluoro-acetamide | Chiralpak AD-RH; 12.5% $H_2O$/87.5% MeOH, 7 ml/min | 23.3 | 28.7 |
| Example 8 | trifluoro-acetamide | Chiralpak AD-RH; 10% $H_2O$/90% MeOH, 7 ml/min | 12.8 | 15.5 |
| Example 9 | trifluoro-acetamide | Chiralpak AD-RH; 15% $H_2O$/85% MeOH, 7 ml/min | 19.4 | 22.0 |
| Example 10 | trifluoro-acetamide | Chiralpak AD-RH; 12.5% $H_2O$/87.5% MeOH, 7 ml/min | 23.4 | 27.8 |
| Example 11 | trifluoro-acetamide | Chiralpak AD-RH; 10% $H_2O$/90% MeOH, 8 ml/min | 12.8 | 17.6 |
| Example 12 | trifluoro-acetamide | Chiralpak AD-RH; 12.5% $H_2O$/87.5% MeOH, 7 ml/min | 17.4 | 22.7 |
| Example 14 | CBZ | Chiralpak AD-H; 3% EtOH/Hexanes, 30 ml/min | 16.5 | 24.5 |
| Example 15 | CBZ | Chiralpak AD-H; 2% EtOH/Hexanes, 30 ml/min | 18.0 | 24.0 |
| Example 16 | CBZ | Chiralpak AD-H; 2% EtOH/Hexanes, 30 ml/min | 17.0 | 22.0 |
| Example 17 | trifluoro-acetamide | Chiralpak AD-RH; 15% $H_2O$/85% MeOH, 7 ml/min | 18.6 | 21.2 |
| Example 18 | CBZ | Chiralpak AD-H; 2% EtOH/Hexanes, 30 ml/min | 17.0 | 20.5 |
| Example 19 | CBZ | Chiralpak AD-H; 1% EtOH/Hexanes, 30 ml/min | 23.0 | 26.5 |
| Example 20 | trifluoro-acetamide | Chiralpak AD-RH; 15% $H_2O$/85% MeOH, 8 ml/min | 14.4 | 17.7 |
| Example 21 | trifluoro-acetamide | Chiralpak AD-RH; 15% $H_2O$/85% MeOH, 7 ml/min | 19.9 | 23.7 |
| Example 22 | trifluoro-acetamide | Chiralpak AD-RH; 15% $H_2O$/85% MeOH, 7 ml/min | 16.3 | 21.2 |
| Example 23 | CBZ | Chiralpak AD-H; 2% EtOH/Hexanes, 30 ml/min | 24.1 | 32.0 |
| Example 24 | CBZ | Chiralpak AD-H; 2% EtOH/Hexanes, 30 ml/min | 30.0 | 39.5 |
| Example 25 | CBZ | Chiralpak AD-H; 1% EtOH/Hexanes, 30 ml/min | 30.2 | 45.1 |
| Example 26 | trifluoro-acetamide | Chiralpak AD-RH; 20% $H_2O$/80% MeOH, 7 ml/min | 26.3 | 30.0 |
| Example 27 | trifluoro-acetamide | Chiralpak AD-RH; 15% $H_2O$/85% MeOH, 7 ml/min | 21.4 | 24.5 |
| Example 28 | CBZ | Chiralpak AD-H; 25% EtOH/Hexanes, 30 ml/min | 9.8 | 24.3 |
| Example 29 | trifluoro-acetamide | Chiralpak AD-RH; 20% $H_2O$/80% MeOH, 7 ml/min | 19.4 | 22.7 |
| Example 30 | CBZ | Chiralpak AD-H; 20% EtOH/Hexanes, 30 ml/min | 11.3 | 18.2 |
| Example 31 | trifluoro-acetamide | Chiralpak AD-RH; 10% $H_2O$/90% MeOH, 7 ml/min | 10.9 | 14.3 |
| Example 32 | trifluoro-acetamide | Chiralpak AD-RH; 15% $H_2O$/85% MeOH, 7 ml/min | 14.0 | 18.9 |
| Example 33 | trifluoro-acetamide | Chiralpak AD-RH; 20% $H_2O$/80% MeOH, 7 ml/min | 36.5 | 43.4 |
| Example 36 | trifluoro-acetamide | Chiralpak AD-RH; 5% $H_2O$/95% MeOH, 7 ml/min | 9.8 | 15.7 |
| Example 37 | trifluoro-acetamide | Chiralpak AD-RH; 15% $H_2O$/85% MeOH, 8 ml/min | 17.2 | 22.0 |
| Example 38 | CBZ | Chiralpak AD-H; 5% EtOH/Hexanes, 30 ml/min | 22.5 | 34.0 |
| Example 40 | trifluoro-acetamide | Chiralpak AD-RH; 10% $H_2O$/90% MeOH, 7 ml/min | 13.7 | 19.0 |
| Example 41 | CBZ | Chiralpak AD-H; 5% EtOH/Hexanes, 30 ml/min | 13.5 | 18.0 |
| Example 43 | trifluoro-acetamide | Chiralpak AD-RH; 12.5% $H_2O$/87.5% MeOH, 7 ml/min | 12.6 | 15.0 |

Functional Potency of Compounds at $5HT_{2c}$

Agonist potency of compounds was evaluated using the functional assay described below and the data are shown in Table 2.

Cell Culture

5-$HT_2$ Cell lines: HEK 293 EBNA stably transfected cell lines expressing the VSV or INI isoform of human 5HT2c receptor (Genbank accession No. U49516), human 5-HT2A (Genbank accession No. X57830), or human 5-HT2B (Genbank accession No. NM_000867) were cultured in DMEM containing 10% dialysed FBS, 1% Penicillin/Streptomycin/L-Glutamine, and 7 μg/ml blasticidin at 37° C. in 5% $CO_2$ atmosphere.

Phosphotidyl Inositol Turnover Assay

The IP-One Tb kit (CisBio, cat#62IPAPEC) was used to perform direct quantitative measurements of myo-Inositol 1-Phosphate.

HEK 293 EBNA cells expressing human $5HT_2$ receptor of interest were harvested from T-175 cell culture flasks. Cells were washed 1× with PBS and resuspended in 1×IP1 Stimulation buffer (kit provided: 10 mM Hepes pH 7.4, 1 mM $CaCl_2$, 0.5 mM $MgCl_2$, 4.2 mM KCl, 146 mM NaCl, 5.5 mM glucose, 50 mM LiCl). Test compounds were serially diluted at 2× final concentration in 1×IP1 Stimulation buffer over the dose range $1×10^{-11}$M-$1×10^{-4}$M. Compounds were added to a white, non-binding surface 384-well plate, each dose tested in triplicate. Cell treatment was initiated by adding cells at $2×10^4$ cells/well to compounds plated in 384-well plate. For $5\text{-}HT_{2C}$ VSV and INI cell lines, plates were incubated at 37° C., 5% $CO_2$ for 30 minutes. For $5\text{-}HT_{2A}$ and $5\text{-}HT_{2B}$ cell lines, plates were incubated for 40 minutes. Cell stimulation was terminated by addition of IP-One Tb lysis buffer (kit provided-proprietary) containing IP1-d2 conjugate and subsequent addition of anti-IP1 cryptate Tb conjugate also diluted in IP-One Tb lysis buffer. Plates were incubated in the dark for 1 hr R.T. 15 μL/well of reaction mixtures were transferred to a low-volume 384-well Proxiplate (Perkin Elmer) and time-resolved fluorescence (TRF) signals were measured using an AnalystHT Multi-mode plate reader (Molecular Devices)—TRF was measured at 665 nM and 620 nM emission wavelengths.

Data Analysis

All data were analyzed by nonlinear least square curve fitting using Prism 5.0 software. Agonist stimulation of IP1 TRF ratio (TRF ratio=(665 nm/625 nm)*$1×10^4$) was fitted to sigmoidal dose response using equation Y=Bottom+(Top-Bottom)/(1+10^((X-LogIC_{50}))), where X is the logarithm of concentration of compounds and Y is the TRF ratio.

TABLE 2

5-HT2c PI turnover potency data of the more active isomer (where applicable).

| Structure | Potency at $5HT_{2c}$ (INI isoform) |
|---|---|
| 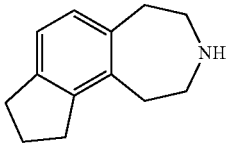 [SMILES: c1cc2c(c3c1CCC3)CCNCC2] | <10 nM |
| 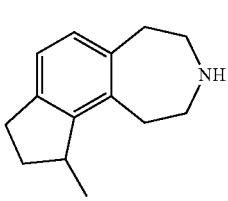 | <10 nM |

TABLE 2-continued

5-HT2c PI turnover potency data of the more active isomer (where applicable).

| Structure | Potency at $5HT_{2c}$ (INI isoform) |
|---|---|
| 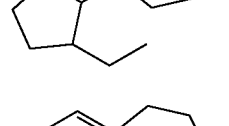 | <10 nM |
| 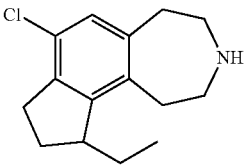 | <10 nM |
| 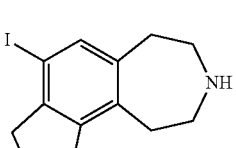 | <10 nM |
| 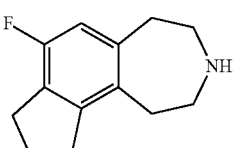 | <10 nM |
| 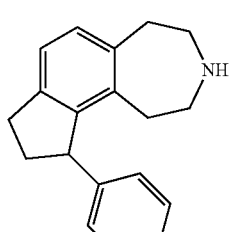 | <10 nM |
| 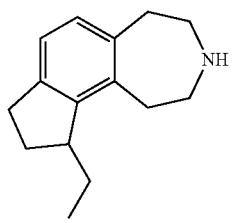 [SMILES: CCC1CCc2ccc3c(c21)CCNCC3] | <10 nM |
| 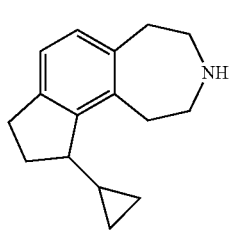 [SMILES: c1cc2c(c3c1CCNCC3)C(C1CC1)CC2] | <10 nM |

TABLE 2-continued
5-HT2c PI turnover potency data of the more active isomer (where applicable).
| Structure | Potency at $5HT_{2c}$ (INI isoform) |
|---|---|
| 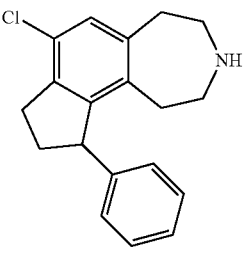 [SMILES: Clc1cc2c(c3c1CCC3c1ccccc1)CCNCC2] | <10 nM |
| 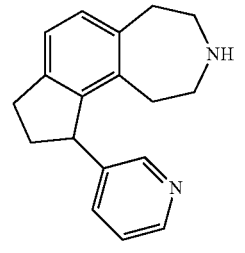 [SMILES: c1cncc(C2CCc3ccc4c(c32)CCNCC4)c1] | <10 nM |
| 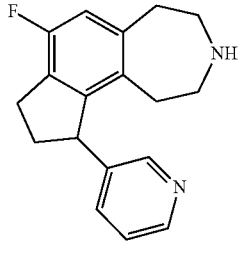 [SMILES: Fc1cc2c(c3c1CCC3c1cccnc1)CCNCC2] | <10 nM |
| 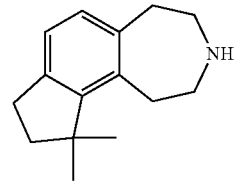 | <10 nM |
| 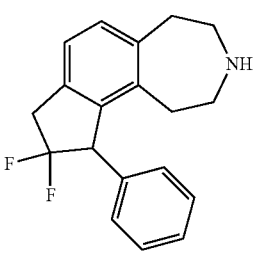 [SMILES: FC1(F)Cc2ccc3c(c2C1c1ccccc1)CCNCC3] | <10 nM |
| 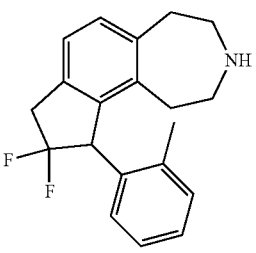 [SMILES: Cc1ccccc1C1c2c(ccc3c2CCNCC3)CC1(F)F] | <10 nM |
| 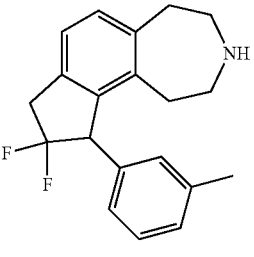 | <10 nM |
| 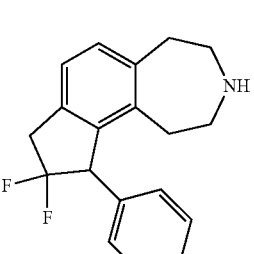 | <100 nM |
| 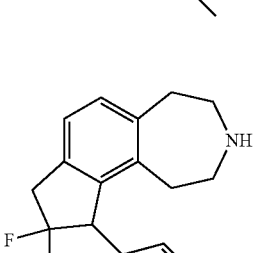 | <10 nM |
| 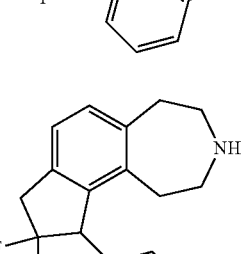 | <10 nM |

TABLE 2-continued
5-HT2c PI turnover potency data of the more active isomer (where applicable).
| Structure | Potency at 5HT$_{2c}$ (INI isoform) |
|---|---|
| 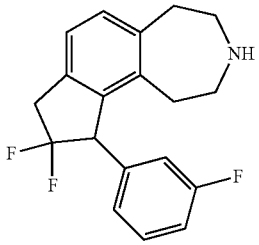 [SMILES: Fc1cccc(C2c3c(ccc4c3CCNCC4)CC2(F)F)c1] | <10 nM |
| 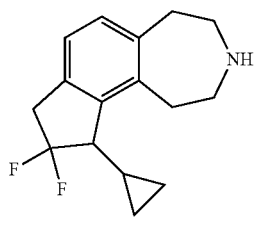 | <10 nM |
| 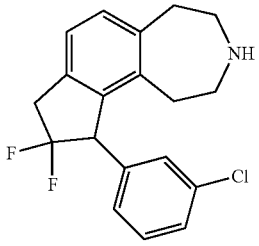 [SMILES: FC1(F)Cc2ccc3c(c2C1c1cccc(Cl)c1)CCNCC3] | <10 nM |
| 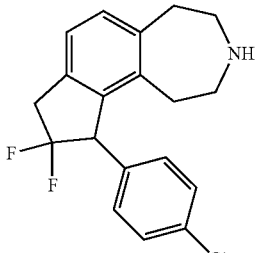 | <10 nM |
| 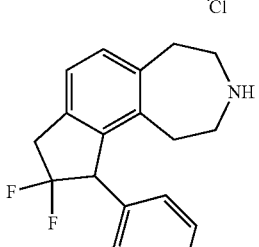 | <10 nM |
| 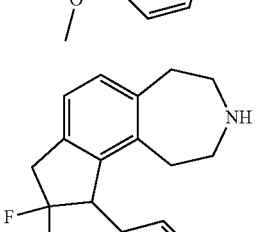 | <10 nM |
| 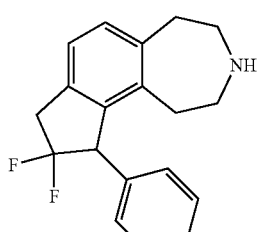 | <100 nM |
| 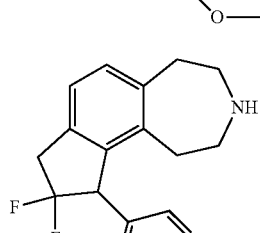 | <10 nM |
| 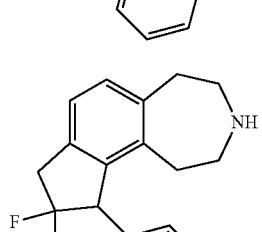 | <1000 nM |
| 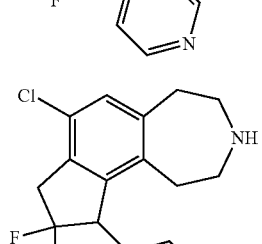 | <10 nM |
| 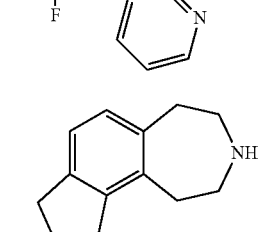 | <10 nM |
| 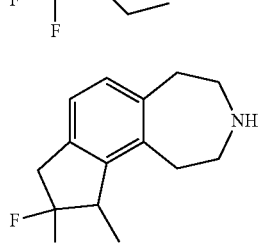 | <10 nM |

TABLE 2-continued

5-HT2c PI turnover potency data of the more active isomer (where applicable).

| Structure | Potency at 5HT$_{2c}$ (INI isoform) |
|---|---|
| (benzazepine with difluoro-indane and benzyl) | <10 nM |
| (benzazepine with difluoro-dimethyl indane) | <10 nM |
| (phenyl-substituted dimethyl indane benzazepine) | <1000 nM |
| (furo-fused benzazepine with ethyl) | <10 nM |
| (pyrano-fused benzazepine with ethyl) | <10 nM |
| (difluoro indane benzazepine with OMe) | <10 nM |
| (furo-fused benzazepine with phenyl) | <10 nM |
| (thiazole-substituted indane benzazepine) | <10 nM |
| (difluoro indane benzazepine with OEt) | <10 nM |
| (difluoro indane benzazepine) | <10 nM |
| (indane benzazepine with OMe) | <10 nM |

The invention claimed is:

1. A compound of the formula

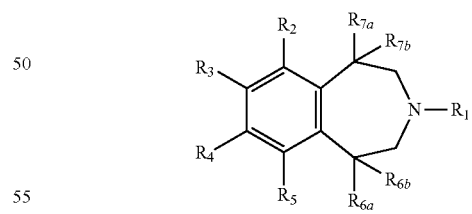

where
R$_1$ is selected from the group consisting of H, alkyl, perhaloalkyl, alkanoyl, C$_{1-8}$ alkylaryl, and C$_{1-8}$ alkylheteroaryl;
R$_2$ and R$_3$ are independently selected from the group consisting of H, halogen, C$_{1-8}$ alkyl, C$_{2-8}$ alkenyl, C$_{2-8}$ alkynyl, perhaloalkyl, CN, OR$_8$, NR$_8$R$_9$, SR$_8$, OCOR$_{10}$, CONR$_8$R$_9$, NR$_8$COR$_{10}$, NR$_8$CO$_2$R$_{10}$, SO$_2$NR$_8$R$_9$, SO$_2$R$_{10}$, NR$_8$SO$_2$R$_{10}$, aryl, heteroaryl, C$_{1-8}$ alkylaryl, and C$_{1-8}$ alkylheteroaryl;

$R_4$ and $R_5$ together with the atoms which they are attached form a 5- or 6-membered carbocycle ring, substituted with $R_{14a}$ and one or more of each of $R_{11a}$, $R_{11b}$, $R_{12a}$, $R_{12b}$, $R_{13a}$, $R_{13b}$, and $R_{14b}$;

$R_{6a}$ and $R_{6b}$ are independently selected from the group consisting of H, $C_{1-8}$alkyl, $OR_8$, and heteroaryl; or $R_{6a}$ and $R_{6b}$ taken together are —$CH_2CH_2$—;

$R_{7a}$ and $R_{7b}$ are independently selected from the group consisting of H, $C_{1-8}$alkyl, $OR_8$, aryl, and heteroaryl; or $R_{7a}$ and $R_{7b}$ taken together are —$CH_2CH_2$—;

$R_8$ is selected from the group consisting of H, $C_{1-8}$alkyl, $C_{2-8}$ alkenyl, $C_{2-8}$ alkynyl, perhaloalkyl, $C_{1-8}$ alkyl-O—$C_{1-8}$ alkyl, aryl, heteroaryl, $C_{1-8}$ alkyl-O-aryl, $C_{1-8}$ alkyl-O-heteroaryl, $C_{1-8}$ alkylaryl, and $C_{1-8}$ alkylheteroaryl;

$R_9$ is selected from the group consisting of H, $C_{1-8}$alkyl, $C_{2-8}$ alkenyl, $C_{2-8}$ alkynyl, perhaloalkyl, $C_{1-8}$ alkyl-O—$C_{1-8}$ alkyl, aryl, heteroaryl, $C_{1-8}$ alkyl-O-aryl, $C_{1-8}$ alkyl-O-heteroaryl, $C_{1-8}$ alkylaryl, and $C_{1-8}$ alkylheteroaryl;

$R_{10}$ is selected from the group consisting of $C_{1-8}$ alkyl, $C_{2-8}$ alkenyl, $C_{2-8}$ alkynyl, perhaloalkyl, $C_{1-8}$ alkyl-O—$C_{1-8}$ alkyl, aryl, heteroaryl, $C_{1-8}$ alkyl-O-aryl, $C_{1-8}$ alkyl-O-heteroaryl, $C_{1-8}$ alkylaryl, and $C_{1-8}$ alkylheteroaryl;

$R_{11a}$ and $R_{11b}$ are independently selected from the group consisting of H, halogen, $C_{1-8}$ alkyl, perhaloalkyl, aryl, and heteroaryl;

$R_{12a}$ and $R_{12b}$ are independently selected from the group consisting of H, halogen, $C_{1-8}$ alkyl, perhalo alkyl, aryl, and heteroaryl $R_{13a}$ and $R_{13b}$ are independently selected from the group consisting of H, halogen, $C_{1-8}$ alkyl, perhaloalkyl, aryl, and heteroaryl;

$R_{14a}$ is selected from the group consisting of halogen, $C_{1-8}$ alkyl, $C_{2-8}$ alkenyl, $C_{2-8}$ alkynyl, perhaloalkyl, CN, $OR_8$, $NR_8R_9$, $SR_8$, $OCOR_{10}$, $OCONR_8R_9$, $CONR_8R_9$, $NR_8COR_{10}$, $NR_8CO_2R_{10}$, $NR_8SO_2R_{10}$, aryl, heteroaryl, $C_{1-8}$ alkylaryl, and $C_{1-8}$ alkylheteroaryl, $R_{14b}$ is selected from the group consisting of H, halogen, $C_{1-8}$ alkyl, $C_{2-8}$ alkenyl, $C_{2-8}$ alkynyl, perhaloalkyl, CN, $OR_8$, $NR_8R_9$, $SR_8$, $OCOR_{10}$, $OCONR_8R_9$, $CONR_8R_9$, $NR_8COR_{10}$, $NR_8CO_2R_{10}$, $NR_8SO_2R_{10}$, aryl, heteroaryl, $C_{1-8}$ alkylaryl, and $C_{1-8}$ alkylheteroaryl;

or an isomer or a pharmaceutically acceptable salt thereof.

2. A compound as in claim 1, wherein $R_1$ is H.

3. A compound as in claim 1 wherein said compound has the formula:

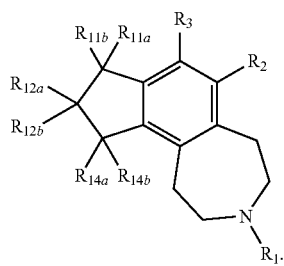

4. A compound as in claim 1 wherein said compound has the formula:

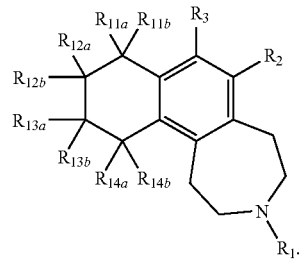

5. A compound as in claim 1, wherein said compound has one of the formulas:

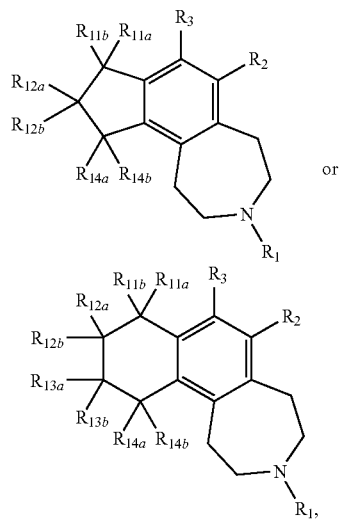

wherein
$R_1$ is H;
$R_2$ and $R_3$ are independently selected from the group consisting of H and halogen;
$R_{11a}$, $R_{11b}$, $R_{12a}$, $R_{12b}$, $R_{13a}$ and $R_{13b}$ are independently selected from the group consisting of H and halogen;
$R_{14a}$ is selected from the group consisting of halogen, $C_{1-8}$ alkyl, aryl, heteroaryl, $C_{1-8}$ alkylaryl, and $C_{1-8}$ alkylheteroaryl; and
$R_{14b}$ is selected from the group consisting of H, halogen, $C_{1-8}$ alkyl, aryl, heteroaryl, $C_{1-8}$ alkylaryl, and $C_{1-8}$ alkylheteroaryl;
or a pharmaceutically acceptable salt thereof.

6. A compound according to claim 1, wherein $R_1$, $R_2$, $R_3$, $R_{6a}$, $R_{6b}$, $R_{7a}$, $R_{7b}$ are H; and $R_4$ and $R_5$ together with the atoms which they are attached form a 5-membered carbocycle ring, substituted with $R_{14a}$ and one or more of each of $R_{11a}$, $R_{11b}$, $R_{12a}$, $R_{12b}$, and $R_{14b}$.

7. A compound according to claim 6, wherein $R_{11a}$ and $R_{11b}$ are both H.

8. A compound according to claim 6, wherein $R_{12a}$ and $R_{12b}$ are both F.

9. A compound according to claim 6, wherein $R_{14a}$ is aryl and $R_{14b}$ is H.

10. A compound selected from the group consisting of:
1-Methyl-1,2,3,6,7,8,9,10-octahydro-8-aza-cyclohepta[e]indene;

1-Ethyl-1,2,3,6,7,8,9,10-octahydro-8-aza-cyclohepta[e]indene;
1-Cyclopropyl-1,2,3,6,7,8,9,10-octahydro-8-aza-cyclohepta[e]indene;
1-Propyl-1,2,3,6,7,8,9,10-octahydro-8-aza-cyclohepta[e]indene;
4-Chloro-1-ethyl-1,2,3,6,7,8,9,10-octahydro-8-aza-cyclohepta[e]indene;
1-Ethyl-4-iodo-1,2,3,6,7,8,9,10-octahydro-8-aza-cyclohepta[e]indene;
1-Ethyl-4-fluoro-1,2,3,6,7,8,9,10-octahydro-8-aza-cyclohepta[e]indene;
1-Phenyl-1,2,3,6,7,8,9,10-octahydro-8-aza-cyclohepta[e]indene;
4-Chloro-1-phenyl-1,2,3,6,7,8,9,10-octahydro-8-aza-cyclohepta[e]indene;
1-Pyridin-3-yl-1,2,3,6,7,8,9,10-octahydro-8-aza-cyclohepta[e]indene;
4-Fluoro-1-pyridin-3-yl-1,2,3,6,7,8,9,10-octahydro-8-aza-cyclohepta[e]indene;
1,1-Dimethyl-1,2,3,6,7,8,9,10-octahydro-8-aza-cyclohepta[e]indene;
2,2-Difluoro-1-phenyl-1,2,3,6,7,8,9,10-octahydro-8-aza-cyclohepta[e]indene;
2,2-Difluoro-1-o-tolyl-1,2,3,6,7,8,9,10-octahydro-8-aza-cyclohepta[e]indene;
2,2-Difluoro-1-m-tolyl-1,2,3,6,7,8,9,10-octahydro-8-aza-cyclohepta[e]indene;
2,2-Difluoro-1-p-tolyl-1,2,3,6,7,8,9,10-octahydro-8-aza-cyclohepta[e]indene;
2,2-Difluoro-1-(3-trifluoromethyl-phenyl)-1,2,3,6,7,8,9,10-octahydro-8-aza-cyclohepta[e]indene;
2,2-Difluoro-1-(3-trifluoromethoxy-phenyl)-1,2,3,6,7,8,9,10-octahydro-8-aza-cyclohepta[e]indene;
2,2-Difluoro-1-(4-fluoro-phenyl)-1,2,3,6,7,8,9,10-octahydro-8-aza-cyclohepta[e]indene;
2,2-Difluoro-1-(3-fluoro-phenyl)-1,2,3,6,7,8,9,10-octahydro-8-aza-cyclohepta[e]indene;
1-Cyclopropyl-2,2-difluoro-1,2,3,6,7,8,9,10-octahydro-8-aza-cyclohepta[e]indene;
1-(3-Chloro-phenyl)-2,2-difluoro-1,2,3,6,7,8,9,10-octahydro-8-aza-cyclohepta[e]indene;
1-(4-Chloro-phenyl)-2,2-difluoro-1,2,3,6,7,8,9,10-octahydro-8-aza-cyclohepta[e]indene;
2,2-Difluoro-1-(2-methoxy-phenyl)-1,2,3,6,7,8,9,10-octahydro-8-aza-cyclohepta[e]indene;
2,2-Difluoro-1-(3-methoxy-phenyl)-1,2,3,6,7,8,9,10-octahydro-8-aza-cyclohepta[e]indene;
2,2-Difluoro-1-(4-methoxy-phenyl)-1,2,3,6,7,8,9,10-octahydro-8-aza-cyclohepta[e]indene;
2,2-Difluoro-1-pyridin-3-yl-1,2,3,6,7,8,9,10-octahydro-8-aza-cyclohepta[e]indene;
2,2-Difluoro-1-pyridin-4-yl-1,2,3,6,7,8,9,10-octahydro-8-aza-cyclohepta[e]indene;
4-Chloro-2,2-difluoro-1-pyridin-3-yl-1,2,3,6,7,8,9,10-octahydro-8-aza-cyclohepta[e]indene;
1-Ethyl-2,2-difluoro-1,2,3,6,7,8,9,10-octahydro-8-aza-cyclohepta[e]indene;
2,2-Difluoro-1-methyl-1,2,3,6,7,8,9,10-octahydro-8-aza-cyclohepta[e]indene;
1-Benzyl-2,2-difluoro-1,2,3,6,7,8,9,10-octahydro-8-aza-cyclohepta[e]indene;
2,2-Difluoro-1,1-dimethyl-1,2,3,6,7,8,9,10-octahydro-8-aza-cyclohepta[e]indene;
1,1-Dimethyl-4-phenyl-1,2,3,6,7,8,9,10-octahydro-8-aza-cyclohepta[e]indene;
1-Ethyl-1,2,7,8,9,10-hexahydro-6H-3-oxa-8-aza-cyclohepta[e]indene;
1-Ethyl-2,3,8,9,10,11-hexahydro-1H,7H-4-oxa-9-aza-cyclohepta[a]naphthalene;
2,2-Difluoro-1-methoxy-1,2,3,6,7,8,9,10-octahydro-8-aza-cyclohepta[e]indene;
1-Phenyl-7,8,9,10-tetrahydro-6H-3-oxa-8-aza-cyclohepta[e]indene;
1-Thiazol-2-yl-1,2,3,6,7,8,9,10-octahydro-8-aza-cyclohepta[e]indene;
1-Ethoxy-2,2-difluoro-1,2,3,6,7,8,9,10-octahydro-8-aza-cyclohepta[e]indene;
2,2-Difluoro-1,2,3,6,7,8,9,10-octahydro-8-aza-cyclohepta[e]indene; and
1-Methoxy-1,2,3,6,7,8,9,10-octahydro-8-aza-cyclohepta[e]indene.

11. A compound according to claim 1, wherein said compound is 1-Ethyl-1,2,3,6,7,8,9,10-octahydro-8-aza-cyclohepta[e]indene.

12. A compound according to claim 1, wherein said compound is 1-Phenyl-1,2,3,6,7,8,9,10-octahydro-8-aza-cyclohepta[e]indene.

13. A compound according to claim 1, wherein said compound is 4-Chloro-1-phenyl-1,2,3,6,7,8,9,10-octahydro-8-aza-cyclohepta[e]indene.

14. A compound according to claim 1, wherein said compound is 2,2-Difluoro-1-phenyl-1,2,3,6,7,8,9,10-octahydro-8-aza-cyclohepta[e]indene.

15. A compound according to claim 1, wherein said compound is 4-Chloro-2,2-difluoro-1-pyridin-3-yl-1,2,3,6,7,8,9,10-octahydro-8-aza-cyclohepta[e]indene.

16. A pharmaceutical composition comprising at least one compound of claim 1 and a pharmaceutically acceptable carrier.

17. A method of treating a disease, disorder and/or condition selected from the group consisting of obesity, attention deficit disorder, migraine, Type II diabetes, and epilepsy in a patient in need comprising administering an effective amount of at least one compound of claim 1 to said patient.

18. A compound of the formula

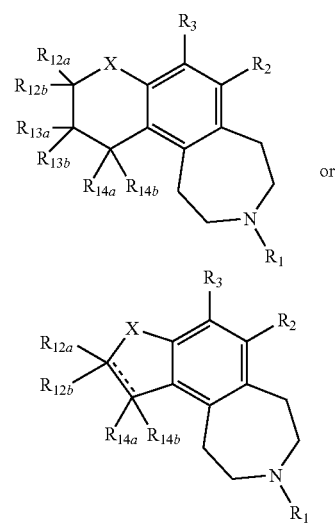

where
X is S, $SO_2$ or O;
$R_1$ is selected from the group consisting of H, alkyl, perhaloalkyl, alkanoyl, $C_{1-8}$ alkylaryl, and $C_{1-8}$ alkylheteroaryl;

$R_2$ and $R_3$ are independently selected from the group consisting of H, halogen, $C_{1-8}$ alkyl, $C_{2-8}$ alkenyl, $C_{2-8}$ alkynyl, perhaloalkyl, CN, $OR_8$, $NR_8R_9$, $SR_8$, $OCOR_{10}$, $CONR_8R_9$, $NR_8COR_{10}$, $NR_8CO_2R_{10}$, $SO_2NR_8R_9$, $SO_2R_{10}$, $NR_8SO_2R_{10}$, aryl, heteroaryl, $C_{1-8}$ alkylaryl, and $C_{1-8}$ alkylheteroaryl;

$R_8$ is selected from the group consisting of H, $C_{1-8}$alkyl, $C_{2-8}$ alkenyl, $C_{2-8}$ alkynyl, perhaloalkyl, $C_{1-8}$ alkyl-O— $C_{1-8}$ alkyl, aryl, heteroaryl, $C_{1-8}$ alkyl-O-aryl, $C_{1-8}$ alkyl-O-heteroaryl, $C_{1-8}$ alkylaryl, and $C_{1-8}$ alkylheteroaryl;

$R_9$ is selected from the group consisting of H, $C_{1-8}$alkyl, $C_{2-8}$ alkenyl, $C_{2-8}$ alkynyl, perhaloalkyl, $C_{1-8}$ alkyl-O— $C_{1-8}$ alkyl, aryl, heteroaryl, $C_{1-8}$ alkyl-O-aryl, $C_{1-8}$ alkyl-O-heteroaryl, $C_{1-8}$ alkylaryl, and $C_{1-8}$ alkylheteroaryl;

$R_{10}$ is selected from the group consisting of $C_{1-8}$ alkyl, $C_{2-8}$ alkenyl, $C_{2-8}$ alkynyl, perhaloalkyl, $C_{1-8}$ alkyl-O—$C_{1-8}$ alkyl, aryl, heteroaryl, $C_{1-8}$ alkyl-O-aryl, $C_{1-8}$ alkyl-O-heteroaryl, $C_{1-8}$ alkylaryl, and $C_{1-8}$ alkylheteroaryl;

$R_{12a}$ and $R_{12b}$ are independently selected from the group consisting of H, halogen, $C_{1-8}$ alkyl, perhalo alkyl, aryl, and heteroaryl;

$R_{13a}$ and $R_{13b}$ are independently selected from the group consisting of H, halogen, $C_{1-8}$ alkyl, perhaloalkyl, aryl, and heteroaryl;

$R_{14a}$ is selected from the group consisting of halogen, $C_{1-8}$ alkyl, $C_{2-8}$ alkenyl, $C_{2-8}$ alkynyl, perhaloalkyl, CN, $OR_8$, $NR_8R_9$, $SR_8$, $OCOR_{10}$, $OCONR_8R_9$, $CONR_8R_9$, $NR_8COR_{10}$, $NR_8CO_2R_{10}$, $NR_8SO_2R_{10}$, aryl, heteroaryl, $C_{1-8}$ alkylaryl, and $C_{1-8}$ alkylheteroaryl;

$R_{14b}$ is selected from the group consisting of H, halogen, $C_{1-8}$ alkyl, $C_{2-8}$ alkenyl, $C_{2-8}$ alkynyl, perhaloalkyl, CN, $OR_8$, $NR_8R_9$, $SR_8$, $OCOR_{10}$, $OCONR_8R_9$, $CONR_8R_9$, $NR_8COR_{10}$, $NR_8CO_2R_{10}$, $NR_8SO_2R_{10}$, aryl, heteroaryl, $C_{1-8}$ alkylaryl, and $C_{1-8}$ alkylheteroaryl, provided that when the ⎯⎯⎯ is a double bond, then $R_{12b}$ and $R_{14b}$ are not present, or an isomer or a pharmaceutically acceptable salt thereof.

19. A compound as in claim 18, wherein said compound has one of the formulas:

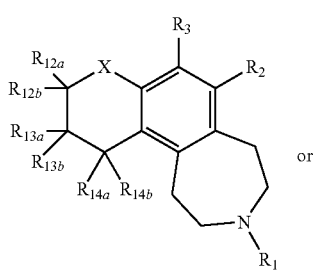

or

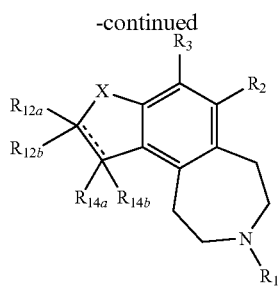

wherein
X is S, $SO_2$ or O;
$R_1$ is H;
$R_2$ and $R_3$ are independently selected from the group consisting of H and halogen;
$R_{12a}$, $R_{12b}$, $R_{13a}$ and $R_{13b}$ are independently selected from the group consisting of H and halogen;
$R_{14a}$ is selected from the group consisting of halogen, $C_{1-8}$ alkyl, aryl, heteroaryl, $C_{1-8}$ alkylaryl, and $C_{1-8}$ alkylheteroaryl; and
$R_{14b}$ is selected from the group consisting of H, halogen, $C_{1-8}$ alkyl, aryl, heteroaryl, $C_{1-8}$ alkylaryl, and $C_{1-8}$ alkylheteroaryl;
provided that when the ⎯⎯⎯ is a double bond, then $R_{12b}$ and $R_{14b}$ are not present,
or a pharmaceutically acceptable salt thereof.

20. A compound as in claim 18 wherein said compound has the formula:

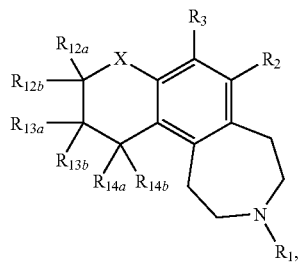

wherein X is S, $SO_2$ or O.

21. A compound as in claim 18 wherein said compound has the formula:

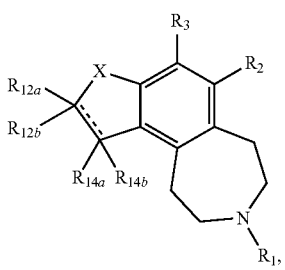

wherein X is S, $SO_2$ or O.

* * * * *